US007414068B2

(12) United States Patent
Lim et al.

(10) Patent No.: US 7,414,068 B2
(45) Date of Patent: Aug. 19, 2008

(54) BENZOPYRAN DERIVATIVES SUBSTITUTED WITH SECONDARY AMINES INCLUDING TETRAZOLE, METHOD FOR THE PREPARATION THEREOF AND PHARMACEUTICAL COMPOSITIONS CONTAINING THEM

(75) Inventors: Hong Lim, Seoul (KR); Dong-Ha Lee, Taejon-si (KR); Sun-Ok Kim, Taejon-si (KR); In-Young Choi, Taejon-si (KR); Sung-Eun Yoo, Chungchongnam-do (KR); Kyu-Yang Yi, Taejon-si (KR); Sun-Kyung Lee, Taejon-si (KR); Jee-Hee Suh, Taejon-si (KR); Nak-Jeong Kim, Taejon-si (KR); Byung-Ho Lee, Taejon-si (KR); Ho-Won Seo, Taejon-si (KR); Hwa-Sup Shin, Taejon-si (KR)

(73) Assignee: Dongbu Hannong Chemical Co., Ltd., Seoul (KR)

( * ) Notice: Subject to any disclaimer, the term of this patent is extended or adjusted under 35 U.S.C. 154(b) by 462 days.

(21) Appl. No.: 10/510,835

(22) PCT Filed: Apr. 10, 2003

(86) PCT No.: PCT/KR03/00727

§ 371 (c)(1),
(2), (4) Date: Oct. 8, 2004

(87) PCT Pub. No.: WO03/084464

PCT Pub. Date: Oct. 16, 2003

(65) Prior Publication Data

US 2006/0035948 A1    Feb. 16, 2006

(30) Foreign Application Priority Data

Apr. 10, 2002    (KR) ...................... 10-2002-0019460

(51) Int. Cl.
*A61K 31/41* (2006.01)
*C07D 257/04* (2006.01)
(52) U.S. Cl. ...................................... 514/381; 548/254
(58) Field of Classification Search ................. 514/381; 548/254
See application file for complete search history.

(56) References Cited

U.S. PATENT DOCUMENTS 5,837,702 A * 11/1998 Rovnyak et al. ............ 514/218
6,034,256 A *  3/2000 Carter et al. ................ 549/456

OTHER PUBLICATIONS

Mattson, M. P., et al., Calcium, Free Radicals, and Excitotoxic Neuronal Death in Primary Cell Culture, *Methods in Cell Biology*, vol. 46, pp. 187-216, (1995).

Zhang, Y., et al., "Basic FGF, NGF, and IGFs Protect Hippocampal and Cortical Neurons Against Iron-Induced Degeneration", *Journal of Cerebral Blood Flow and Metabolism*, vol. 13, No. 3, pp. 378-388, (1993).
Okubo, S., et al., "Myocardial preconditioning: Basic concepts and potential mechanisms", *Molecular and Cellular Biochemistry*, vol. 196, pp. 3-12, (1999).
Starkov, A.A., "'Mild' Uncoupling of Mitochondria", *Bioscience Reports*, vol. 17, No. 3, pp. 273-279, (1997).
Skulachev, V.P., "Role of uncoupled and non-coupled oxidations in maintenance of safely low levels of oxygen and its one-electron reductants", *Quarterly Reviews of Biophysics*, vol. 29, No. 2, pp. 169-202, (1996).
Grover, G.J., "Pharmacology of ATP-sensitive potassium channel (KATP) openers in models of myocardial ischemia and reperfusion", *Can. J. Physiol. Pharmacol.*, vol. 75, pp. 309-315, (1997).
Lopaschuk, G.D., et al., "Manipulation of Energy Metabolism in the Heart", *Science & Medicine*, pp. 42-51, (Nov./Dec. 1997).
Atwal, K.S., et al., "Cardioselective Anti-Ischemic ATP-Sensitive Potassium Channel Openers. 3. Structure-Activity Studies on Benzopyranyl Cyanoguanidines: Modification of the Cyanoguanidine Portion", *J. Med. Chem.* vol. 38, No. 17, pp. 3236-3245, (1995).
Rovnyak, G.C., et al., "Cardioselective Antiischemic ATP-Sensitive Potassium Channel (KATP) Openers. 5. Indentification of 4-(N-Aryl)-Substitiuted Benzopyran Derivatives with High Selectivity", *J. Med. Chem.* vol. 40, No. 1, pp. 24-34, (1997).
Atwal, K.S., et al., "Treatment of Myocardial Ischemia with ATP-Sensitive Postassium Channel (KATP) Openers", *Current Pharmaceutical Design*, vol. 2, No. 5, pp. 585-595, (1996).
Folkman, J., et al., "Angiogenic Factors", *Science*, vol. 235, pp. 442-447, (1987).
Lee, A., et al., "Shark Cartilage Contains Inhibitors of Tumor Angiogenesis", *Science*, Vo. 221, pp. 1185-1187, (1983).
Crum, R., et al., "A New Class of Steroids Inhibits Angiogensis in the Presence of Heparin or a Heparin Fragment", *Science*, vol. 230, pp. 1375-1378, (1985).
Jurd, L., "New Anti-tumor Agents. 2. Benzopyranylamine Compounds", *J. Heterocyclic Chem.*, vol. 33, No. 6, pp. 1919-1925, (1996).
Gladstone, D.J., et al., "Toward Wisdom From Failure: Lessons From Neuroprotective Stroke Trials and New Therapeutic Directions", *Stroke*, vol. 33, pp. 2123-2136, (2002).
Sziraki, I., et al., "Manganese: A Transition Metal Protects Nigrostriatal Neurons from Oxidative Stress in the Iron-Induced Animal Model of Parkinsonism", *Neuroscience*, vol. 85, No. 4, pp. 1101-1111, (1998).
Goodman, Y., et al., "K+ channel openers protect hippocampal neurons against oxidative injury and amyloid β-peptide toxicity", *Brain Research*, vol. 706, pp. 328-332, (1996).

(Continued)

*Primary Examiner*—Golam M. M. Shameem
*Assistant Examiner*—Susannah Chung
(74) *Attorney, Agent, or Firm*—Joshua B. Goldberg; Tanya E. Harkins

(57) ABSTRACT

The present invention relates to benzopyran derivatives substituted with secondary amines including tetrazole, method for preparing thereof and pharmaceutical compositions containing them. The compounds of the present invention can be used for protecting neuronal cells and brain damage; antioxidation; inhibiting NO generation; protecting heart; suppressing angiogenesis; protecting preserving organs such as kidney, heart and tissue, and protecting organs in major cardiovascular surgery.

7 Claims, No Drawings

OTHER PUBLICATIONS

McCord, J.M., "The Evolution of Free Radicals and Oxidative Stress", *The American Journal of Medicine*, vol. 108, pp. 652-659, (2000).

Moreau, J., et al., "Central adenosine $A_{2A}$ receptors: an overview", *Brain Research Reviews*, vol. 31, pp. 65-82, (1999).

Loidl, C.F., et al., "Effects of hypothermia and gender on survival and behavior after perinatal asphyzia in rats", *Physiology & Behavior*, vol. 68, pp. 263-269, (2000).

Naka, K., et al., "Effects of cilostazol on development of experimental diabetic neuropathy: functional and structural studies, and Na+-K+-ATPase acidity in peripheral nerve in rats with streptozotocin-induced diabetes", *Diabetes Research and Clinical Practice*, vol. 30, pp. 153-162, (1995).

Chambers, D.J., et al., "Developments in Cardioprotection: 'Polarized' Arrest as an Alternative to 'Depolarized' Arrest", *Ann. Thorac. Surg.*, vol. 68, pp. 1960-1966, (1999).

Folkman, J., et al., "Angiogensis", *The Journal of Biological Chemistry*, vol. 267, No. 16, pp. 10931-10934, (1992).

Mazzon, E., et al., "GPI 6150, a poly (ADP-ribose) polymerase inhibitor, exhibits an anti-inflammatory effect in rat models of inflammation", *European Journal of Pharmacology*, vol. 415, pp. 85-94, (2001).

Nieber, K., "Hypozia and Neuronal Function under in Vitro Conditions", *Pharmacol. Ther.* vol. 82, No. 1, pp. 71-86, (1999).

Paschen, W., et al., "Comparison of In Vitro Ischemia-Induced Disturbances in Energy Metabolism and Protein Synthesis in the Hippocampus of Rats and Gerbils", *Journal of Neurochemistry*, vol. 65, pp. 1692-1697, (1995).

Luhmann, H.J., "Ischemia and Lesion Induced Imbalances in Cortical Function", *Procgress in Neurobiology*, vol. 48, pp. 131-166, (1996).

De Keyser, J., et al., "Clinical trials with neuroprotective drugs in acute ischaemic stroke: are we doing the right thing?", *Trends Neurosci.*, vol. 22, pp. 535-540, (1999).

Dirnagle, U., et al., "Pathobiology of ischaemic stroke: an integrated view", *Trends Neurosci.* vol. 22, pp. 391-397, (1999).

\* cited by examiner

BENZOPYRAN DERIVATIVES SUBSTITUTED WITH SECONDARY AMINES INCLUDING TETRAZOLE, METHOD FOR THE PREPARATION THEREOF AND PHARMACEUTICAL COMPOSITIONS CONTAINING THEM

TECHNICAL FIELD

The present invention relates to benzopyran derivatives substituted with secondary amines including tetrazole represented by following formula 1, method for preparing thereof and pharmaceutical composition containing them.

FORMULA 1

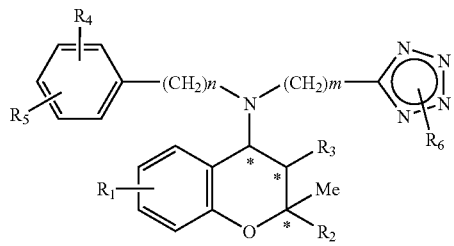

Wherein, $R_1$, $R_2$, $R_3$, $R_4$, $R_5$, $R_6$, n, m and * are as defined in the description.

BACKGROUND OF THE INVENTION

Neurons in the mammalian CNS (central nervous system) are highly sensitive to the availability of oxygen. It is well known that a transient critical reduction of oxygen within the intact brain, triggers a various pathological phenomena, finally a fatal brain damage [K. Nieber, Pharmacol. Ther. 1999, 82, 71]. Oxygen can become unavailable to the brain through a loss of blood flow (ischemia) following cardiac arrest or occlusion of intracranial vessels by thrombosis and embolism, or through an insufficient oxygen concentration in the blood (hypoxia).

Ischemic cell injury may arise from complex interactions biochemical cascades, which includes disturbances in among electrophysiological, hemodynamical and energy metabolism [W. Paschen and B. Djuricic, J. Neurochem. 1995, 65, 1692] and modifications in synaptic transmission [H. J. Luhmann, Prog. Neurobiol. 1996, 48, 131]. The disturbed ion homeostasis characterized by enhanced cellular $K^+$ efflux and $Na^+$ and $Ca^{2+}$ influx is followed by a substantial extracellular acidosis, free radical formation, cell swelling, and inhibition of protein synthesis, which are connected with excitatory amino-acid receptor, Ca-dependent or ATP-dependent K-channel, etc. As explained above, the ischemic cell damage occurred by a cascade of biochemical events, not by single event. So, several strategies are suggested for the development of neuroprotective agents and it is also suggested that the effective intervention on several key steps during ischemic cascade is necessary to be an effective therapeutic agent for brain ischemia [De Keyser et al. Trends Neurosci., 1999, 22, 535; Dirnagl et al. Trends Neurosci., 1999, 22, 391; Gladstone et al. Stroke, 2002, 33, 2123].

Even after blood flow is restored, oxygen can also enhance the biochemical reactions that generate free radicals, which can lead to a potential for "reperfusion injury" to occur. Both acute and chronic injury of tissues and organs are known to be caused by ischemia-reperfusion or by endotoxins via bacterial infection. In order to prevent the brain injury caused by ischemia-reperfusion, the brain must be protected during ischemic period to avoid additional injury and pathological progressive cellular changes have to minimize.

For that purpose, the development of several neuroprotectives such as excitatory amino acid antagonists, anti-oxidants, adenosine agonists and $K_{ATP}$ channel openers are being pursued.

Damage or death of neurons is known to be a main cause for various neurological disorders such as stroke, head trauma, Alzheimer's disease, Parkinson's disease, infant asphyxia, glaucoma and daiabetic neuropathy, etc [G. J. Zoppo et al., Drugs 1997, 54, 9: I. Sziraki et al., Neurosci, 1998, 85, 1101].

Neurons are damaged by various factors including increases in iron concentration, reactive oxygen species, and peroxidants within neurons [M. P. Mattson et al., Methods Cell Biol. 1995, 46, 187; Y. Goodman et al., Brain Res. 1996, 706, 328].

Free radicals are generated in cells by the oxidative stress. An excess of oxygen free radicals facilitates lipid peroxidation, so that peroxidants are accumulated in neurons and it also causes the change in protein synthesis and DNA. The reactive free radicals accumulated in cells are known to be responsible for a variety of diseases [J. M. McCord, Am J. Med. 2000, 108, 652]. Including inflammatory diseases such as arthritis; atherosclerosis; cardiac infarction; and neurodegenerative disease such as dementia, allergy, cancer as well as acute and chronic injury of tissues and organs.

Therefore, therapeutic approaches to minimize the damage or death of neurons have been pursued, including the inhibition of lipid peroxidation, NO formation, and reactive oxygen species induced by endotoxins. To date, anti-oxidants are reported to ameliorate the neuronal damage and death caused by an increase of iron concentration within neurons. Much effort has been continued to develop pharmaceutical drugs which are able to prevent neuronal damage by oxidative stress (Y. Zhang et al., J. Cereb. Blood Flow Metab. 1993, 13, 378).

There are reports that $K_{ATP}$ opening is related to the induction of anti-oxidant enzymes [S. Okubo et al., Mol. and cell Biochem., 1999, 196, 3], and to decrease the release of excitatory amino acid [J-L Moreau, G. Huber, Brain Res., 1999, 31, 65].

Diazoxide, a $K_{ATP}$ channel opener, has been reported to reversibly oxidize flavoproteins in mitochondria, resulting in inhibition of the formation of oxygen free radicals, which may protect cell injury by oxidative stress [A. A. Starkov, Biosci, Rep. 1997, 17, 273; V. P. Skulachev, Q. Rev. Biophus. 1996, 29, 169].

Infant asphyxia (IA), triggered by transient deficiency of oxygen supply during delivery, was reported to be caused by the reduction of energy production, damage of cell membrane due to oxygen free radical, release of excitatory neurotransmitters, change of intracellular ion concentrations including calcium, zinc, etc. IA is a major worldwide problem, because if IA is severe, the chances of mortality are high (approximately ⅓ of the total infant mortality). In addition, it can produce long term sequela such as movement disorders, learning disabilities, epilepsy, dystonia, mental retardation, and spasticity [C. F. Loid et. al. Physiology and Behavior, 2000, 68, 263-269].

Antioxidant enzymes, allopurinol, Vitamine C & E, free radical scavengers, inhibitors of excitatory neurotransmitters, calcium channel blockers such as nimodipine and flunarizine, inhibitors of NO formation, hyperglycemic and hypothermic therapy may be beneficial for the protection of brain injury, but their clinical application is still limited.

Glaucoma, one of the leading causes of blindness, is defined as an optic neuropathy associated with characteristic changes in optic nerve. In humans, the optic nerve consists of 1 million axons from neurons whose perikarya reside primarily in the ganglion cell layer and, to a less extent, in the inner part of the inner nuclear layer. The excavated appearance of the optic nerve head in glaucoma is thought to be caused by the death and subsequent loss of ganglion cells and their axons [N. N. Osborne, et. al. *Survey of ophthalmology*, 43; suppl. 1999, S102-s128].

Neuroprotective agents in glaucoma may protect death of retinal neurons, in particular the ganglion cells, either directly or indirectly. A variety of agents such as NMDA (N-methyl-D-aspartate) receptor antagonist, â-blockers, calcium antagonists, and antioxidants can be used to protect the death of retinal neurons induced by ischemia and damage of optic nerves.

Although the pathogenesis of diabetic neuropathy has not been clearly established, two main hypotheses have been proposed for it. One is metabolic abnormalities, and the other is blood flow deficits in peripheral nerve [K. Naka et. al. *Diabetes Research and Clinical Practice*, 1995, 30, 153-162]. Acetyl-L-carnitine (ALC) by stimulating metabolism of lipid and improving impaired nociceptive responses of neurons, and Prosaptide by releasing neutrophic factors are in clinical trials. In addition, Memantine, showing good effects on vascular dementia through the regulation of NMDA receptor, is pursuing clinical trial. Then, neuroprotective agents having a variety of mechanisms of action may be developed to treat diabetic neuropathy.

Ischemic heart diseases are usually caused by myocardial ischemia, when the oxygen supply is significantly decreased compared to the oxygen demand due to the imbalance between them [G. J. Grover, *Can. J. Physiol.*, 1997, 75, 309; G. D. Lopaschuk et al. *Science &Medicine*, 1997, 42]. Myocardial ischemia triggers various pathophysiological changes progressively that will ultimately lead to irreversible myocardial injury, cell death and tissue necrosis. At a stage where the injury to the cells is reversible, this process can be prevented by early reperfusion of the myocardium. However, there is potential for "reperfusion-injury" to occur [D. J. Hearse, *Medicographia*, 1996, 18, 22].

To delay the ischemic cascade and to minimize the reperfusion-injury, the use of adenosine agonists, inhibitors of $Na^+$-$K^+$ antiport, oxygen free radical scavengers and $K_{ATP}$ (ATP sensitive potassium channel) openers are investigated as well as ACE (Angiotensin converting enzyme) inhibitors and calcium antagonists. In addition, global ischemia occurs during cardiac surgery or during heart storage prior to transplantation. Recent studies reported that the addition of $K_{ATP}$ openers to a hyperkalemic cardioplegic solution, improved the recovery of postischemic contractile function after normothermic or short periods of hypothermic ischemia [D. J. Chambers, D. J. Hearse, *Ann. Thoar. Surg.*, 1999, 68, 1960.]. The use of those compounds as protectants or curatives for the organs related to "ischemia-reperfusion injury" such as retina and skeletal muscles besides heart and brain, in being investigated.

As mentioned above, since ischemic cascades proceed by complex interactions, it may be a useful strategy to develop the compound acting at more than one target site in ischemic cascade.

$K_{ATP}$ is found in a variety of tissues including cardiac muscle, smooth muscle skeletal muscle, kidney, pancreatic β-cells, the brain and central nerve system, which makes it attractive as a drug target. However, the same diversity poses a difficulty of finding tissue selective agents.

Differently from conventional potassium channel openers, the benzopyranyl cyanoguanidine compound (BMS-180448) represented by the following formula 4 and benzopyranyl imidazole compound (BMS-191095) represented by the following formula 5, have been reported to show modest antiischemic potency with excellent cardiac selectivity. Although the compound represented by formula 5 had all desirable features to serve as a lead compound, it still retains some degree of vasorelaxant and hypotensive activities [K. S. Atwal et al., *J. Med. Chem.*, 1995, 38, 3236; K. S. Atwal et al., *J. Med. Chem.*, 1996, 40, 24; K. S. Atwal et al., *Current Pharmaceutical Design*, 1996, 2, 585]. Therefore, more cardioselective compounds which have cardioprotective potency without lowering of blood pressure significantly, still give the prospects for the development of a novel cardioprotectant.

FORMULA 4

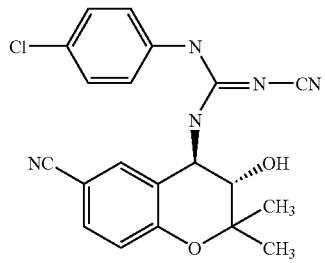

FORMULA 5

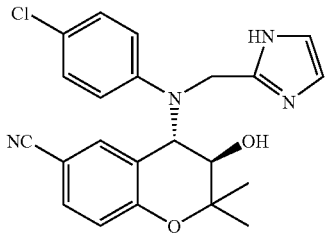

The ratio of cancer in human diseases is being gradually increased. Angiogenesis, formation of new blood vessels, is recognized as the core process for growth and metastasis of solid tumors (Folkma, J. et al., *J. Biol. Chem.* 1992, 267, 10931-10934). Angiogenesis is controlled by inducers and inhibitors of angiogenesis. When the balance between them is broken, that is, when angiogenesis inducers prevail over angiogenesis inhibitors, a large quantity of new blood vessels are formed. Angiogenesis is closely related to various physiological phenomena, such as embryonic development, wound healing, chronic inflammation, hemangiomas, diabetic retinopathy, rheumatoid arthritis, psoriasis, AIDS complications, and the growth and metastasis of malignant tumors (Forkman, J., Klagsbrun. M. *Science*, 1987, 235, 442-447). Angiogenesis includes a series of processes such as the migration, proliferation and differentiation of endothelial cells, and is an important prerequisite for the growth and metastasis of cancers. In detail, because the growing tumor cells require the formation of blood vessels from host cells, angiogenesis promoters derived from tumors stimulate to induce the angiogenesis into the tumor mass. Afterwards, the blood vessels formed around the malignant tumors facilitate to metastasize the tumor cells to other sites. Therefore, the inhibition of angiogenesis leads to the prevention of the growth and metastasis of cancers. As one of the important research areas for the developing of anti-cancer drugs, extensive attention is paid to the finding of angiogenesis inducers and angiogenesis inhibitors, and the revealing of their working mechanisms.

Thus far, proteins such as prostamine and tumor necrotic factors, factors derived from cartilage tissues, and cortisone called angiostatic steroids and various steroid derivatives, have been found to be able to play roles as angiogenesis inhibitors. In particular, hydrocortisone exhibits anti-angiogenetic activity by cotreatment with heparin (Lee, A. et al., *Science*, 1983, 221, 1185-1187); Crum, R. et al., *Science*, 1985, 230, 1375-1378). However, these compounds have a potential problem to treat cancers effectively owing to their cytotoxicity.

DISCLOSURE OF THE INVENTION

The present invention provides benzopyran derivatives substituted with secondary amine including tetrazole, their stereoisomers or their pharmaceutically acceptable salts.

The present invention provides further a method for preparing thereof.

The present invention provides further a pharmaceutical composition comprising the benzopyran derivatives substituted with secondary amine including tetrazole, their stereoisomers or their pharmaceutically acceptable salts as an effective ingredient.

In order to accomplish the aforementioned goal, the present invention provides benzopyran derivatives substituted with secondary amine including tetrazole represented by following formula 1, their stereoisomers or their pharmaceutically acceptable salts.

FORMULA 1

wherein, $R_1$ is H, F, Cl, Br, $CF_3$, $NO_2$, CN, $OR^a$,

$COOR^a$, $NH_2$, $NHS(O)_lR^a$,

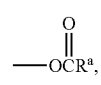

or $S(O)_lR^a$, provided that $R^a$ is H, $C_1$-$C_4$ straight or branched alkyl or aryl, l is an integer of 0-2;

$R_2$ is $CH_2OR^a$,

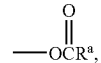

provided that $R^a$ is as defined in the above, $R^b$ and $R^c$ are independently $C_1$-$C_4$ straight or branched alkyl, Z is a straight or branched $C_1$-$C_5$ alkyl;

$R_3$ is OH, F, Cl, Br, $ONO_2$ or

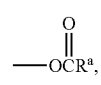

provided that $R^a$ is as defined in the above;

$R_4$ and $R_5$ is independently H, F, Cl, Br, $C_1$-$C_3$ straight or branched alkyl, $OR^a$, $CF_3$, $OCF_3$, $NO_2$,

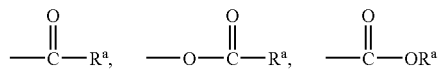

or $SO_3R^a$, provided that $R^a$ is as defined in the above;
$R_6$ is H, $C_1$-$C_3$ straight or branched alkyl;
n and m are independently an integer of 0-2;
* represents a chiral carbon.

Preferably, in the compound of formula 1,
$R_1$ is $NO_2$, CN, or $NH_2$;
$R_2$ is

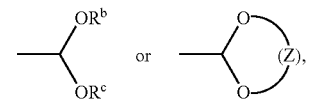

provided that $R^b$ and $R^c$ are independently $C_1$-$C_3$ straight or branched alkyl, Z is $C_2$-$C_3$ straight or branched alkyl;

$R_3$ is OH or

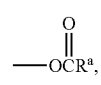

provided that $R^a$ is $C_1$-$C_3$ straight or branched alkyl;
$R_4$ and $R_5$ are independently H, F, Cl, $C_1$-$C_3$ straight or branched alkyl, $OR^a$, $CF_3$, $OCF_3$ or $NO_2$, provided that $R^a$ is $C_1$-$C_3$ straight or branched alkyl;
$R_6$ is $C_1$-$C_3$ straight or branched alkyl;
n and m are independently an integer of 0-1.

The present invention includes all the solvates and hydrates which can be prepared from benzopyran derivatives substituted with secondary amines including tetrazole of formula 1 in addition to benzopyran derivatives of formula 1 and their pharmaceutically acceptable salts.

Also, The present invention includes all the separate stereochemical isomers, i.e. diastereomerically pure or enantiomerically pure compounds which have one or more chiral centers at 2, 3 and 4-positions, in addition to the racemic mixtures or diastereomeric mixtures of benzopyran derivatives of formula 1.

Preferably, the compounds of formula 1 comprise:
1) (2S,3S,4R)-6-nitro-4-[N-(4-chlorophenyl)-N-(2-methyl-2H-tetrazol-5-ylmethyl)amino]-3-hydroxy-2-methyl-2-dimethoxymethyl-3,4-dihydro-2H-1-benzopyran
2) (2S,3R,4S)-6-nitro-4-[N-(4-chlorophenyl)-N-(2-methyl-2H-tetrazol-5-ylmethyl)amino]-3-hydroxy-2-methyl-2-dimethoxymethyl-3,4-dihydro-2H-1-benzopyran
3) (2S,3S,4R)-6-nitro-4-[N-(2-methyl-2H-tetrazol-5-ylmethyl)phenylamino]-3-hydroxy-2-methyl-2-dimethoxymethyl-3,4-dihydro-2H-1-benzopyran
4) (2S,3R,4S)-6-nitro-4-[N-(2-methyl-2H-tetrazol-5-ylmethyl)phenylamino]-3-hydroxy-2-methyl-2-dimethoxymethyl-3,4-dihydro-2H-1-benzopyran
5) (2S,3S,4R)-6-nitro-4-[N-(4-fluorophenyl)-N-(2-methyl-2H-tetrazol-5-ylmethyl)amino]-3-hydroxy-2-methyl-2-dimethoxymethyl-3,4-dihydro-2H-1-benzopyran
6) (2S,3R,4S)-6-nitro-4-[N-(4-fluorophenyl)-N-(2methyl-2H-tetrazol-5-ylmethyl)amino]-3-hydroxy-2-methyl-2-dimethoxymethyl-3,4-dihydro-2H-1-benzopyran
7) (2S,3S,4R)-6-nitro-4-[N-benzyl-N-(2-methyl-2H-tetrazol-5-ylmethyl)amino]-3-hydroxy-2-methyl-2-dimethoxymethyl-3,4-dihydro-2H-1-benzopyran
8) (2S,3R,4S)-6-nitro-4-[N-benzyl-N-(2-methyl-2H-tetrazol-5-ylmethyl)amino]-3-hydroxy-2-methyl-2-dimethoxymethyl-3,4-dihydro-2H-1-benzopyran
9) (2S,3S,4R)-6-nitro-4-[N-(4-nitrophenyl)-N-(2-methyl-2H-tetrazol-5-ylmethyl)amino]-3-hydroxy-2-methyl-2-dimethoxymethyl-3,4-dihydro-2H-1-benzopyran
10) (2S,3S,4R)-6-amino-4-[N-(4-chlorophenyl)-N-(2-methyl-2H-tetrazol-5-ylmethyl)amino]-3-hydroxy-2-methyl-2-dimethoxymethyl-3,4-dihydro-2H-1-benzopyran
11) (2S,3R,4S)-6-amino-4-[N-(4-chlorophenyl)-N-(2-methyl-2H-tetrazol-5-ylmethyl)amino]-3-hydroxy-2-methyl-2-dimethoxymethyl-3,4-dihydro-2H-1-benzopyran
12) (2S,3S,4R)-6-nitro-4-[N-(4-chlorophenyl)-N-(1-methyl-1H-tetrazol-5-ylmethyl)amino]-3-hydroxy-2-methyl-2-dimethoxymethyl-3,4-dihydro-2H-1-benzopyran
13) (2S,3S,4R)-6-nitro-4-[N-(1-methyl-1H-tetrazol-5-ylmethyl)phenylamino]-3-hydroxy-2-methyl-2-dimethoxymethyl-3,4-dihydro-2H-1-benzopyran
14) (2S,3S,4R)-6-nitro-4-[N-(4-fluorophenyl)-N-(1methyl-1H-tetrazol-5-ylmethyl)amino]-3-hydroxy-2-methyl-2-dimethoxymethyl-3,4-dihydro-2H-1-benzopyran
15) (2S,3S,4R)-6-nitro-4-[N-benzyl-N-(1-methyl-1H-tetrazol-5-ylmethyl)amino]-3-hydroxy-2-methyl-2-dimethoxymethyl-3,4-dihydro-2H-1-benzopyran
16) (2S,3R,4S)-6-nitro-4-[N-benzyl-N-(1-methyl-1H-tetrazol-5-ylmethyl)amino]-3-hydroxy-2-methyl-2-dimethoxymethyl-3,4-dihydro-2H-1-benzopyran
17) (2S,3S,4R)-6-amino-4-[N-(4-chlorophenyl)-N-(1-methyl-1H-tetrazol-5-ylmethyl)amino]-3-hydroxy-2-methyl-2-dimethoxymethyl-3,4-dihydro-2H-1-benzopyran
18) (2S,3S,4R)-6-nitro-4-[N-(4-chlorophenyl)-N-(1H-tetrazol-5-ylmethyl)amino]-3-hydroxy-2-methyl-2-dimethoxymethyl-3,4-dihydro-2H-1-benzopyran
19) (2S,3S,4R)-6-nitro-4-[N-(1H-tetrazol-5-ylmethyl)phenylamino]-3-hydroxy-2-methyl-2-dimethoxymethyl-3,4-dihydro-2H-1-benzopyran
20) (2S,3S,4R)-6-nitro-4-[N-benzyl-N-(1H-tetrazol-5-ylmethyl)amino]-3-hydroxy-2-methyl-2-dimethoxymethyl-3,4-dihydro-2H-1-benzopyran
21) (2S,3S,4R)-6-nitro-4[N-(3-chlorophenyl)-N-(2-methyl-2H-tetrazol-5-ylmethyl)amino]-3-hydroxy-2-methyl-2-dimethoxymethyl-3,4-dihydro-2H-1-benzopyran
22) (2S,3S,4R)-6-amino-4-[N-(3-chlorophenyl)-N-(2methyl-2H-tetrazol-5-ylmethyl)amino]-3-hydroxy-2-methyl-2-dimethoxymethyl-3,4-dihydro-2H-1-benzopyran
23) (2S,3S,4R)-6-nitro-4-[N-(4-methylphenyl)-N-(2-methyl-2H-tetrazol-5-ylmethyl)amino]-3-hydroxy-2-methyl-2-S dimethoxymethyl-3,4-dihydro-2H-1-benzopyran
24) (2S,3S,4R)-6-amino-4-[N-(4-methylphenyl)-N-(2-methyl-2H-tetrazol-5-ylmethyl)amino]-3-hydroxy-2-methyl-2-dimethoxymethyl-3,4-dihydro-2H-1-benzopyran
25) (2S,3R,4S)-6-nitro-4-[N-(3-chlorophenyl)-N-(2-methyl-2H-tetrazol-5-ylmethyl)amino]-3-hydroxy-2-methyl-2-dimethoxymethyl-3,4-dihydro-2H-1-benzopyran
26) (2S,3R,4S)-6-amino-4-[N-(3-chlorophenyl)-N-(2-methyl-2H-tetrazol-5-ylmethyl)amino]-3-hydroxy-2-methyl-2-dimethoxymethyl-3,4-dihydro-2H-1-benzopyran
27) (2S,3R,4S)-6-nitro-4-[N-(4-methylphenyl)-N-(2-methyl-2H-tetrazol-5-ylmethyl)amino]-3-hydroxy-2-methyl-2-dimethoxymethyl-3,4-dihydro-2H-1-benzopyran
28) (2S,3R,4S)-6-amino-4-[N-(4-methylphenyl)-N-(2-methyl-2H-tetrazol-5-ylmethyl)amino]-3-hydroxy-2-methyl-2-dimethoxymethyl-3,4-dihydro-2H-1-benzopyran
29) (2S,3R,4S)-6-nitro-4-[N-(2-chlorophenyl)-N-(2-methyl-2H-tetrazol-5-ylmethyl)amino]-3-hydroxy-2-methyl-2-dimethoxymethyl-3,4-dihydro-2H-1-benzopyran
30) (2S,3R,4S)-6-amino-4-[N-(2-chlorophenyl)-N-(2methyl-2H-tetrazol-5-ylmethyl)amino]-3-hydroxy-2-methyl-2-dimethoxymethyl-3,4-dihydro-2H-1-benzopyran
31) (2S,3R,4S)-6-nitro-4-[N-(4-trifluoromethoxyphenyl)-N-(2-methyl-2H-tetrazol-5-ylmethyl)amino]-3-hydroxy-2-methyl-2-dimethoxymethyl-3,4-dihydro-2H-1-benzopyran
32) (2S,3R,4S)-6-amino-4-[N-(4-trifluoromethoxyphenyl)-N-(2-methyl-2H-tetrazol-5-ylmethyl)amino]-3-hydroxy-2-methyl-2-dimethoxymethyl-3,4-dihydro-2H-1-benzopyran
33) (2S,3R,4S)-6-nitro-4-[N-(4-trifluoromethylphenyl)-N-(2-methyl-2H-tetrazol-5-ylmethyl)amino]-3-hydroxy-2-methyl-2-dimethoxymethyl-3,4-dihydro-2H-1-benzopyran
34) (2S,3R,4S)-6-amino-4-[N-(4-trifluoromethylphenyl)-N-(2-methyl-2H-tetrazol-5-ylmethyl)amino]-3-hydroxy-2-methyl-2-dimethoxymethyl-3,4-dihydro-2H-1-benzopyran
35) (2S,3R,4S)-6-nitro-4-[N-(3-acetylphenyl)-N-(2-methyl-2H-tetrazol-5-ylmethyl)amino]-3-hydroxy-2-methyl-2-dimethoxymethyl-3,4-dihydro-2H-1-benzopyran
36) (2S,3R,4S)-6-amino-4-[N-[3-(1-hydroxyethyl)phenyl]-N-(2-methyl-2H-tetrazol-5-ylmethyl)amino]-3-hydroxy-2-methyl-2-dimethoxymethyl-3,4-dihydro-2H-1-benzopyran
37) (2S,3R,4S)-6-nitro-4-[N-(2-methyl-4-fluorophenyl)-N-(2-methyl-2H-tetrazol-5-ylmethyl)amino]-3-hydroxy-2-methyl-2-dimethoxymethyl-3,4-dihydro-2H-1-benzopyran
38) (2S,3R,4S)-6-amino-4-[N-(2-methyl-4-fluorophenyl)-N-(2-methyl-2H-tetrazol-5-ylmethyl)amino]-3-hydroxy-2-methyl-2-dimethoxymethyl-3,4-dihydro-2H-1-benzopyran
39) (2S,3R,4S)-6-nitro-4-[N-(4-methoxyphenyl)-N-(2-methyl-2H-tetrazol-5-ylmethyl)amino]-3-hydroxy-2-methyl-2-dimethoxymethyl-3,4-dihydro-2H-1-benzopyran
40) (2S,3R,4S)-6-amino-4-[N-(4-methoxyphenyl)-N-(2-methyl-2H-tetrazol-5-ylmethyl)amino]-3-hydroxy-2-methyl-2-dimethoxymethyl-3,4-dihydro-2H-1-benzopyran
41) (2S,3R,4S)-6-nitro-4-[N-(2-methyl-4-chlorophenyl)-N-(2-methyl-2H-tetrazol-5-ylmethyl)amino]-3-hydroxy-2-methyl-2-dimethoxymethyl-3,4-dihydro-2H-1-benzopyran 42) (2S,3R,4S)-6-amino-4-[N-(2-methyl-4-chlorophenyl)-N-(2-methyl-2H-tetrazol-5-ylmethyl)amino]-3-hydroxy-2-methyl-2-dimethoxymethyl-3,4-dihydro-2H-1-benzopyran 43) (2S,3R,4S)-6-nitro-4-[N-(2-methoxy-5-methylphenyl)-N-(2-methyl-2H-tetrazol-5-ylmethyl)amino]-3-hydroxy-2-methyl-2-dimethoxymethyl-3,4-dihydro-2H-1-benzopyran 44) (2S,3R,4S)-6-amino-4-[N-(2-methoxy-5-methylphenyl)-N-(2-methyl-2H-tetrazol-5-ylmethyl)amino]-3-hydroxy-2-methyl-2-dimethoxymethyl-3,4-dihydro-2H-1-benzopyran 45) (2S,3R,4S)-6-nitro-4-[N-(2,4-dimethylphenyl)-N-(2-methyl-2H-tetrazol-5-ylmethyl)amino]-3-hydroxy-2-methyl-2-dimethoxymethyl-3,4-dihydro-2H-1-benzopyran 46) (2S,3R,4S)-6-amino-4-[N-(2,4-dimethylphenyl)-N-(2-methyl-2H-tetrazol-5-ylmethyl)amino]-3-hydroxy-2-methyl-2-dimethoxymethyl-3,4-dihydro-2H-1-benzopyran 47) (2S,3R,4S)-6-nitro-4-[N-(2,6-dimethylphenyl)-N-(2-methyl-2H-tetrazol-5-ylmethyl)amino]-3-hydroxy-2-methyl-2-dimethoxymethyl-3,4-dihydro-2H-1-benzopyran 48) (2S,3R,4S)-6-amino-4-[N-(2,6-dimethylphenyl)-N-(2-methyl-2H-tetrazol-5-ylmethyl)amino]-3-hydroxy-2-methyl-2-dimethoxymethyl-3,4-dihydro-2H-1-benzopyran 49) (2S,3R,4S)-6-nitro-4-[N-(2,3-dimethylphenyl)-N-(2-methyl-2H-tetrazol-5-ylmethyl)amino]-3-hydroxy-2-methyl-2-dimethoxymethyl-3,4-dihydro-2H-1-benzopyran 50) (2S,3R,4S)-6-amino-4-[N-(2,3-dimethylphenyl)-N-(2-methyl-2H-tetrazol-5-ylmethyl)amino]-3-hydroxy-2-methyl-2-dimethoxymethyl-3,4-dihydro-2H-1-benzopyran 51) (2S,3R,4S)-6-nitro-4-[N-(2-isopropylphenyl)-N-(2-methyl-2H-tetrazol-5-ylmethyl)amino]-3-hydroxy-2-methyl-2-dimethoxymethyl-3,4-dihydro-2H-1-benzopyran 52) (2S,3R,4S)-6-amino-4-[N-(2-isopropylphenyl)-N-(2-methyl-2H-tetrazol-5-ylmethyl)amino]-3-hydroxy-2-methyl-2-dimethoxymethyl-3,4-dihydro-2H-1-benzopyran 53) (2S,3R,4S)-6-nitro-4-[N-(4-ethoxycarbonylphenyl)-N-(2-methyl-2H-tetrazol-5-ylmethyl)amino]-3-hydroxy-2-methyl-2-dimethoxymethyl-3,4-dihydro-2H-1-benzopyran 54) (2S,3R,4S)-6-amino-4-[N-(4-ethoxycarbonylphenyl)-N-(2-methyl-2H-tetrazol-5-ylmethyl)amino]-3-hydroxy-2-methyl-2-dimethoxymethyl-3,4-dihydro-2H-1-benzopyran 55) (2S,3R,4S)-6-amino-4-[N-(2-methyl-2H-tetrazol-5-ylmethyl)phenylamino]-3-hydroxy-2-methyl-2-dimethoxymethyl-3,4-dihydro-2H-1-benzopyran 56) (2S,3R,4S)-6-amino-4-[N-(4-fluorophenyl)-N-(2-methyl-2H-tetrazol-5-ylmethyl)amino]-3-hydroxy-2-methyl-2-dimethoxymethyl-3,4-dihydro-2H-1-benzopyran 57) (2S,3R,4S)-6-amino-4-[N-benzyl-N-(2-methyl-2H-tetrazol-5-ylmethyl)amino]-3-hydroxy-2-methyl-2-dimethoxymethyl-3,4-dihydro-2H-1-benzopyran 58) (2S,3R,4S)-6-nitro-4-[N-[(3-methoxycarbonyl)phenyl]-N-(2-methyl-2H-tetrazol-5-ylmethyl)amino]-3-hydroxy-2-methyl-2-dimethoxymethyl-3,4-dihydro-2H-1-benzopyran 59) (2S,3R,4S)-6-amino-4-[N-[(3-methoxycarbonyl)phenyl]-N-(2-methyl-2H-tetrazol-5-ylmethyl)amino]-3-hydroxy-2-methyl-2-methoxymethyl-3,4-dihydro-2H-1-benzopyran 60) (2S,3R,4S)-6-nitro-4-[N-(2-hydroxyphenyl)-N-(2-methyl-2H-tetrazol-5-ylmethyl)amino]-3-hydroxy-2-methyl-2-dimethoxymethyl-3,4-dihydro-2H-1-benzopyran 61) (2S,3R,4S)-6-amino-4-[N-(2-hydroxyphenyl)-N-(2-methyl-2H-tetrazol-5-ylmethyl)amino]-3-hydroxy-2-methyl-2-dimethoxymethyl-3,4-dihydro-2H-1-benzopyran 62) (2S,3R,4S)-6-nitro-4-[N-[(2-methoxy-4-methoxycarbonyl)phenyl]-N-(2-methyl-2H-tetrazol-5-ylmethyl)amino]-3-hydroxy-2-methyl-2-dimethoxymethyl-3,4-dihydro-2H-1-benzopyran 63) (2S,3R,4S)-6-amino-4-[N-[(2-methoxy-4-methoxycarbonyl)phenyl]-N-(2-methyl-2H-tetrazol-5-ylmethyl)amino]-3-hydroxy-2-methyl-2-dimethoxymethyl-3,4-dihydro-2H-1-benzopyran 64) (2S,3R,4S)-6-nitro-4-[N-[(2-methyl-4-hydroxy)phenyl]-N-(2-methyl-2H-tetrazol-5-ylmethyl)amino]-3-hydroxy-2-methyl-2-dimethoxymethyl-3,4-dihydro-2H-1-benzopyran 65) (2S,3R,4S)-6-amino-4-[N-[(2-methyl-4-hydroxy)phenyl]-N-(2-methyl-2H-tetrazol-5-ylmethyl)amino]-3-hydroxy-2-methyl-2-dimethoxymethyl-3,4-dihydro-2H-1-benzopyran 66) (2S,3R,4S)-6-nitro-4-[N-(2-ethylphenyl)-N-(2-methyl-2H-tetrazol-5-ylmethyl)amino]-3-hydroxy-2-methyl-2-dimethoxymethyl-3,4-dihydro-2H-1-benzopyran 67) (2S,3R,4S)-6-amino-4-[N-(2-ethylphenyl)-N-(2-methyl-2H-tetrazol-5-ylmethyl)amino]-3-hydroxy-2-methyl-2-dimethoxymethyl-3,4-dihydro-2H-1-benzopyran 68) (2S,3R,4S)-6-nitro-4-[N-(2-methyl-5-(methoxycarbonyl)phenyl-N-(2-methyl-2H-tetrazol-5-ylmethyl)amino]-3-hydroxy-2-methyl-2-dimethoxymethyl-3,4-dihydro-2H-1-benzopyran 69) (2S,3R,4S)-6-amino-4-[N-(2-methyl-5-(methoxycarbonyl)phenyl-N-(2-methyl-2H-tetrazol-5-ylmethyl)amino]-3-hydroxy-2-methyl-2-dimethoxymethyl-3,4-dihydro-2H-1-benzopyran 70) (2S,3R,4S)-6-nitro-4-[N-(2-hydroxy-5-methylphenyl)-N-(2-methyl-2H-tetrazol-5-ylmethyl)amino]-3-hydroxy-2-methyl-2-dimethoxymethyl-3,4-dihydro-2H-1-benzopyran 71) (2S,3R,4S)-6-amino-4-[N-(2-hydroxy-5-methylphenyl)-N-(2-methyl-2H-tetrazol-5-ylmethyl)amino]-3-hydroxy-2-methyl-2-dimethoxymethyl-3,4-dihydro-2H-1-benzopyran 72) (2S,3R,4S)-6-nitro-4-[N-(2,4,6-trimethylphenyl)-N-(2-methyl-2H-tetrazol-5-ylmethyl)amino]-3-hydroxy-2-methyl-2-dimethoxymethyl-3,4-dihydro-2H-1-benzopyran 73) (2S,3R,4S)-6-amino-4-[N-(2,4,6-trimethylphenyl)-N-(2-methyl-2H-tetrazol-5-ylmethyl)amino]-3-hydroxy-2-methyl-2-dimethoxymethyl-3,4-dihydro-2H-1-benzopyran 74) (2S,3S,4R)-6-nitro-4-[N-(4-trifluoromethylphenyl)-N-(2-methyl-2H-tetrazol-5-ylmethyl)amino]-3-hydroxy-2-methyl-2-dimethoxymethyl-3,4-dihydro-2H-1-benzopyran 75) (2S,3S,4R)-6-amino-4-[N-(4-trifluoromethylphenyl)-N-(2-methyl-2H-tetrazol-5-ylmethyl)amino]-3-hydroxy-2-methyl-2-dimethoxymethyl-3,4-dihydro-2H-1-benzopyran 76) (2R,3S,4R)-6-nitro-4-[N-(4-trifluoromethylphenyl)-N-(2-methyl-2H-tetrazol-5-ylmethyl)amino]-3-hydroxy-2-methyl-2-dimethoxymethyl-3,4-dihydro-2H-1-benzopyran 77) (2R,3S,4R)-6-amino-4-[N-(4-trifluoromethylphenyl)-N-(2-methyl-2H-tetrazol-5-ylmethyl)amino]-3-hydroxy-2-methyl-2-dimethoxymethyl-3,4-dihydro-2H-1-benzopyran 78) (2R,3R,4S)-6-nitro-4-[N-(4-trifluoromethylphenyl)-N-(2-methyl-2H-tetrazol-5-ylmethyl)amino]-3-hydroxy-2-methyl-2-dimethoxymethyl-3,4-dihydro-2H-1-benzopyran 79) (2R,3R,4S)-6-amino-4-[N-(4-trifluoromethylphenyl)-N-(2-methyl-2H-tetrazol-5-ylmethyl)amino]-3-hydroxy-2-methyl-2-dimethoxymethyl-3,4-dihydro-2H-1-benzopyran
80) (2S,3S,4R)-6-nitro-4-[N-(4-trifluoromethoxyphenyl)-N-(2-methyl-2H-tetrazol-5-ylmethyl)amino]-3-hydroxy-2-methyl-2-dimethoxymethyl-3,4-dihydro-2H-1-benzopyran
81) (2S,3S,4R)-6-amino-4-[N-(4-trifluoromethoxyphenyl)-N-(2-methyl-2H-tetrazol-5-ylmethyl)amino]-3-hydroxy-2-methyl-2-dimethoxymethyl-3,4-dihydro-2H-1-benzopyran
82) (2R,3R,4S)-6-nitro-4-[N-(4-trifluoromethoxyphenyl)-N-(2-methyl-2H-tetrazol-5-ylmethyl)amino]-3-hydroxy-2-methyl-2-dimethoxymethyl-3,4-dihydro-2H-1-benzopyran
83) (2R,3R,4S)-6-amino-4-[N-(4-trifluoromethoxyphenyl)-N-(2-methyl-2H-tetrazol-5-ylmethyl)amino]-3-hydroxy-2-methyl-2-dimethoxymethyl-3,4-dihydro-2H-1-benzopyran
84) (2R,3S,4R)-6-nitro-4-[N-(4-trifluoromethoxyphenyl)-N-(2-methyl-2H-tetrazol-5-ylmethyl)amino]-3-hydroxy-2-methyl-2-dimethoxymethyl-3,4-dihydro-2H-1-benzopyran
85) (2R,3S,4R)-6-amino-4-[N-(4-trifluoromethoxyphenyl)-N-(2-methyl-2H-tetrazol-5-ylmethyl)amino]-3-hydroxy-2-methyl-2-dimethoxymethyl-3,4-dihydro-2H-1-benzopyran
86) (2S,3S,4R)-6-nitro-4-[N-(4-chlorophenyl)-N-(2-methyl-2H-tetrazol-5-ylmethyl)amino]-3-acetoxy-2-methyl-2-dimethoxymethyl-3,4-dihydro-2H-1-benzopyran
87) (2S,3S,4R)-6-acetamino-4-[N-(4-chlorophenyl)-N-(2-methyl-2H-tetrazol-5-ylmethyl)amino]-3-acetoxy-2-methyl-2-dimethoxymethyl-3,4-dihydro-2H-1-benzopyran
88) (2S,3S,4R)-6-acetamino-4-[N-(4-chlorophenyl)-N-(2-methyl-2H-tetrazol-5-ylmethyl)amino]-3-hydroxy-2-methyl-2-dimethoxymethyl-3,4-dihydro-2H-1-benzopyran
89) (2S,3S,4R)-6-amino-4-[N-(4-chlorophenyl)-N-(2-methyl-2H-tetrazol-5-ylmethyl)amino]-3-acetoxy-2-methyl-2-dimethoxymethyl-3,4-dihydro-2H-1-benzopyran
90) (2S,3R,4S)-6-bromo-4-[N-(4-chlorophenyl)-N-(2-methyl-2H-tetrazol-5-ylmethyl)amino]-3-hydroxy-2-methyl-2-dimethoxymethyl-3,4-dihydro-2H-1-benzopyran
91) (2R,3R,4S)-6-bromo-4-[N-(4-chlorophenyl)-N-(2-methyl-2H-tetrazol-5-ylmethyl)amino]-3-hydroxy-2-methyl-2-dimethoxymethyl-3,4-dihydro-2H-1-benzopyran
92) (2S,3R,4S)-6-bromo-4-[N-(4-fluorophenyl)-N-(2-methyl-2H-tetrazol-5-ylmethyl)amino]-3-hydroxy-2-methyl-2-dimethoxymethyl-3,4-dihydro-2H-1-benzopyran
93) (2R,3R,4S)-6-bromo-4-[N-(4-fluorophenyl)-N-(2-methyl-2H-tetrazol-5-ylmethyl)amino]-3-hydroxy-2-methyl-2-dimethoxymethyl-3,4-dihydro-2H-1-benzopyran
94) (2R,3R,4S)-6-bromo-4-[N-(2-methyl-2H-tetrazol-5-ylmethyl)phenylamino]-3-hydroxy-2-methyl-2-dimethoxymethyl-3,4-dihydro-2H-1-benzopyran
95) (2R,3S,4R)-6-methanesulfonyloxy-4-[N-(4-chlorophenyl)-N-(2-methyl-2H-tetrazol-5-ylmethyl)amino]-3-hydroxy-2-methyl-2-dimethoxymethyl-3,4-dihydro-2H-1-benzopyran
96) (2S,3S,4R)-6-methanesulfonyloxy-4-[N-(4-chlorophenyl)-N-(2-methyl-2H-tetrazol-5-ylmethyl)amino]-3-hydroxy-2-methyl-2-dimethoxymethyl-3,4-dihydro-2H-1-benzopyran
97) (2S,3S,4R)-6-hydroxy-4-[N-(4-chlorophenyl)-N-(2-methyl-2H-tetrazol-5-ylmethyl)amino]-3-hydroxy-2-methyl-2-dimethoxymethyl-3,4-dihydro-2H-1-benzopyran
98) (2S,3S,4R)-6-nitro-5-methyl-4-[N-(4-chlorophenyl)-N-(2-methyl-2H-tetrazol-5-ylmethyl)amino]-3-hydroxy-2-methyl-2-dimethoxymethyl-3,4-dihydro-2H-1-benzopyran
99) (2S,3S,4R)-6-nitro-4-[N-(4-fluorophenyl)-N-(2-methyl-2H-tetrazol-5-ylmethyl)amino]-3-hydroxy-2-methyl-2methoxymethyl-3,4-dihydro-2H-1-benzopyran
100) (3R,4S)-6-cyano-4-[N-(4-chlorophenyl)-N-(2-methyl-2H-tetrazol-5-ylmethyl)amino]-3-hydroxy-2,2-dimethyl-3,4-dihydro-2H-1-benzopyran
101) (3R,4S)-6-cyano-4-[N-(2-methyl-2H-tetrazol-5-ylmethyl)phenylamino]-3-hydroxy-2,2-dimethyl-3,4-dihydro-2H-1-benzopyran
102) (2S,3S,4R)-6-hydroxy-4-[N-(4-chlorophenyl)-N-(2-methyl-2H-tetrazol-5-ylmethyl)amino]-3-hydroxy-2-methyl-2-dimethoxymethyl-3,4-dihydro-2H-1-benzopyran
103) (2S,3S,4R)-8-nitro-4-[N-(4-chlorophenyl)-N-(2-methyl-2H-tetrazol-5-ylmethyl)amino]-3-hydroxy-2-methyl-2-dimethoxymethyl-3,4-dihydro-2H-1-benzopyran
104) (2S,3S,4R)-8-amino-4-[N-(4-chlorophenyl)-N-(2-methyl-2H-tetrazol-5-ylmethyl)amino]-3-hydroxy-2-methyl-2-dimethoxymethyl-3,4-dihydro-2H-1-benzopyran
105) (2R,3S,4R)-8-nitro-4-[N-(4-chlorophenyl)-N-(2-methyl-2H-tetrazol-5-ylmethyl)amino]-3-hydroxy-2-methyl-2-dimethoxymethyl-3,4-dihydro-2H-1-benzopyran
106) (2R,3S,4R)-8-amino-4-[N-(4-chlorophenyl)-N-(2-methyl-2H-tetrazol-5-ylmethyl)amino]-3-hydroxy-2-methyl-2-dimethoxymethyl-3,4-dihydro-2H-1-benzopyran
107) (2R,3R,4S)-6-nitro-4-[N-(4-chlorophenyl)-N-(2-methyl-2H-tetrazol-5-ylmethyl)amino]-3-hydroxy-2-methyl-2-dimethoxymethyl-3,4-dihydro-2H-1-benzopyran
108) (2R,3R,4S)-6-amino-4-[N-(4-chlorophenyl)-N-(2-methyl-2H-tetrazol-5-ylmethyl)amino]-3-hydroxy-2-methyl-2-dimethoxymethyl-3,4-dihydro-2H-1-benzopyran
109) (2R,3S,4R)-6-nitro-4-[N-(4-chlorophenyl)-N-(2-methyl-2H-tetrazol-5-ylmethyl)amino]-3-hydroxy-2-methyl-2-dimethoxymethyl-3,4-dihydro-2H-1-benzopyran
110) (2R,3S,4R)-6-amino-4-[N-(4-chlorophenyl)-N-(2-methyl-2H-tetrazol-5-ylmethyl)amino]-3-hydroxy-2-methyl-2-dimethoxymethyl-3,4-dihydro-2H-1-benzopyran
111) (2S,3R,4R)-6-nitro-4-[N-(4-chlorophenyl)-N-(2-methyl-2H-tetrazol-5-ylmethyl)amino]-3-hydroxy-2-methyl-2-dimethoxymethyl-3,4-dihydro-2H-1-benzopyran
112) (2S,3R,4R)-6-amino-4-[N-(4-chlorophenyl)-N-(2-methyl-2H-tetrazol-5-ylmethyl)amino]-3-hydroxy-2-methyl-2-dimethoxymethyl-3,4-dihydro-2H-1-benzopyran
113) (2S,3S,4S)-6-nitro-4-[N-(4-chlorophenyl)-N-(2-methyl-2H-tetrazol-5-ylmethyl)amino]-3-hydroxy-2-methyl-2-dimethoxymethyl-3,4-dihydro-2H-1-benzopyran
114) (2S,3S,4S)-6-amino-4-[N-(4-chlorophenyl)-N-(2-methyl-2H-tetrazol-5-ylmethyl)amino]-3-hydroxy-2-methyl-2-dimethoxymethyl-3,4-dihydro-2H-1-benzopyran
115) (2R,3R,4R)-6-nitro-4-[N-(4-chlorophenyl)-N-(2-methyl-2H-tetrazol-5-ylmethyl)amino]-3-hydroxy-2-methyl-2dimethoxymethyl-3,4-dihydro-2H-1-benzopyran
116) (2R,3R,4R)-6-amino-4-[N-(4-chlorophenyl)-N-(2-methyl-2H-tetrazol-5-ylmethyl)amino]-3-hydroxy-2-methyl-2-dimethoxymethyl-3,4-dihydro-2H-1-benzopyran
117) (2R,3S,4S)-6-nitro-4-[N-(4-chlorophenyl)-N-(2-methyl-2H-tetrazol-5-ylmethyl)amino]-3-hydroxy-2-methyl-2-dimethoxymethyl-3,4-dihydro-2H-1-benzopyran
118) (2R,3S,4S)-6-amino-4-[N-(4-chlorophenyl)-N-(2-methyl-2H-tetrazol-5-ylmethyl)amino]-3-hydroxy-2-methyl-2-dimethoxymethyl-3,4-dihydro-2H-1-benzopyran.

More preferably, the compounds of formula 1 comprise:
1) (2S,3S,4R)-6-nitro-4-[N-(4-chlorophenyl)-N-(2-methyl-2H-tetrazol-5-ylmethyl)amino]-3-hydroxy-2-methyl-2-dimethoxymethyl-3,4-dihydro-2H-1-benzopyran;
10) (2S,3S,4R)-6-amino-4-[N-(4-chlorophenyl)-N-(2-methyl-2H-tetrazol-5-ylmethyl)amino]-3-hydroxy-2-methyl-2-dimethoxymethyl-3,4-dihydro-2H-1-benzopyran;
11) (2S,3R,4S)-6-amino-4-[N-(4-chlorophenyl)-N-(2-methyl-2H-tetrazol-5-ylmethyl)amino]-3-hydroxy-2-methyl-2-dimethoxymethyl-3,4-dihydro-2H-1-benzopyran;
17) (2S,3S,4R)-6-amino-4-[N-(4-chlorophenyl)-N-(1-methyl-1H-tetrazol-5-ylmethyl)amino]-3-hydroxy-2-methyl-2-dimethoxymethyl-3,4-dihydro-2H-1-benzopyran;
22) (2S,3S,4R)-6-amino-4-[N-(3-chlorophenyl)-N-(2-methyl-2H-tetrazol-5-ylmethyl)amino]-3-hydroxy-2-methyl-2-dimethoxymethyl-3,4-dihydro-2H-1-benzopyran;
24) (2S,3S,4R)-6-amino-4-[N-(4-methylphenyl)-N-(2-methyl-2H-tetrazol-5-ylmethyl)amino]-3-hydroxy-2-methyl-2-dimethoxymethyl-3,4-dihydro-2H-1-benzopyran;
26) (2S,3R,4S)-6-amino-4-[N-(3-chlorophenyl)-N-(2-methyl-2H-tetrazol-5-ylmethyl)amino]-3-hydroxy-2-methyl-2-dimethoxymethyl-3,4-dihydro-2H-1-benzopyran;
28) (2S,3R,4S)-6-amino-4-[N-(4-methylphenyl)-N-(2-methyl-2H-tetrazol-5-ylmethyl)amino]-3-hydroxy-2-methyl-2-dimethoxymethyl-3,4-dihydro-2H-1-benzopyran;
30) (2S,3R,4S)-6-amino-4-[N-(2-chlorophenyl)-N-(2-methyl-2H-tetrazol-5-ylmethyl)amino]-3-hydroxy-2-methyl-2-dimethoxymethyl-3,4-dihydro-2H-1-benzopyran;
32) (2S,3R,4S)-6-amino-4-[N-(4-trifluoromethoxyphenyl)-N-(2-methyl-2H-tetrazol-5-ylmethyl)amino]-3-hydroxy-2-methyl-2-dimethoxymethyl-3,4-dihydro-2H-1-benzopyran;
34) (2S,3R,4S)-6-amino-4-[N-(4-trifluoromethylphenyl)-N-(2-methyl-2H-tetrazol-5-ylmethyl)amino]-3-hydroxy-2-methyl-2-dimethoxymethyl-3,4-dihydro-2H-1-benzopyran;
42) (2S,3R,4S)-6-amino-4-[N-(2-methyl-4-chlorophenyl)-N-(2-methyl-2H-tetrazol-5-ylmethyl)amino]-3-hydroxy-2-methyl-2-dimethoxymethyl-3,4-dihydro-2H-1-benzopyran;
52) (2S,3R,4S)-6-amino-4-[N-(2-isopropylphenyl)-N-(2-methyl-2H-tetrazol-5-ylmethyl)amino]-3-hydroxy-2-methyl-2-dimethoxymethyl-3,4-dihydro-2H-1-benzopyran;
54) (2S,3R,4S)-6-amino-4-[N-[4-(ethoxycarbonyl)phenyl]-N-(2-methyl-2H-tetrazol-5-ylmethyl)amino]-3-hydroxy-2-methyl-2-dimethoxymethyl-3,4-dihydro-2H-1-benzopyran;
55) (2S,3R,4S)-6-amino-4-[N-(2-methyl-2H-tetrazol-5-ylmethyl)phenylamino]-3-hydroxy-2-methyl-2-dimethoxymethyl-3,4-dihydro-2H-1-benzopyran;
56) (2S,3R,4S)-6-amino-4-[N-(4-fluorophenyl)-N-(2-methyl-2H-tetrazol-5-ylmethyl)amino]-3-hydroxy-2-methyl-2-dimethoxymethyl-3,4-dihydro-2H-1-benzopyran;
57) (2S,3R,4S)-6-amino-4-[N-benzyl-N-(2-methyl-2H-tetrazol-5-ylmethyl)amino]-3-hydroxy-2-methyl-2-dimethoxymethyl-3,4-dihydro-2H-1-benzopyran;
59) (2S,3R,4S)-6-amino-4-[N-[(3-methoxycarbonyl)phenyl]-N-(2-methyl-2H-tetrazol-5-ylmethyl)amino]-3-hydroxy-2-methyl-2-methoxymethyl-3,4-dihydro-2H-1-benzopyran;
60) (2S,3R,4S)-6-nitro-4-[N-(2-hydroxyphenyl)-N-(2-methyl-2H-tetrazol-5-ylmethyl)amino]-3-hydroxy-2-methyl-2-dimethoxymethyl-3,4-dihydro-2H-1-benzopyran;
61) (2S,3R,4S)-6-amino-4-[N-(2-hydroxyphenyl)-N-(2-methyl-2H-tetrazol-5-ylmethyl)amino]-3-hydroxy-2-methyl-2-dimethoxymethyl-3,4-dihydro-2H-1-benzopyran;
70) (2S,3R,4S)-6-nitro-4-[N-(2-hydroxy-5-methylphenyl)-N-(2-methyl-2H-tetrazol-5-ylmethyl)amino]-3-hydroxy-2-methyl-2-dimethoxymethyl-3,4-dihydro-2H-1-benzopyran;
75) (2S,3S,4R)-6-amino-4-[N-(4-trifluoromethylphenyl)-N-(2-methyl-2H-tetrazol-5-ylmethyl)amino]-3-hydroxy-2-methyl-2-dimethoxymethyl-3,4-dihydro-2H-1-benzopyran;
77) (2R,3S,4R)-6-amino-4-[N-(4-trifluoromethylphenyl)-N-(2-methyl-2H-tetrazol-5-ylmethyl)amino]-3-hydroxy-2-methyl-2-dimethoxymethyl-3,4-dihydro-2H-1-benzopyran;
79) (2R,3R,4S)-6-amino-4-[N-(4-trifluoromethylphenyl)-N-(2-methyl-2H-tetrazol-5-ylmethyl)amino]-3-hydroxy-2-methyl-2-dimethoxymethyl-3,4-dihydro-2H-1-benzopyran;
81) (2S,3S,4R)-6-amino-4-[N-(4-trifluoromethoxyphenyl)-N-(2-methyl-2H-tetrazol-5-ylmethyl)amino]-3-hydroxy-2-methyl-2-dimethoxymethyl-3,4-dihydro-2H-1-benzopyran;
83) (2R,3R,4S)-6-amino-4-[N-(4-trifluoromethoxyphenyl)-N-(2-methyl-2H-tetrazol-5-ylmethyl)amino]-3-hydroxy-2-methyl-2-dimethoxymethyl-3,4-dihydro-2H-1-benzopyran;
85) (2R,3S,4R)-6-amino-4-[N-(4-trifluoromethoxyphenyl)-N-(2-methyl-2H-tetrazol-5-ylmethyl)amino]-3-hydroxy-2-methyl-2-dimethoxymethyl-3,4-dihydro-2H-1-benzopyran;
89) (2S,3S,4R)-6-amino-4-[N-(4-chlorophenyl)-N-(2-methyl-2H-tetrazol-5-ylmethyl)amino]-3-acetoxy-2-methyl-2-dimethoxymethyl-3,4-dihydro-2H-1-benzopyran;
107) (2R,3R,4S)-6-nitro-4-[N-(4-chlorophenyl)-N-(2-methyl-2H-tetrazol-5-ylmethyl)amino]-3-hydroxy-2-methyl-2-dimethoxymethyl-3,4-dihydro-2H-1-benzopyran;
108) (2R,3R,4S)-6-amino-4-[N-(4-chlorophenyl)-N-(2-methyl-2H-tetrazol-5-ylmethyl)amino]-3-hydroxy-2-methyl-2-dimethoxymethyl-3,4-dihydro-2H-1-benzopyran;
109) (2R,3S,4R)-6-nitro-4-[N-(4-chlorophenyl)-N-(2-methyl-2H-tetrazol-5-ylmethyl)amino]-3-hydroxy-2-methyl-2-dimethoxymethyl-3,4-dihydro-2H-1-benzopyran
110) (2R,3S,4R)-6-amino-4-[N-(4-chlorophenyl)-N-(2-methyl-2H-tetrazol-5-ylmethyl)amino]-3-hydroxy-2-methyl-2-dimethoxymethyl-3,4-dihydro-2H-1-benzopyran;
111) (2S,3R,4R)-6-nitro-4-[N-(4-chlorophenyl)-N-(2-methyl-2H-tetrazol-5-ylmethyl)amino]-3-hydroxy-2-methyl-2-dimethoxymethyl-3,4-dihydro-2H-1-benzopyran;
112) (2S,3R,4R)-6-amino-4-[N-(4-chlorophenyl)-N-(2-methyl-2H-tetrazol-5-ylmethyl)amino]-3-hydroxy-2-methyl-2-dimethoxymethyl-3,4-dihydro-2H-1-benzopyran;
113) (2S,3S,4S)-6-nitro-4-[N-(4-chlorophenyl)-N-(2-methyl-2H-tetrazol-5-ylmethyl)amino]-3-hydroxy-2-methyl-2-dimethoxymethyl-3,4-dihydro-2H-1-benzopyran;
114) (2S,3S,4S)-6-amino-4-[N-(4-chlorophenyl)-N-(2-methyl-2H-tetrazol-5-ylmethyl)amino]-3-hydroxy-2-methyl-2dimethoxymethyl-3,4-dihydro-2H-1-benzopyran;
115) (2R,3R,4R)-6-nitro-4-[N-(4-chlorophenyl)-N-(2-methyl-2H-tetrazol-5-ylmethyl)amino]-3-hydroxy-2-methyl-2-dimethoxymethyl-3,4-dihydro-2H-1-benzopyran;
116) (2R,3R,4R)-6-amino-4-[N-(4-chlorophenyl)-N-(2-methyl-2H-tetrazol-5-ylmethyl)amino]-3-hydroxy-2-methyl-2-dimethoxymethyl-3,4-dihydro-2H-1-benzopyran;
117) (2R,3S,4S)-6-nitro-4-[N-(4-chlorophenyl)-N-(2-methyl-2H-tetrazol-5-ylmethyl)amino]-3-hydroxy-2-methyl-2-dimethoxymethyl-3,4-dihydro-2H-1-benzopyran;
118) (2R,3S,4S)-6-amino-4-[N-(4-chlorophenyl)-N-(2-methyl-2H-tetrazol-5-ylmethyl)amino]-3-hydroxy-2-methyl-2-dimethoxymethyl-3,4-dihydro-2H-1-benzopyran.

As for the pharmaceutically acceptable salt, it is preferably an acid addition salt prepared by use of a pharmaceutically acceptable free acid. Whether it is inorganic or organic, a free acid can be used if it is pharmaceutically acceptable. Examples of the inorganic free acid include hydrochloric acid, hydrobromic acid, sulfuric acid, and phosphoric acid. Available organic free acids are exemplified by citric acid, acetic acid, lactic acid, tartaric acid, malic acid, fumaric acid, formic acid, propionic acid, oxalic acid, trifluoroacetic acid, benzoic acid, gluconic acid, methanesulfonic acid, glycolic acid, succinic acid, 4-toluenesulfonic acid, galacturonic acid, embonic acid, glutamic acid and aspartic acid.

The acid salts of the compounds according to the present invention can be prepared in the customary manner, for example by dissolving the compound of formula 1 in excess aqueous acid and precipitating the salt with a water-miscible organic solvent, such as methanol, ethanol, acetone or acetonitrile. It is also possible to prepare by heating equivalent amounts of the compound of formula 1 and an acid in water or an alcohol, such as glycol monomethyl ether, and then evaporating the mixture to dryness or filtering off the precipitated salt with suction.

Also, the compounds of formula 1 may be in the form of pharmaceutically acceptable alkali metals or alkaline earth metal salts. The alkali metal or alkaline earth metal salts of the compounds of formula 1 can be obtained, for example, by dissolving the compound of formula 1 in excess alkali metal or alkaline earth metal hydroxide solution, filtering off the undissolved materials and evaporating the filerate to dryness.

Sodium, potassium or calcium salts are pharmaceutically suitable. The corresponding silver salts are obtained by the reaction of an alkali metal or alkaline earth metal salt with a suitable silver salt, such as silver nitrate.

In accordance with another aspect of the present invention, it provides a method for preparing the benzopyran compound substituted with tetrazole of formula 1, as represented by following chemical scheme 1.

More particularly, the present invention provides comprising the step of reacting epoxide compound of formula 2 with secondary amine compounds including heterocycle of formula 3 in the presence of metal salt to obtain the compound, wherein $R_3$ is OH group, of formula 1a. Also, the present invention provides further comprising the step of reacting the compound of formula 1a by chemical scheme 2 to obtain the compound of formula 1, which applied to a variety of substituents at $R_3$.

CHEMICAL SCHEME 1

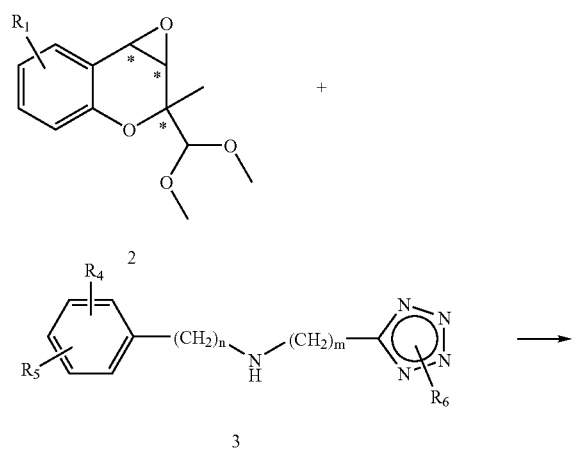

CHEMICAL SCHEME 2

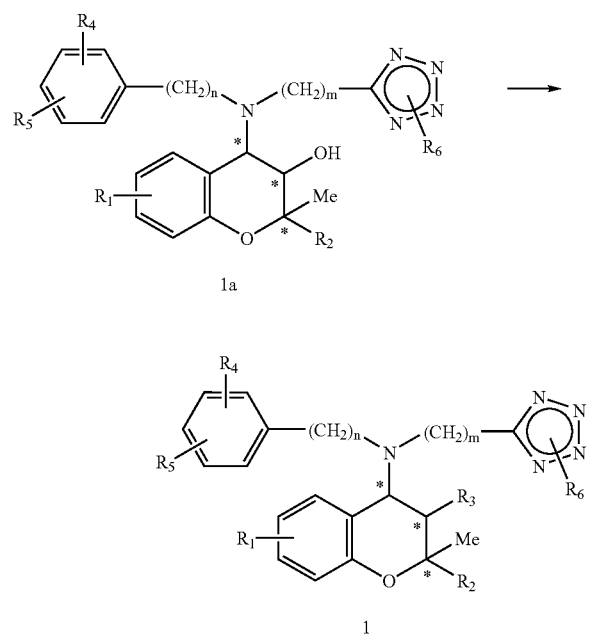

Wherein, $R_1$, $R_2$, $R_3$, $R_4$, $R_5$, $R_6$, n, m and * are same as defined in the above.

In the chemical scheme 1, the metal salt is selected from the group consisting of $Mg(ClO_4)_2$, $CoCl_2$, $LiClO_4$, $NaClO_4$, $CaCl_2$, $ZnCl_2$, $LiBF_4$ and $Zn(Tf)_2$.

The solvent is selected from the group consisting of acetonitrile, tetrahydrofuran and dimethylformamide, preferably acetonitrile.

The reaction condition can be modified in accordance with the species of substituents $R_1$, $R_2$, $R_3$, $R_4$, $R_5$, and $R_6$, preparation, reaction reagent. Reaction temperature may range from room temperature to boiling point of employed solvent.

Also, the substituents $R_1$, $R_2$, $R_3$, $R_4$, $R_5$ and $R_6$ can be modified through the chemical scheme 2, and stereochemistry of 3-carbon position can be determined via the reaction represented by the chemical scheme 1.

The epoxide compounds of formula 2 can be prepared by the preparation method disclosed in U.S. Pat. No. 5,236,935 and KR Pat. No. 094,546, which were acquired by the present inventors (Chemical scheme 3).

CHEMICAL SCHEME 3

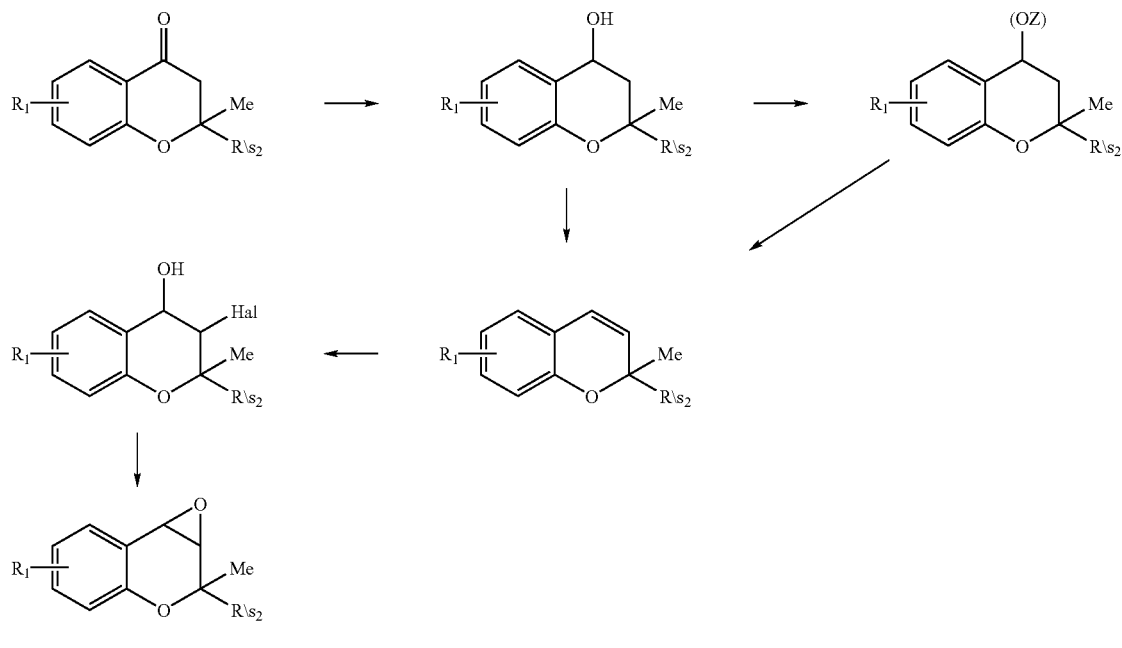

Wherein, $R_1$ and $R_2$ are as defined in the above, (OZ) represent a leaving group, Hal is halogen atom.

Also, the olefin compound of formula 2 can be prepared by the method disclosed in KR Pat. No. 0192083 according to the present inventors, and the stereoisomer can be seperated by common chiral column chromatography or recrystallization.

The epoxide compounds of formulas 2a-2d can be separated to each stereoisomer, all the seperated epoxide compounds or the mixture thereof can be used in the next step.

In case of using a racemic mixture of formula 2 as a synthetic intermediate, the compounds of formula 1, are prepared as a racemic or a diastereomeric mixture, which can be separated into each stereoisomer.

More particularly, the compounds of formula 1, which have original properties of stereochemistry of starting materials, can be prepared by each stereoisomer of epoxide compound, represented as formula 2a to formula 2d.

FORMULA 2a

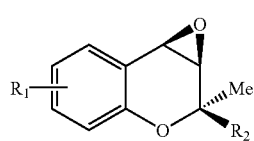

FORMULA 2b

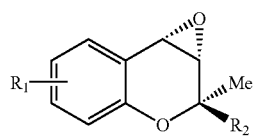

FORMULA 2c

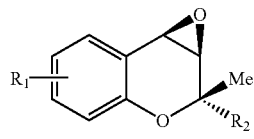

-continued

FORMULA 2d

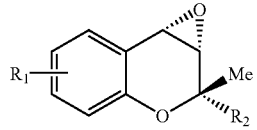

Wherein, $R_1$ and $R_2$ are same as defined in the above.

It is also possible to prepare stereoisomers of epoxide compounds of formula 2, repectively, from olefin compounds by using Mn(III) salen epoxidation catalysts [E. N. Jacobsen et al., *Tetrahedron Lett.* 1991, 38, 5055].

The secondary amine compounds including tetrazole disclosed in the chemical scheme 1, as an other starting material, can be prepared by the method of CHEMICAL SCHEME 4.

CHEMICAL SCHEME 4

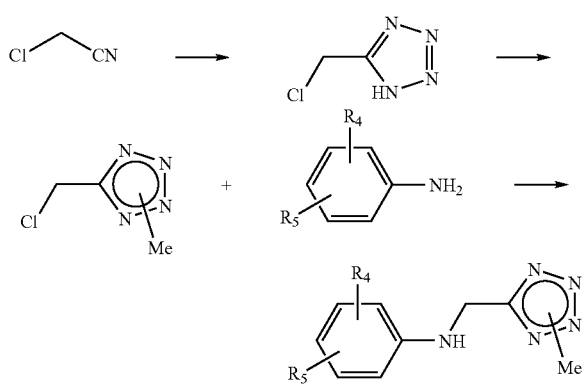

wherein, n is 0, m is 1, $R_6$ is methyl, $R_4$ and $R_5$ are as defined in the above.

In the step 1, the metal azide compound is selected from the group consisting of sodium azide, ammonium azide, trialkylammonium azide, trialkylsillyl azide and trialkyltin azide, preferably sodium azide, ammonium azide.

The reaction solvent is selected from the group consisting of tetrahydrofuran, dimethylformamide, toluene and dimethoxyethane. The reaction temperature may range from room temperature to boiling point of employed solvent.

In the step 3, the base is selected from the group consisting of potassium carbonate, sodium carbonate, sodium hydride and sodium methoxide, and the solvent is selected from the group consisting of ether based solvent such as tetrahydrofuran or dioxane; ketone based solvent such as acetone; and dimethylformamide. The reaction temperature may range from 0° C. to boiling point of employed solvent.

Several processes for the preparation of the compounds of formula 1 according to substituents $R_1$, $R_2$, $R_3$, $R_4$, $R_5$, and $R_6$ are described below in detail. However, the description of the processes, reactants and reaction conditions should not be understood to limit the present invention.

(1) Introduction of Acetoxy at $R_3$

As disclosed in the chemical scheme 5, the compound of formula 1b, introduced acetoxy group at $R_3$-position, can be prepared from reacting of compound of formula 1a, prepared by chemical scheme 1, in the presence of proper solvent and base.

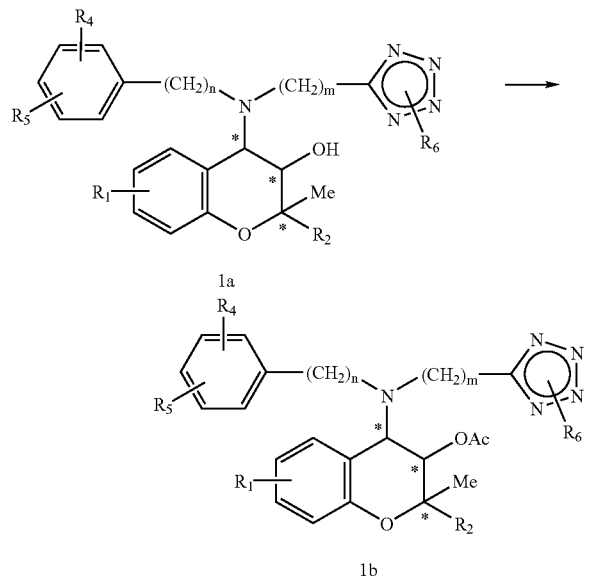

CHEMICAL SCHEME 5 wherein, $R_1$, $R_2$, $R_4$, $R_5$, $R_6$, n, m, and * are as defined in the above.

In the chemical scheme 5, acetyl group can be introduced using a acetic anhydride ($Ac_2O$) or acetyl chloride (AcCl) and all organic or inorganic base can be used as the bases. Preferred organic base is selected from the group consisting of triethylamine, pyridine and N,N-diisopropylethylamine, and preferred inorganic base is selected from the group consisting of sodium carbonate, sodium hydroxide and calcium carbonate. At this time, preferred amount of base is 1 to 3 equivalent related to the compound of formula 1a.

Preferred catalyst is 4-(dimethylamino)pyridine, and preferred amount of catalyst is 0.05 to 0.5 equivalent related to the compound of formula 1a.

The solvent is selected from the group consisting of methylene chloride, chloroform, tetrahydrofuran, acetonitrile. At this time, the reaction temperature may range from 0° C. to 40° C.

(2) Introduction of $NH_2$ at $R_1$

The compound (1d) of formula 1 whose $R_1$ is $NH_2$ can be prepared by the reduction of the compound (1c) whose $R_1$ is $NO_2$ as represented in the below scheme 6.

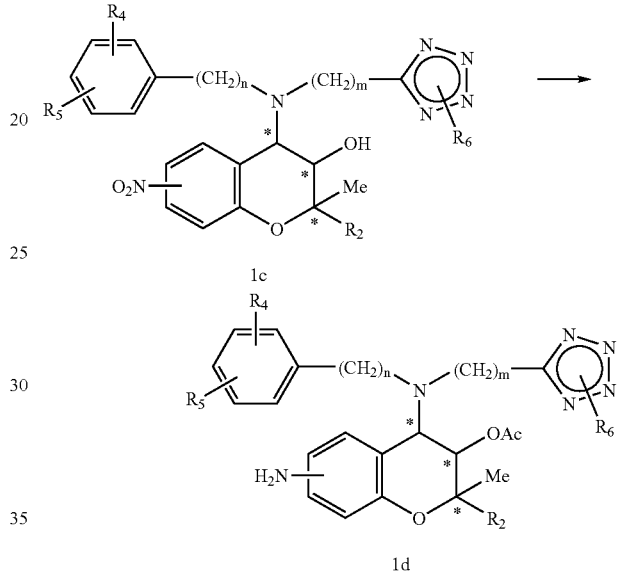

CHEMICAL SCHEME 6 wherein, $R_2$, $R_4$, $R_5$, $R_6$, n, m and * are same as defined in the above.

The $NO_2$ group can be reduced to $NH_2$ group by hydrogenation using metal catalysts such as platinum, palladium on carbon (Pd/C), Raney-nickel, etc. in a suitable solvent. And the reduction reaction is carried by conventional reductants. The solvents are alcohols such as methanol, ethanol, etc. and ethyl acetate.

In addition, the reduction of $NO_2$ group to $NH_2$ group can be carried using a reducing agent such as $NaBH_4$ in the presence of $CuSO_4$, $Cu(OAc)_2$, $CoCl_2$, $SnCl_2$ or $NiCl_2$. At this time, the solvent is a mixture of water and methanol, and room temperature for reaction temperature is preferred.

(3) Introduction of

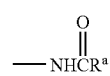

at $R_1$

The compound of formula 1e, whose $R_1$ is $NHC(O)R^a$, can be prepared from reacting of the compound of formula 1d, prepared by chemical scheme 6, with acyl chloride or acid anhydride in the presence of solvent and base.

The base is selected from the group consisting of triethyl amine, N,N-diisopropylethyl amine, pyridine and 4-(dimethylamino)pyridine. The solvent is selected from the group consisting of methylene chloride, chloroform, dimethylsulfoxide, dimethylformamide, teterahydrofuran and dioxane.

(4) Introduction —NHS(O)$_1$R$^a$ at R$_1$

The compound of formula 1f, whose R$_1$ is —NHS(O)$_m$R$^a$ can be prepared from reacting of the compound of formula 1d, prepared by chemical scheme 6, with alkylsufonyl chloride or arylsufonyl chloride in the presence of solvent and base.

At this time, the base is selected from the group consisting of triethyl amine, N,N-diisopropylethyl amine, pyridine and 4-(dimethylamino)pyridine. The solvent is selected from the group consisting of methylene chloride, chloroform, dimethylsulfoxide, dimethylformamide, tetrahydrofuran and dioxane.

In accordance with a further aspect of the present invention, it provides a pharmaceutical composition comprising the benzopyran derivatives substituted with secondary amines including tetrazole of formula 1, their stereoisomers or their pharmaceutically acceptable salts, as an effective ingredient.

More particularly, the present invention provides pharmaceutical composition comprising the benzopyran derivatives substituted with secondary amines including tetrazole, their stereoisomers or their pharmaceutically acceptable salts for protecting neuronal cells, brain injury, heart, retinal ganglion cells, and organs for preservation or during cardiovascular surgery, antioxidation, inhibiting NO generation, or suppressing angiogenesis.

The present invention provides pharmaceutical compositions comprising the benzopyran derivatives substituted with secondary amines including tetrazole, their stereoisomers or their pharmaceutically acceptable salts for protecting neuronal cells.

The compounds (pharmaceutical compositions) of the present invention show neuroprotective effect on protecting neuronal cells from oxidative stress induced cell death by iron or by hydrogen peroxide.

Also the compounds of the present invention protect ischemic-hypoxic and hypoxic brain injury in newborn rats, which are being most frequently used to study infant asphyxia because whose maturity of brain is similar to that of human infant, and it is easy to get enough number of animals required for the determination of effects, by decreasing the ratio of lipid/NAA (N-acetyl aspartate) and lipid/Cr (creatine) in proton MRS (magnetic resonance spectroscopy), which are important index for apoptosis as well as improving morphologic scores and mortality. In addition the compounds of the present invention protect axotomized retinal ganglion cells and represent neuroprotective effects by improving the impaired.

In addition the compounds of the present invention represent neuroprotective effects by improving the impaired nerve conduction velocity in diabetic neuropathy animal model. Therefore, the compounds of the present invention can be used as a neuroprotective and can also be applied for the prevention and treatment of infant asphyxia, glaucoma, diabetic neuropathy, and head trauma caused by neuronal cell damage or death.

In addition, the compounds of the present invention inhibit the lipid peroxidation induced by iron or copper, and suppress intracellular reactive oxygen species in A7r5 (Rat thoracic aorta smooth muscle cell line, ATCC) induced by $H_2O_2$. Hence, the compounds of the present invention can be used as an antioxidant and can be effectively applied for the medical treatment of the neurodegenerative disorders caused by lipid peroxydation and the accumulation of free radical species within neurons, such as aging and senile dementia.

Furthermore, the compounds of the present invention inhibit NO (nitric oxide) formation induced by endotoxins such as lipopolysaccharide (LPS), dose-dependently. Therefore, the compounds of the present invention can be used as inhibitors against NO production and can be effectively applied for the treatment of inflammatory diseases such as arthritis, cardiac infarction, arteriosclerosis, and dementia, which are caused by the injury of tissues or organs as a result of the apoptoic or necroptic cell death due to accumulation of NO within the cells.

Moreover, the compounds of the present invention effectively protect the brain from ischemia-reperfusion injury. Ischemic diseases are occurred by complex interactions between various kinds of neurotransmitters, ion channels, and enzymes, etc. Then, the compounds of the present invention, which have a variety of pharmacological efficacies such as regulation of ion channels, protection of neurotoxicity resulting from iron, hydrogen peroxide, etc., inhibition of lipid peroxidation, and protection of brain injury, etc., are expected to prevent or treat stoke caused by brain ischemia.

In isolated ischemic rat heart model using Langendorff apparatus, the compounds of the present invention significantly prolong the time to contractor (TTC, time to contractor), improve the recovery of postischemic contractile function [LVDP×HR (left ventricular developing pressure)× (heart rat)], and decrease the release of lactate dehydrogenase (LDH) which is a marker enzyme for cell injury, then show similar cardioprotection effect compared to that of BMS-180448. In addition, the compounds of the present invention exhibited equal antiischemic activity compared to that of BMS-180448 in the ischemic myocardium injury models of anesthetized rats. Further, in contrast to BMS-180448, the compounds of the present invention have noticeably low vasorelaxant activity and thus, they are superior to the conventional drugs as cardiac selective cardioprotectants.

As described above, the compounds of the present invention exert excellent anti-ischemic activity both in vivo and in vitro, while show low vasorelaxant acitivity, so that they can be used as cardioprotectives for the prevention and treatment of mayocardial infarction, congestive heart failure, and stenocardia.

Further, the compounds of the present invention suppress angiogenesis dose-dependently in vascular endothelial cell, so that they can be used for suppressing angiogenesis, and prevention and treatment of rheumatic arthritis, psorasis, AIDS complication, cancer or diabetic retinopathy induced by angiogenesis.

The present invention includes pharmaceutical formulations which contain, in addition to non-toxic, inert pharmaceutically suitable additives, one or more than one active ingredients according to the present invention and process for the preparation of these formulations.

Non-toxic inert pharmaceutically suitable vehicles include solid, semi-solid or liquid diluents, fillers and formulation additives of all types.

Preferred pharmaceutical formulations are tablets, coated tablets, capsules, pills, granules, suppositories, solutions, suspensions and emulsions, pastes, ointments, gels, creams, lotions, dusting powders and sprays.

Tablets, coated tablets, capsules, pills and granules can contain the more than one additives in addition to the active ingredient or ingredients, such as (a) fillers and diluents, for example starches, lactose, sucrose, glucose, mannitol and silicic acid, (b) binders, for example carboxymethylcellulose, alginates, gelatine and polyvinylpyrrolidone, (c) humectants, for example glycerol, (d) disintegrants, for example agar-agar, calcium carbonate and sodium carbonate, (e) solution retarders, for example paraffin, and (f) absorption accelerators, for example quaternary ammonium compounds, (g) wetting agents, for example acetyl alcohol and glycerol monostearate, (h) adsorbents, for example kaolin and bentonite, and (i) lubricants, for example talc, calcium stearate, magnesium stearate, and solid polyethylene glycols, or mixtures of the substances listed under (a) to (i).

The tablets, coated tablets, capsules, pills and granules can be provided with the customary coatings and shells, optionally containing opacifying agents, and can also be of a composition such that they release the active ingredient or ingredients only or preferentially in a certain part of the intestinal tract, if appropriate in a delayed manner, examples of embedding compositions which can be used being polymeric substances and waxes.

If appropriate, the active ingredient or ingredients can also be present in microencapsulated form with one or more of the above mentioned excipients.

Suppositories can contain, in addition to the active ingredient or ingredients, the customary water-soluble or water-insoluble excipients, for example polyethylene glycols, fats, for example cacao fat, and higher esters (for example, $C_{14}$-alcohol with $C_{16}$-fatty acid) or mixtures of these substances.

Ointments, pastes, creams and gels can contain, in addition to the active ingredient or ingredients, the customary excipients, for example animal and vegetable fats, waxes, paraffins, starch, tragacanth, cellulose derivatives, polyethylene glycols, silicones, bentonites, silicic acid, talc and zinc oxide, or mixtures of these substances.

Dusting powders and sprays can contain, in addition to the active ingredient or ingredients, the customary excipients, for example lactose, talc, silicic acid, aluminum hydroxide, calcium silicate and polyamide powder, or mixtures of these substances. Sprays can additionally contain the customary propellants, for example chlorofluorohydrocarbons.

Solutions and emulsions can contain, in addition to the active ingredient or ingredients, the customary excipients, such as solvents, solubilizing agents and emulsifiers, for example water, ethyl alcohol, isopropyl alcohol, ethylcarbonate, ethyl acetate, benzyl alcohol, benzyl benzoate, propylene glycol, 1,3-butylene glycol, dimethylformamide, oils, in particular cottonseed oil, groundnut oil, corn germ oil, olive oil, castor oil and sesame oil, glycerol, glycerol formal, tetrahydrofurfuyl alcohol, polyethylene glycols and fatty acid esters of sorbitan, or mixtures of these substances.

For parenteral administration, the solutions and emulsions are also be in a sterile form which is isotonic with blood.

Suspensions can contain, in addition to the active ingredient or ingredients, the customary excipients, such as liquid diluents, for example water, ethyl alcohol and propylene glycol, and suspending agents, for example ethoxylated isostearyl alcohols, polyoxyethylene sorbitol and sorbitan esters, microcrystalline cellulose, aluminum metahydroxide, bentonite, agar-agar and tragacanth, or mixtures of these substances.

The formulation forms mentioned can also contain coloring agents, preservatives and additives which improve the smell and taste, for example peppermint oil and eucalyptus oil, and sweeteners, for example saccharin.

The therapeutically active ingredients should preferably be present in the abovementioned pharmaceutical formulations in a concentration of about 0.1 to 99.5, preferably about 0.5 to 95% by weight of the total mixture.

The abovementioned pharmaceutical formulations can also contain other pharmaceutical active compounds in addition to the compounds according to the present invention.

The abovementioned pharmaceutical formulations are prepared in the customary manner by known methods, for example by mixing the active ingredient or ingredients with vehicles.

The formulations mentioned can be used on humans and animals either orally, rectally, parenterally (intravenously, intramuscularly or subcutaneously), intracisternally, intravaginally, intraperitoneally or locally (dusting powder, ointment, drops) and for the therapy of infections in hollow spaces and body cavities. Possible suitable formulations are injection solutions, solutions and suspensions for oral therapy and gels, infusion formulations, emulsions, ointments or drops, ophthalmological and dermatological formulations, silver salts and other salts, eardrops, eye ointments, dusting powders or solutions can be used for local therapy. In the case of animals, intake can also be in suitable formulations via the feed or drinking water.

Gels, powders, dusting powders, tablets, delayed release tablets, premixes, concentrates, granules, pellets, capsules, aerosols, sprays and inhalants can furthermore be used on humans and animals. The compounds according to the present invention can moreover be incorporated into other carrier materials, such as for example, plastics (chain of plastic for local therapy), collagen or bone cement.

In general, it has proved advantageous in human medicine to administer the active ingredient or ingredients according to the present invention in total amounts of about 0.1 to about 20 mg/kg, preferably 0.5 to 10 mg/kg of body weight every 8 hours, if appropriate in the form of several individual doses, to achieve the desired results. However, it may be necessary to deviate from the dosages mentioned, and in particular to do so as a function of the nature and body weight of the object to be treated, the nature and severity of the disease, the nature of the formulation and of the administration of the medicament and the period or interval within which administration takes place.

As a result of acute oral toxicity test in rats, the benzopyran derivatives substituted with secondary amines including tetrazole, their stereoisomers or their pharmaceutically acceptable salts did not show toxicity in rats up to a dose of 2,000 mg/kg. Therefore, the compounds of the present invention can be safely administrated in vivo.

The present invention will be explained in more detail with reference to the following examples. However, the following examples are provided only to illustrate the present invention, and the present invention is not limited to them. Structures of those materials according to the present invention are decided by infrared spectroscopy, nuclear magnetic resonance spectroscopy, mass spectroscopy, liquid chromatography, X-ray crystallography, rotating crystal method, comparing Anal. Calcd with Found. of the compound.

EXAMPLE 1

Preparation of (2S,3S,4R)-6-nitro-4-[N-(4-chlorophenyl)-N-(2-methyl-2H-tetrazol-5-ylmethyl)amino]-3-hydroxy-2-methyl-2-dimethoxymethyl-3,4-dihydro-2H-1-benzopyran Step 1: Preparation of (2S,3S,4S)-6-nitro-2-methyl-2-dimethoxymethyl-3,4-epoxy-3,4-dihydro-2H-1-benzopyran 0.05 M $Na_2HPO_4$ aqueous solution (16.6 ml) was added to 0.55 M NaOCl aqueous solution (41.5 ml, 22.8 mmol) at 0° C.

To the aqueous solution was slowly added the solution of (2S)-6-nitro-2-methyl-2-dimethoxymethyl-2H-1-benzopyran (1.5 g, 5.7 mmol) and (S,S)-Mn(III) salen, catalyst (155 mg, 0.28 mmol) for an enantioselective epoxidation developed by Jacobsen in dichloromethane (8.5 ml). The solution was stirred at the room temperature for 12 hours. After the reaction was completed, the reaction mixture was filtered to remove the catalyst and the filtrate was extracted with dichloromethane (200 ml). The dichloromethane layer was washed with saturated brine solution, dried over anhydrous magnesium sulfate and concentrated to remove the dichloromethane. The crude product was purified by chromatography (developing solvent—n-hexane:ethyl acetate=4:1) to give (2S,3S,4S)-6-nitro-2-methyl-2-dimethoxymethyl-3,4-epoxy-3,4-dihydro-2H-1-benzopyran, the compound of formula 2 (1.4 g, yield: 88%).

$^1$H NMR (CDCl$_3$, 200 MHz): δ 1.53 (s, 3H), 3.25 (s, 3H), 3.49 (s, 3H), 3.79 (d, 1H), 3.96 (d, 1H), 4.19 (s, 1H), 6.82 (d, 1H), 8.09 (dd, 1H), 8.24 (d, 1H).

Step 2: Preparation of N-(4-chlorophenyl)-N-(2-methyl-2H-tetrazol-5-ylmethyl)amine a. Preparation of 5-chloromethyl-1H-tetrazole sodium azide (1.72 g, 26.4 mmol) was added in THF (30 ml), therein aluminum chloride (0.88 g, 6.6 mmol) and chloroacetonitrile (0.42 ml, 6.6 mmol) were added at 0° C. The reaction mixture was heated at reflux for 48 hours. After the reaction was completed, the reaction mixture was acidified to pH 3 with 3N HCl solution at 0° C., and extracted with ethyl acetate. The organic layer was washed with saturated brine solution, dried over anhydrous magnesium sulfate. The solvent was removed, and the resulting white solid was washed with mixture solution of ethyl acetate and n-hexane (1:4), to give 5-chloromethyl-1H-tetrazole (1.7 g, yield: 89%)

$^1$H NMR (CD$_3$OD, 200 MHz): δ 4.86 (s, 2H), 5.10 (brs, 1H).

b. Preparation of 5-chloromethyl-1-methyl-1H-tetrazol and 5-chloromethyl-2-methyl-2H-tetrazole 5-chloromethyl-1H-tetrazole (300 mg, 2.53 mmol) prepared the above a was dissolved in DMF (10 ml), therein K$_2$CO$_3$ (455 mg, 3.29 mmol) was added. Thereafter, therein MeI (0.16 ml, 2.53 mmol) was slowly added dropwise for 4 hours at room temperature, the reaction mixture was stirred at room temperature. After the said reaction was completed, water (30 ml) was added to the reaction mixture. The reaction mixture was extracted with ether (50 μl), thereafter the organic layer was washed with saturated brine solution, dried over anhydrous MgSO$_4$, and concentrated. The residue was purified by silcagel column chromatography (developing solvent-n-hexane:ethyl acetate=4:1) to give 5-chloromethyl-1-methyl-1H-tetrazole (88.1 mg, 26%) and 5-chloromethyl-2-methyl-2H-tetrazole (184.2 mg, yield: 55%).

5-chloromethyl-2-methyl-2H-tetrazole; $^1$H NMR (CDCl$_3$, 200 MHz): δ 4.37 (s, 3H), 4.51 (s, 2H), 5-chloromethyl-1-methyl-1H-tetrazole; $^1$H NMR (CDCl$_3$, 200 MHz): δ 4.05 (s, 3H), 4.52 (s, 2H).

c. Preparation of N-(4-chlorophenyl)-N-(2-methyl-2H-tetrazol-5-ylmethyl)amine p-chloroaniline (14 g, 13.2 mmol) was dissolved in DMF (120 ml), therein K$_2$CO$_3$ (9.49 g, 68.6 mmol) and 5-chloromethyl-2-methyl-2H-tetrazole (7 g, 34.4 mmol) obtained in the above step 2, thereto NaI (4.9 g, 34.3 mmol) was added. The reaction mixture was stirred for 4 hours at 80° C. After the reaction was completed, water (60 ml) was added therein. The reaction mixture was extracted with ether (20 ml), and the organic layer was washed with saturated brine solution, dried over anhydrous MgSO$_4$, and concentrated. The residue was purified by silica gel column chromatography (developing solvent-n-hexane:ethyl acetate=4:1) to give N-(4-chlorophenyl)-N-(2-methyl-2H-tetrazol-5-ylmethyl)amine, the compound of formula 3 (3.9 g, yield: 61%).

$^1$H NMR (CDCl$_3$, 200 MHz): δ 4.30 (s, 3H), 4.47 (brs, 1H), 4.56 (s, 2H), 6.64 (d, 2H), 7.11 (d, 2H).

Step 3: Preparation of (2S,3S,4R)-6-nitro-4-[N-(4-chlorophenyl)-N-(2-methyl-2H-tetrazol-5-ylmethyl)amino]-3-hydroxy-2-methyl-2-dimethoxymethyl-3,4-dihydro-2H-1-benzopyran The compound obtained in the step 1 (450 mg, 1.6 mmol) was dissolved in acetonitrile (0.5 ml). Secondary amine compound containing tetrazole, obtained in the above step 2 (363 mg, 1.6 mmol) and magnesium perchlorate ((MgClO$_4$)$_2$) (357 mg, 1.6 mmol) were added to the solution. The reaction mixture was stirred at room temperature for 10 hours, therein NaHCO$_3$ aqueous solution (20 ml) was added. The reaction mixture was extracted with ethyl acetate (30 ml). The organic layer was washed with saturated brine solution, dried over anhydrous magnesium sulfate and concentrated. The residue was purified by silca gel column chromatography (developing solvent-n-hexane:ethyl acetate=2:1), to give desired compound (435 mg, yield: 54%).

$^1$H NMR (CDCl$_3$, 200 MHz): δ 1.62 (s, 3H), 3.49 (s, 3H), 3.59 (s, 3H), 3.95 (dd, 1H), 4.32 (d, 1H), 4.48 (s, 3H), 4.72 (s, 1H), 4.83 (d, 1H), 5.60 (d, 1H), 6.82 (d, 2H), 6.95 (d, 1H), 7.16 (d, 2H), 7.99 (d, 1H), 8.06 (dd, 1H).

EXAMPLE 2

Preparation of (2S,3R,4S)-6-nitro-4-[N-(4-chlorophenyl)-N-(2-methyl-2H-tetrazol-5-ylmethyl)amino]-3-hydroxy-2-methyl-2-dimethoxymethyl-3,4-dihydro-2H-1-benzopyran Step 1: Preparation of (2S,3R,4R)-6-nitro-2-methyl-2-dimethoxymethyl-3,4-epoxy-3,4-dihydro-2H-1-benzopyran The same procedure as step 1 of example 1 was accomplished, except for using (2S)-6-nitro-2-methyl-2-dimethoxymethyl-2H-1-benzopyran (2.5 g, 9.4 mmol) and (R,R)-Mn(III) salen. The crude product was purified by silica gel column chromatography (developing solvent-n-hexane:ethyl acetate=4:1), to give desired compound (2.1 g, yield: 80%).

$^1$H NMR (CDCl$_3$, 200 MHz): δ 1.28 (s, 3H), 3.60 (s, 3H), 3.68 (s, 3H), 3.80 (d, 1H), 3.97 (d, 1H), 4.47 (s, 1H), 6.95 (d, 1H), 8.16 (dd, 1H), 8.31 (d, 1H).

Step 2: Preparation of (2S,3R,4S)-6-nitro-4-[N-(4-chlorophenyl)-N-(2-methyl-2H-tetrazol-5-ylmethyl)amino]-3-hydroxy-2-methyl-2-dimethoxymethyl-3,4-dihydro-2H-1-benzopyran The same procedure as step 3 of example 1 was accomplished, except for using epoxide compound (250 mg, 0.9 mmol) obtained in the above step 1. The crude product was purified by silica gel column chromatography (developing solvent-n-hexane:ethyl acetate=2:1), to give desired compound (359 mg, yield: 87%).

$^1$H NMR (CDCl$_3$, 200 MHz): δ 1.48 (s, 3H), 3.58 (s, 3H), 3.64 (s, 3H), 4.29 (s, 3H), 4.42 (dd, 1H), 4.52 (d, 1H), 4.61 (s, 1H), 4.82 (d, 1H), 5.13 (d, 1H), 5.18 (d, 1H), 6.84 (d, 2H), 7.05 (d, 1H), 7.15 (d, 2H), 8.08 (dd, 1H), 8.10 (d, 1H).

EXAMPLE 3

Preparation of (2S,3S,4R)-6-nitro-4-[N-(2-methyl-2H-tetrazol-5-ylmethyl)phenylamino]-3-hydroxy-2-methyl-2-dimethoxymethyl-3,4-dihydro-2H-1-benzopyran The same procedure as step 3 of example 1 was accomplished, except for using epoxide compound 450 mg (1.6 mmol) obtained in the above step 1 of example 1 and N-(2-methyl-2H-tetrazol-5-ylmethyl)phenylamine (302 mg, 1.6 mmol). The crude product was purified by silica gel column chromatography (developing solvent-n-hexane:ethyl acetate=2:1), to give desired compound (484 mg, yield: 64%).

$^1$H NMR (CDCl$_3$, 200 MHz): δ 1.49 (s, 3H), 3.57 (s, 3H), 3.64 (s, 3H), 4.31 (s, 3H), 4.32 (dd, 1H), 4.39 (d, 1H), 4.82 (d, 1H), 5.21 (d, 1H), 4.63 (s, 1H), 5.27 (d, 1H), 6.79-6.92 (m, 3H), 7.05 (d, 1H), 7.16-7.25 (m, 2H), 8.07 (dd, 1H), 8.09 (s, 1H).

EXAMPLE 4

Preparation of (2S,3R,4S)-6-nitro-4-[N-(2-methyl-2H-tetrazol-5-ylmethyl)phenylamino]-3-hydroxy-2-methyl-2-dimethoxymethyl-3,4-dihydro-2H-1-benzopyran The same procedure as step 3 of example 1 was accomplished, except for using epoxide compound (225 mg, 0.8 mmol) obtained in the above step 1 of example 2 and N-(2-methyl-2H-tetrazol-5-ylmethyl)phenylamine (151 mg, 0.8 mmol). The crude product was purified by silica gel column chromatography (developing solvent-n-hexane:ethyl acetate=2:1), to give desired compound (134 mg, yield: 56%). $^1$H NMR (CDCl$_3$, 200 MHz): δ 1.63 (s, 3H), 3.51 (s, 3H), 3.55 (s, 3H), 3.91 (dd, 1H), 4.29 (d, 1H), 4.33 (s, 3H), 4.75 (s, 1H), 4.88 (d, 1H), 5.45 (d, 1H), 5.69 (d, 1H), 6.80-6.97 (m, 4H), 7.20 (d, 2H), 8.01 (d, 1H), 8.07 (dd, 1H).

EXAMPLE 5

Preparation of (2S,3S,4R)-6-nitro-4-[N-(4-fluorophenyl)-N-(2-methyl-2H-tetrazol-5-ylmethyl)amino]-3-hydroxy-2-methyl-2-dimethoxymethyl-3,4-dihydro-2H-1-benzopyran The same procedure as step 3 of example 1 was accomplished, except for using epoxide compound (450 mg, 1.6 mmol) obtained in step 1 of example 1 and N-(4-fluorophenyl)-N-(2-methyl-2H-tetrazol-5-ylmethyl)amine (332 mg, 1.6 mmol). The crude product was purified by silica gel column chromatography (developing solvent-n-hexane:ethyl acetate=1:1) to desired compound (661 mg, yield: 86%).

$^1$H NMR (CDCl$_3$, 200 MHz): δ 1.62 (s, 3H), 3.48 (s, 3H), 3.53 (s,3H), 3.91 (dd, 1H), 4.33 (s, 3H), 4.35 (d, 1H), 4.71 (s, 1H), 4.82 (d, 1H), 5.38 (d, 1H), 5.50 (d, 1H), 6.85-6.96 (m, 5H), 8.03 (s, 1H), 8.05 (dd, 1H).

EXAMPLE 6

Preparation of (2S,3R,4S)-6-nitro-4-[N-(4-fluorophenyl)-N-(2-methyl-2H-tetrazol-5-ylmethyl)amino]-3-hydroxy-2-methyl-2-dimethoxymethyl-3,4-dihydro-2H-1-benzopyran The same procedure as step 3 of example 1 was accomplished, except for using epoxide compound (450 mg, 1.6 mmol) obtained in step 1 of example 2 and N-(4-fluorophenyl)-N-(2-methyl-2H-tetrazol-5-ylmethyl)amine (332 mg, 1.6 mmol). The crude product was purified by silica gel column chromatography (developing solvent-n-hexane:ethyl acetate=1:1), to give desired compound (528 mg, yield: 69%).

$^1$H NMR (CDCl$_3$, 200 MHz): δ 1.46 (s, 3H), 3.57 (s, 3H), 3.63 (s, 3H), 4.31 (s, 3H), 4.32 (d, 1H), 4.39 (dd, 1H), 4.60 (s, 1H), 4.80 (d, 1H), 5.10 (d, 1H), 5.19 (d, 1H), 6.87 (d, 2H), 6.90 (d, 2H), 7.03 (d, 1H), 8.08 (dd, 1H), 8.14 (d, 1H).

EXAMPLE 7

Preparation of (2S,3S,4R)-6-nitro-4-[N-benzyl-N-(2-methyl-2H-tetrazol-5-ylmethyl)amino]-3-hydroxy-2-methyl-2-dimethoxymethyl-3,4-dihydro-2H-1-benzopyran The same procedure as step 3 of example 1 was accomplished, except for using epoxide compound (300 mg, 1.07 mmol) obtained in step 1 of example 1 and N-benzyl-N-(2-methyl-2H-tetrazol-5-ylmethyl)amine (217 mg, 1.07 mmol). The crude product was purified by silica gel column chromatography (developing solvent-n-hexane:ethyl acetate=1:2), to give desired compound (282 mg, yield: 55%).

$^1$H NMR (CDCl$_3$, 200 MHz) δ 1.24 (s, 3H), 3.61 (s, 3H), 3.63 (s, 3H), 3.94-4.30 (m, 5H), 4.30 (s, 3H), 4.32 (d, 1H), 4.45 (s, 1H), 4.50 (d, 1H), 6.84 (d, 1H), 7.20-7.33 (m, 3H), 7.43 (d, 2H), 7.99 (dd, 1H), 8.74 (d, 1H)

EXAMPLE 8

Preparation of (2S,3R,4S)-6-nitro-4-[N-benzyl-N-(2-methyl-2H-tetrazol-5-ylmethyl)amino]-3-hydroxy-2-methyl-2-dimethoxymethyl-3,4-dihydro-2H-1-benzopyran The same procedure as step 3 of example 1 was accomplished, except for using epoxide compound (200 mg, 0.71 mmol) obtained in step 1 of example 2 and N-benzyl-N-(2-methyl-2H-tetrazol-5-ylmethyl)amine (145 mg, 0.71 mmol). The crude product was purified by silica gel column chromatography (developing solvent-n-hexane:ethyl acetate=1:2), to give desired compound (165 mg, yield: 48%).

$^1$H NMR (CDCl$_3$, 200 MHz): δ 1.58 (s, 3H), 3.30 (s, 3H), 3.34 (s, 3H), 3.89-4.12 (m, 6H), 4.27-4.33 (m, 5H), 6.83 (d, 1H), 7.23-7.38 (m, 3H), 7.45 (d, 2H), 8.01 (dd, 1H), 8.73 (d, 1H).

EXAMPLE 9

Preparation of (2S,3S,4R)-6-nitro-4-[N-(4-nitrophenyl)-N-(2-methyl-2H-tetrazol-5-ylmethyl)amino]-3-hydroxy-2-methyl-2-dimethoxymethyl-3,4-dihydro-2R-1-benzopyran The same procedure as step 3 of example 1 was accomplished, except for using epoxide compound (200 mg, 0.71 mmol) obtained in step 1 of example 1 and N-(4-nitrophenyl)-N-(2-methyl-2H-tetrazol-5-ylmethyl)amine (167 mg, 0.71 mmol). The crude product was purified by silica gel column chromatography (developing solvent-n-hexane:ethyl acetate=1:1), to give desired compound (162 mg, yield: 45%).

$^1$H NMR (CDCl$_3$, 200 MHz): δ 1.59 (s, 3H), 3.65-3.49 (m, 7H), 4.32-4.40 (m, 4H), 4.62 (s, 1H), 4.86 (d, 1H), 5.14 (d, 1H), 5.45 (d, 1H), 6.98 (d, 2H), 7.07 (d, 1H), 7.99-8.15 (m, 4H).

EXAMPLE 10

Preparation of (2S,3S,4R)-6-amino-4-[N-(4-chlorophenyl)-N-(2-methyl-2H-tetrazol-5-ylmethyl)amino]-3-hydroxy-2-methyl-2-dimethoxymethyl-3,4-dihydro-2H-1-benzopyran (2S,3S,4R)-6-nitro-4-[N-(4-chlorophenyl)-N-(2-methyl-2H-tetrazol-5-ylmethyl)amino]-3-hydroxy-2-methyl-2-dimethoxymethyl-3,4-dihydro-2H-1-benzopyran obtained in the example 1 (100 mg, 0.2 mmol) was dissolved in methanol (2 ml), thereto Cu(OAc)$_2$ aqueous solution (0.38 ml, 0.4 M aqueous solution, 0.15 mmol) was added. Sodium borohydride (NaBH$_4$) (113 mg, 3.0 mmol) was slowly added to the solution for 30 min at room temperature, the reaction mixture was stirred for 1 hours, thereafter ethyl acetate (5 ml) was added to the reaction mixture. The resulting mixture was filtered to remove precipitated black solid. Saturated NaHCO$_3$ aqueous solution (5 ml) was added to the filtrate, and extracted with ethyl acetate (30 ml). The organic layer was washed with saturated brine solution, dried over anhydrous magnesium sulfate, and concentrated. The residue was purified by silica gel column chromatography (developing solvent-n-hexane:ethyl acetate=1:3), to give desired compound, the compound that R$_1$ is substituted to amino group (62 mg, yield: 67%).

$^1$H NMR (CDCl$_3$, 200 MHz): δ 1.34 (s, 3H), 3.51 (s, 3H), 3.61 (s, 3H), 4.02 (s, 3H), 4.10 (dd, 1H), 4.33 (d, 1H), 4.47 (s, 1H), 4.68 (d, 1H), 4.80-4.97 (m, 2H), 6.35 (d, 1H), 6.54 (dd, 1H), 6.74 (d, 1H), 6.81 (d, 2H), 7.14 (d, 2H).

EXAMPLE 11

Preparation of (2S,3R,4S)-6-amino-4-[N-(4-chlorophenyl)-N-(2-methyl-2H-tetrazol-5-ylmethyl)amino]-3-hydroxy-2-methyl-2-dimethoxymethyl-3,4-dihydro-2H-1-benzopyran The same procedure as example 10 was accomplished, except for using the compound (150 mg, 0.3 mmol) obtained in example 2. The crude product was purified with silica gel column chromatography (developing solvent-n-hexane:ethyl acetate=1:3), to give desired compound (74 mg, yield: 52%).

$^1$H NMR (CDCl$_3$, 200 MHz): δ 1.54 (s, 3H), 3.49 (s, 3H), 3.52 (s, 3H), 3.95 (dd, 1H), 4.30 (d, 1H), 4.32 (s, 3H), 4.41-4.70 (m, 3H), 5.33 (d, 1H), 6.45 (s, 1H), 6.55 (dd, 1H), 6.68 (d, 1H), 6.82 (d, 2H), 7.13 (d, 2H).

EXAMPLE 12

Preparation of (2S,3S,4R)-6-nitro-4-[N-(4-chlorophenyl)-N-(1-methyl-1H-tetrazol-5-ylmethyl)amino]-3-hydroxy-2-methyl-2-dimethoxymethyl-3,4-dihydro-2H-1-benzopyran Step 1: Preparation of N-(4-chlorophenyl)-N-(1-methyl-1H-tetrazol-5-ylmethyl)amine
The same procedure as step 2 of example 1 was accomplished except for using p-chloroaniline (5.8 g, 45.3 mmol) and 5-chloromethyl-1-methyl-1H-tetrazol (6 g, 45.3 mmol). The crude product was purified by silica gel column chromatography (developing solvent-n-hexane:ethyl acetate=2:1), to give desired compound (3.68 g, yield: 36%).
Step 2: Preparation of (2S,3S,4R)-6-nitro-4-[N-(4-chlorophenyl)-N-(1-methyl-1H-tetrazol-5-ylmethyl)amino]-3-hydroxy-2-methyl-2-dimethoxymethyl-3,4-dihydro-2H-1-benzopyran The same procedure as step 3 of example 1 was accomplished, except for using epoxide compound (150 mg, 0.53 mmol) obtained in step 1 of example 1 and N-(4-chlorophenyl)-N-(1-methyl-1H-tetrazol-5-ylmethyl)amine (121 mg, 0.53 mmol) obtained in the above step 1. The crude product was purified by silica gel column chromatography (developing solvent-n-hexane:ethyl acetate=1:1), to give desired compound (194 mg, yield: 72%).

$^1$H NMR (CDCl$_3$, 200 MHz): δ 1.44 (s, 3H), 3.52 (s, 3H), 3.63 (s, 3H), 4.08 (s, 3H), 4.20 (dd, 1H), 4.35 (d, 1H), 4.58 (s, 1H), 4.84 (d, 1H), 5.08 (d, 1H), 5.58 (d, 1H), 6.81 (d, 2H), 7.17 (d, 2H), 7.03 (d, 1H), 8.02 (d, 1H), 8.04 (dd, 1H).

EXAMPLE 13

Preparation of (2S,3S,4R)-6-nitro-4-[N-(1-methyl-1H-tetrazol-5-ylmethyl)phenylamino]-3-hydroxy-2-methyl-2-dimethoxymethyl-3,4-dihydro-2H-1-benzopyran The same procedure as step 3 of example 1 was accomplished, except for using epoxide compound (150 mg, 0.53 mmol) obtained in step 1 of example 1 and N-(1-methyl-1H-tetrazol-5-ylmethyl)amine (101 mg, 0.53 mmol). The crude product was purified by silica gel column chromatography (developing solvent-n-hexane:ethyl acetate=2:1), to give desired compound (203 mg, yield: 81%).

$^1$H NMR (CDCl$_3$, 200 MHz): δ 1.47 (s, 3H), 3.54 (s, 3H), 3.64 (s, 3H), 4.08 (s, 3H), 4.18 (dd, 1H), 4.37 (d, 1H), 4.61 (s, 1H), 4.84 (d, 1H), 5.18 (d, 1H), 5.66 (d, 1H), 6.86-7.08 (m, 4H), 7.24 (d, 2H), 8.05 (s, 1H), 8.10 (dd, 1H).

EXAMPLE 14

Preparation of (2S,3S,4R)-6-nitro-4-[N-(4-fluorophenyl)-N-(1-methyl-1H-tetrazol-5-ylmethyl)amino]-3-hydroxy-2-methyl-2-dimethoxymethyl-3,4-dihydro-2H-1-benzopyran The same procedure as step 3 of example 1 was accomplished, except for using epoxide compound (150 mg, 0.53 mmol) obtained in step 1 of example 1 and N-(4-fluorophenyl)-N-(1-methyl-1H-tetrazol-5-ylmethyl)amine (111 mg, 0.53 mmol). The crude product was purified by silica gel column chromatography (developing solvent-n-hexane:ethyl acetate=1:1), to give desired compound (198 mg, yield: 76%).

$^1$H NMR (CDCl$_3$, 200 MHz): δ 1.43 (s, 3H), 3.56 (s, 3H), 3.64 (s, 3H), 4.08 (s, 3H), 4.19 (dd, 1H), 4.37 (d, 1H), 4.57 (s, 1H), 4.84 (d, 1H), 4.99 (d, 1H), 5.47 (d, 1H), 7.03 (d, 1H), 7.94 (dd, 4H), 8.06 (dd, 1H), 8.09 (s, 1H).

EXAMPLE 15

Preparation of (2S,3S,4R)-6-nitro-4-[N-benzyl-N-(1-methyl-1H-tetrazol-5-ylmethyl)amino]-3-hydroxy-2-methyl-2-dimethoxymethyl-3,4-dihydro-2H-1-benzopyran The same procedure as step 3 of example 1 was accomplished, except for using epoxide compound (200 mg, 0.71 mmol) obtained in step 1 of example 1 and N-benzyl-N-(1-methyl-1H-tetrazol-5-ylmethyl)amine (145 mg, 0.71 mmol). The crude product was purified by silica gel column chromatography (developing solvent-n-hexane:ethyl acetate=1:2), to give desired compound (192 mg, yield: 56%).

¹H NMR (CDCl₃, 200 MHz): δ 1.30 (s, 3H), 3.63 (s, 3H), 3.65 (s, 3H), 3.67 (s, 3H), 3.80-4.10 (m, 4H), 4.37-4.62 (m, 4H), 6.89 (d, 1H), 7.26-7.35 (m, 5H), 8.00 (dd, 1H), 8.57 (d, 1H).

EXAMPLE 16

Preparation of (2S,3R,4S)-6-nitro-4-[N-benzyl-N-(1-methyl-1H-tetrazol-5-ylmethyl)amino]-3-hydroxy-2-methyl-2-dimethoxymethyl-3,4-dihydro-2H-1-benzopyran The same procedure as step 3 of example 1 was accomplished, except for using epoxide compound (200 mg, 0.71 mmol) obtained in step 1 of example 2 and N-benzyl-N-(2-methyl-2H-tetrazol-5-ylmethyl)amine (145 mg, 0.71 mmol). The crude product was purified by silica gel column chromatography (developing solvent-n-hexane:ethyl acetate=1:2), to give desired compound (70 mg, yield: 20%).

¹H NMR (CDCl₃, 200 MHz): δ 1.60 (s, 3H), 3.39 (s, 3H), 3.41 (s, 3H), 3.56 (dd, 1H), 3.74-3.97 (m, 4H), 4.02-4.33 (m, 6H), 6.84 (d, 1H), 7.24-7.38 (m, 5H), 8.03 (dd, 1H), 8.52 (d, 1H).

EXAMPLE 17

Preparation of (2S,3S,4R)-6-amino-4-[N-(4-chlorophenyl)-N-(1-methyl-1H-tetrazol-5-ylmethyl)amino]-3-hydroxy-2-methyl-2-dimethoxymethyl-3,4-dihydro-2H-1-benzopyran The same procedure as example 10 was accomplished, except for using epoxide compound (100 mg, 0.2 mmol) obtained in example 12. The crude product was purified with silica gel column chromatography (developing solvent-n-hexane:ethyl acetate=1:4), to give desired compound (62 mg, yield: 67%).

¹H NMR (CDCl₃, 200 MHz): δ 1.34 (s, 3H), 3.51 (s, 3H), 3.61 (s, 3H), 4.02 (s, 3H), 4.10 (dd, 1H), 4.33 (d, 1H), 4.47 (s, 1H) 4.68 (d, 1H), 4.80-4.97 (m, 2H), 6.35 (d, 1H), 6.54 (dd, 1H), 6.74 (d, 1H), 6.81 (d, 2H), 7.14 (d, 2H).

EXAMPLE 18

Preparation of (2S,3S,4R)-6-nitro-4-[N-(4-chlorophenyl)-N-(1H-tetrazol-5-ylmethyl)amino]-3-hydroxy-2-methyl-2-dimethoxymethyl-3,4-dihydro-2H-1-benzopyran Step 1: Preparation of (2S,3S,4R)-6-nitro-4-[N-(4-chlorophenyl)-N-[2-(1-ethoxyethyl)-2H-tetrazol-5-ylmethyl]amino]-3-hydroxy-2-methyl-2-dimethoxymethyl-3,4-dihydro-2H-1-benzopyran The same procedure as step 3 of example 1 was accomplished, except for using epoxide compound (900 mg, 3.2 mmol) obtained in step 1 of example 1 and N-(4-chlorophenyl)-N-[2-(1-ethoxyethyl)-2H-tetrazol-5-ylmethyl]amine (900 mg, 3.2 mmol). The crude product was purified by silica gel column chromatography (developing solvent-n-hexane: ethyl acetate=2:1), to give desired compound (566 mg, yield: 31%).

¹H NMR (CDCl₃, 200 MHz): δ 1.12 (m, 3H), 1.48 (s, 3H), 1.82 (d, 3H), 3.26-3.34 (m, 1H), 3.49-3.59 (m, 1H), 3.57 (s, 3H), 3.64 (s, 3H), 4.43-4.10 (m, 2H), 4.62 (s, 1H), 4.86 (d, 1H), 5.15 (d, 1H), 5.20 (d, 1H), 6.00 (q, 1H), 6.85 (d, 2H), 7.05 (d, 1H), 7.13 (d, 2H), 8.06 (dd, 1H), 8.10 (d, 1H).

Step 2: Preparation of (2S,3S,4R)-6-nitro-4-[N-(4-chlorophenyl)-N-(1H-tetrazol-5-ylmethyl)amino]-3-hydroxy-2-methyl-2-dimethoxymethyl-3,4-dihydro-2H-1-benzopyran The compound obtained in the above step 1 (300 mg, 0.53 mmol) was dissolved in methanol (2 ml), thereto 3% aqueous HCl solution (1 ml) was added. The reaction mixture was stirred at room temperature for 12 hours. Water (20 ml) was added to the reaction mixture. The reaction mixture was extracted with ethyl acetate (30 ml). The organic layer was dried over anhydrous magnesium sulfate, and concentrated. The crude product was purified by silica gel column chromatography (developing solvent-n-hexane:ethyl acetate=1:4), to give desired compound (160 mg, yield: 61%).

¹H NMR (CDCl₃, 200 MHz): δ 1.49 (s, 3H), 3.63 (s, 6H), 4.60-4.40 (m, 3H), 5.20-4.95 (m, 3H), 6.78-6.50 (m, 3H), 7.00 (d, 1H), 7.10 (d, 2H), 7.99 (d, 1H), 8.10 (dd, 1H).

EXAMPLE 19

Preparation of (2S,3S,4R)-6-nitro-4-[N-(1H-tetrazol-5-ylmethyl)phenylamino]-3-hydroxy-2-methyl-2-dimethoxymethyl-3,4-dihydro-2H-1-benzopyran The same procedure as step 1 of example 18 was accomplished, except for using N-[2-(1-ethoxyethyl)-2H-tetrazol-5-ylmethyl]phenylamine, to give the compound of which tetrazol group was protected. Using the compound (272 mg, 0.52 mmol), the same procedure as step 2 of example 18 was accomplished. The crude product was purified by silica gel column chromatography (developing solvent-n-hexane:ethyl acetate=1:4), to give desired compound (119 mg, yield: 50%).

¹H NMR (CDCl₃, 200 MHz): δ 1.49 (s, 3H), 3.62 (s, 6H), 4.75-4.43 (m, 3H), 5.21-4.97 (m, 3H), 6.84-6.73 (m, 3H), 6.99 (d, 1H), 7.20-7.12 (m, 2H), 8.03 (d, 1H), 8.11 (dd, 1H)

EXAMPLE 20

Preparation of (2S,3S,4R)-6-nitro-4-[N-benzyl-N-(1H-tetrazol-5-ylmethyl)amino]-3-hydroxy-2-methyl-2-dimethoxymethyl-3,4-dihydro-2H-1-benzopyran The same procedure as step 1 of example 18 was accomplished, except for using the epoxide compound obtained in step 1 of example 1 and N-benzyl-N-[2-(1-ethoxyethyl)-2H-tetrazol-5-ylmethyl]amine, to give the compound (254 mg, 0.47 mmol). Thereafter, the same procedure as step 2 of example 18 was accomplished. The crude product was purified by silica gel column chromatography (developing solvent-n-hexane:ethyl acetate=1:4), to give desired compound (107 mg, yield: 48%).

¹H NMR (CDCl₃, 200 MHz): δ 1.25 (s, 3H), 3.64 (s, 6H), 3.85 (m, 2H), 4.16 (d, 1H), 4.52-4.41 (m, 4H), 6.90 (d, 1H), 7.25-7.17 (m, 5H), 8.05 (dd, 1H), 8.41 (d, 1H).

EXAMPLE 21

Preparation of (2S,3S,4R)-6-nitro-4[N-(3-chlorophenyl)-N-(2-methyl-2H-tetrazol-5-ylmethyl)amino]-3-hydroxy-2-methyl-2-dimethoxymethyl-3,4-dihydro-2H-1-benzopyran The same procedure as step 3 of example 1 was accomplished, except for using the epoxide compound (150 mg, 0.53 mmol) obtained in step 1 of example 1 and N-(4-chlorophenyl)-N-(2-methyl-2H-tetrazol-5-ylmethyl)amine. The crude product was purified with silica gel column chromatography (developing solvent-n-hexane:ethyl acetate=1:1), to give desired compound (249 mg, yield: 9.3%).

¹H NMR (CDCl₃, 200 MHz): δ 1.50 (s, 3H), 4.10 (s, 3H), 4.41-4.34 (m, 4H), 4.62 (s, 1H), 4.81 (d, 1H), 5.20 (d, 2H), 6.80 (dd, 2H), 6.89 (s, 1H), 7.07 (m, 2H), 8.08 (m, 2H).

EXAMPLE 22

Preparation of (2S,3S,4R)-6-amino-4-[N-(3-chlorophenyl)-N-(2-methyl-2H-tetrazol-5-ylmethyl)amino]-3-hydroxy-2-methyl-2-dimethoxymethyl-3,4-dihydro-2H-1-benzopyran The same procedure as example 10 was accomplished, except for using the compound (148 mg, 0.3 mmol) obtained in example 21. The crude product was purified with silica gel column chromatography (developing solvent-n-hexane:ethyl acetate=1:4), to give desired compound (106 mg, yield: 74%).
$^1$H NMR (CDCl$_3$, 200 MHz): δ 1.41 (s, 3H), 3.55 (s, 3H), 3.61 (s, 3H), 4.20-4.40 (m, 6H), 4.57 (s, 1H), 4.68 (d, 1H), 5.09 (d, 1H), 6.40 (d, 1H), 6.54 (dd, 1H), 6.70-6.80 (m, 3H), 6.87 (s, 1H), 7.08 (t, 1H).

EXAMPLE 23

Preparation of (2S,3S,4R)-6-nitro-4-[N-(4-methylphenyl)-N-(2-methyl-2H-tetrazol-5-ylmethyl)amino]-3-hydroxy-2-methyl-2-dimethoxymethyl-3,4-dihydro-2H-1-benzopyran The same procedure as step 3 of example 1 was accomplished, except for using the epoxide compound (300 mg, 1.1 mmol) obtained in step 1 of example 1 and N-(4-methylphenyl)-N-(2-methyl-2H-tetrazol-5-ylmethyl)amine. The crude product was purified by silica gel column chromatography (developing solvent-n-hexane:ethyl acetate=2:1), to give desired compound (463 mg, yield: 69%).
$^1$H NMR (CDCl$_3$, 200 MHz): δ 1.48 (s, 3H), 2.02 (s, 3H), 3.57 (s, 3H), 3.64 (s, 3H), 4.38-4.31 (m, 5H), 4.62 (s, 1H), 4.84 (d, 1H), 5.16 (s, 1H), 5.21 (s, 1H), 6.82 (d, 2H), 6.99-7.06 (m, 3H), 8.06 (dd, 1H), 8.12 (s, 1H).

EXAMPLE 24

Preparation of (2S,3S,4R)-6-amino-4-[N-4-methylphenyl]-N-(2-methyl-2H-tetrazol-5-ylmethyl)amino]-3-hydroxy-2-methyl-2-dimethoxymethyl-3,4-dihydro-2H-1-benzopyran The same procedure as example 10 was accomplished, except for using the epoxide compound (263 mg, 0.54 mmol) obtained in example 23. The crude product was purified by silica gel column chromatography (developing solvent-n-hexane:ethyl acetate=1:4), to give desired compound (176 mg, yield: 72%).
$^1$H NMR (CDCl$_3$, 200 MHz): δ 1.41 (s, 3H), 2.23 (s, 3H), 3.55 (s, 3H), 3.61 (s, 3H), 4.30 (s, 3H), 4.42 (s, 1H), 4.59 (s, 1H), 4.70 (s, 1H), 4.93 (s, 1H), 5.11 (d, 1H), 6.44 (d, 1H), 6.53 (dd, 1H), 6.79 (dd, 3H), 7.00 (d, 2H).

EXAMPLE 25

Preparation of (2S,3R,4S)-6-nitro-4-[N-(3-chlorophenyl)-N-(2-methyl-2H-tetrazol-5-ylmethyl)amino]-3-hydroxy-2-methyl-2-dimethoxymethyl-3,4-dihydro-2H-1-benzopyran The same procedure as step 3 of example 1 was accomplished, except for using the epoxide compound (150 mg, 0.53 mmol) obtained in step 1 of example 2 and N-(3-chlorophenyl)-N-(2-methyl-2H-tetrazol-5-ylmethyl)amine. The crude product was purified by silica gel column chromatography (developing solvent-n-hexane:ethyl acetate=1:1), to give desired compound (124 mg, yield: 46%).
$^1$H NMR (CDCl$_3$, 200 MHz): δ 1.63 (s, 3H), 3.52 (s, 3H), 3.55 (s, 3H), 3.95 (q, 1H), 4.36 (m, 4H), 4.75 (s, 1H), 4.85 (d, 1H), 5.47 (s, 1H), 5.70 (d, 2H), 6.78 (dd, 1H), 6.90 (s, 1H), 6.95 (d, 1H), 7.12 (t, 1H), 7.96 (s, 1H), 8.08 (dd. 1H)

EXAMPLE 26

Preparation of (2S,3R,4S)-6-amino-4-[N-(3-chlorophenyl)-N-(2-methyl-2H-tetrazol-5-ylmethyl)amino]-3-hydroxy-2-methyl-2-dimethoxymethyl-3,4-dihydro-2H-1-benzopyran The same procedure as example 10 was accomplished, except for using the compound (180 mg, 0.37 mmol) obtained in example 25. The crude product was purified by silica gel column chromatography (developing solvent-n-hexane:ethyl acetate=1:4), to give desired compound (95 mg, yield: 54%).
$^1$H NMR (CDCl$_3$, 200 MHz): δ 1.54 (s, 3H), 3.40 (s, 1H), 3.50 (s, 3H), 3.53 (s, 3H), 3.92 (q, 1H), 4.32-4.50 (m, 4H), 4.64 (s, 1H), 4.63-4.73 (m, 2H), 5.41 (d, 1H), 6.42 (s, 1H), 6.56 (dd, 1H) 6.68-6.78 (m, 3H), 6.91 (s, 1H), 7.05 (t, 1H).

EXAMPLE 27

Preparation of (2S,3R,4S)-6-nitro-4-[N-(4-methylphenyl)-N-(2-methyl-2H-tetrazol-5-ylmethyl)amino]-3-hydroxy-2-methyl-2-dimethoxymethyl-3,4-dihydro-2H-1-benzopyran The same procedure as step 3 of example 1 was accomplished, except for using the epoxide compound (300 mg, 1.1 mmol) obtained in step 1 of example 2 and N-(4-methylphenyl)-N-(2-methyl-2H-tetrazol-5-ylmethyl)amine. The crude product was purified by silica gel column chromatography (developing solvent-n-hexane:ethyl acetate=2:1), to give desired compound (388 mg, yield: 75%).
$^1$H NMR (CDCl$_3$, 200 MHz): δ 1.62 (s, 3H), 2.24 (s, 3H), 3.49 (s, 3H), 3.55 (s, 3H), 3.92 (q, 1H), 4.26 (m, 4H), 4.74 (s, 1H), 4.86 (d, 1H), 5.40 (d, 1H), 5.55 (d, 1H), 6.81 (d, 2H), 7.04-6.91 (m, 3H), 8.02 (s, 3H), 8.06 (d, 1H).

EXAMPLE 28

Preparation of (2S,3R,4S)-6-amino-4-[N-(4-methylphenyl)-N-(2-methyl-2H-tetrazol-5-ylmethyl)amino]-3-hydroxy-2-methyl-2-dimethoxymethyl-3,4-dihydro-2H-1-benzopyran The same procedure as example 10 was accomplished, except for using the compound (238 mg, 0.49 mmol) obtained in example 27. The crude product was purified by silica gel column chromatography (developing solvent-n-hexane:ethyl acetate=1:4), to give desired compound (168 mg, yield: 69%).
$^1$H NMR (CDCl$_3$, 200 MHz): δ 1.53 (s, 3H), 2.23 (s, 3H), 3.48 (s, 3H), 3.52 (s, 3H), 3.92 (d, 1H), 4.30 (s, 3H), 4.39 (d, 1H), 4.64 (s, 1H), 4.65-4.74 (m, 2H), 5.35 (d, 1H), 6.48 (d, 1H), 6.52 (d, 1H), 6.69 (d, 1H), 6.82 (d, 2H), 7.00 (d, 2H)

EXAMPLE 29

Preparation of (2S,3R,4S)-6-nitro-4-[N-(2-chlorophenyl)-N-(2-methyl-2H-tetrazol-5-ylmethyl)amino]-3-hydroxy-2-methyl-2-dimethoxymethyl-3,4-dihydro-2H-1-benzopyran The same procedure as step 3 of example 1 was accomplished, except for using the epoxide compound (450 mg, 1.6 mmol) obtained in step 1 of example 2 and N-(2-chlorophenyl)-N-(2-methyl-2H-tetrazol-5-ylmethyl)amine. The crude product was purified by silica gel column chromatography (developing solvent-n-hexane:ethyl acetate=2:1), to give desired compound (118 mg, yield: 15%).

$^1$H NMR (CDCl$_3$, 200 MHz): δ 1.63 (s, 3H), 3.42 (s, 3H), 3.53 (m, 3H), 4.13 (d, 1H), 4.22 (s, 3H), 4.45 (d, 1H), 4.54 (s, 1H), 4.63 (d, 1H), 5.12 (d, 1H), 6.88-6.93 (m, 2H), 7.16 (t, 1H), 7.34 (dd, 1H), 7.67 (dd, 1H), 8.08 (dd, 1H), 9.12 (dd, 1H)

EXAMPLE 30

Preparation of (2S,3R,4S)-6-amino-4-[N-(2-chlorophenyl)-N-(2-methyl-2H-tetrazol-5-ylmethyl) amino]-3-hydroxy-2-methyl-2-dimethoxymethyl-3,4-dihydro-2H-1-benzopyran The same procedure as example 10 was accomplished, except for using the compound (108 mg, 0.21 mmol) obtained in example 29. The crude product was purified by silica gel column chromatography (developing solvent-n-hexane:ethyl acetate=1:4), to give desired compound (78 mg, yield: 78%).

$^1$H NMR (CDCl$_3$, 200 MHz): δ 1.49 (s, 3H), 3.16 (brs, 1H), 3.35 (s, 3H), 3.48 (s, 3H), 4.19 (s, 3H), 4.30 (d, 1H), 4.50 (s, 1H), 4.82 (d, 1H), 4.94 (d, 1H), 6.58 (dd, 1H), 6.67 (d, 1H), 6.85 (t, 1H), 7.10 (t, 1H), 7.28 (d, 1H), 7.45 (d, 1H) 7.74 (d, 1H).

EXAMPLE 31

Preparation of (2S,3R,4S)-6-nitro-4-[N-(4-trifluoromethoxyphenyl)-N-(2-methyl-2H-tetrazol-5-ylmethyl)amino]-3-hydroxy-2-methyl-2-dimethoxymethyl-3,4-dihydro-2H-1-benzopyran The same procedure as step 3 of example 1 was accomplished, except for using the epoxide compound (300 mg, 1.07 mmol) obtained in step 1 of example 2 and N-(4-trifluoromethoxyphenyl)-N-(2-methyl-2H-tetrazol-5-ylmethyl) amine. The crude product was purified by silica gel column chromatography (developing solvent-n-hexane:ethyl acetate=2:1), to give desired compound (248 mg, yield: 42%).

$^1$H NMR (CDCl$_3$, 200 MHz): δ 1.63 (s, 3H), 3.50 (s, 3H), 3.55 (s, 3H), 3.92 (q, 1H), 4.30 (brs, 1H), 4.35 (s, 3H), 4.73 (s, 3H), 4.85 (d, 1H), 5.47 (s, 1H), 5.62 (d, 2H), 6.86 (d, 2H), 6.96 (d, 1H), 7.07 (d, 2H), 7.99 (s, 1H), 8.07 (dd, 1H).

EXAMPLE 32

Preparation of (2S,3R,4S)-6-amino-4-[N-(4-trifluoromethoxyphenyl)-N-(2-methyl-2H-tetrazol-5-ylmethyl)amino]-3-hydroxy-2-methyl-2-dimethoxymethyl-3,4-dihydro-2H-1-benzopyran The same procedure as example 10 was accomplished, except for using the compound (165 mg, 0.30 mmol) obtained in example 31. The crude product was purified by silica gel column chromatography (developing solvent-n-hexane:ethyl acetate=1:4), to give desired compound (117 mg, yield: 75%).

$^1$H NMR (CDCl$_3$, 200 MHz): δ 1.54 (s, 3H), 3.48 (s, 3H), 3.52 (s, 3H), 3.95 (q, 1H), 4.32 (s, 1H), 4.41 (d, 1H), 4.66-4.74 (m, 3H), 5.36 (d, 1H), 6.46 (s, 1H), 6.54 (dd, 1H), 6.70 (d, 1H), 6.86 (d, 2H), 7.03 (d, 2H).

EXAMPLE 33

Preparation of (2S,3R,4S)-6-nitro-4-[N-(4-trifluoromethylphenyl)-N-(2-methyl-2H-tetrazol-5-ylmethyl)amino]-3-hydroxy-2-methyl-2-dimethoxymethyl-3,4-dihydro-2H-1-benzopyran The same procedure as step 3 of example 1 was accomplished, except for using the epoxide compound (300 mg, 1.07 mmol) obtained in step 1 of example 2 and N-(4-trifluoromethylphenyl)-N-(2-methyl-2H-tetrazol-5-ylmethyl) amine. The crude product was purified by silica gel column chromatography (developing solvent-n-hexane:ethyl acetate=2:1), to give desired compound (92 mg, yield: 16%).

$^1$H NMR (CDCl$_3$, 200 MHz): δ 1.63 (s, 3H), 3.51 (s, 3H), 3.54 (s, 3H), 3.98 (brs, 1H), 4.35 (m, 4H), 4.74 (s, 1H), 4.92 (d, 1H), 5.80 (s, 1H), 6.72 (d, 1H), 6.96 (d, 2H), 7.40-7.47 (m, 2H), 7.95 (m, 1H), 8.06 (dd, 1H).

EXAMPLE 34

Preparation of (2S,3R,4S)-6-amino-4-[N-(4-trifluoromethylphenyl)-N-(2-methyl-2H-tetrazol-5-ylmethyl)amino]-3-hydroxy-2-methyl-2-dimethoxymethyl-3,4-dihydro-2H-1-benzopyran The same procedure as example 10 was accomplished, except for using the compound (92 mg, 0.17 mmol) obtained in example 33. The crude product was purified by silica gel column chromatography (developing solvent-n-hexane:ethyl acetate=1:4), to give desired compound (26 mg, yield: 30%).

$^1$H NMR (CDCl$_3$, 200 MHz): δ 1.55 (s, 3H), 3.50 (s, 3H), 3.53 (s, 3H), 3.99 (brs, 1H), 4.32-4.40 (m, 4H), 4.64-4.80 (m, 3H), 5.56 (s, 1H), 6.40 (s, 1H), 6.55 (dd, 1H), 6.71 (d, 1H), 6.95 (d, 2H), 7.42 (d, 2H)

EXAMPLE 35

Preparation of (2S,3R,4S)-6-nitro-4-[N-(3-acethylphenyl)-N-(2-methyl-2H-tetrazol-5-ylmethyl) amino]-3-hydroxy-2-methyl-2-dimethoxymethyl-3,4-dihydro-2H-1-benzopyran The same procedure as step 3 of example 1 was accomplished, except for using the epoxide compound (300 mg, 1.07 mmol) obtained in step 1 of example 2 and N-(3-acethylphenyl)-N-(2-methyl-2H-tetazole-5-ylmethyl)amine. The crude product was purified by silica gel column chromatography (developing solvent-n-hexane:ethyl acetate=1:1), to give desired compound (232 mg, yield: 42%).

$^1$H NMR (CDCl$_3$, 200 MHz): δ 1.63 (s, 3H), 2.54 (s, 3H), 3.56 (s, 6H), 3.97 (s, 1H), 4.33 (m, 4H), 4.76 (s, 1H), 4.92 (d, 1H), 5.43 (s, 1H), 5.80 (s, 1H), 6.96 (d, 1H), 7.04 (d, 1H), 7.24-7.38 (m, 2H), 7.60 (d, 1H), 7.96 (d, 1H).

EXAMPLE 36

Preparation of (2S,3R,4S)-6-amino-4-[N-[3-(1-hydroxyethyl)phenyl]-N-(2-methyl-2H-tetrazol-5-ylmethyl)amino]-3-hydroxy-2-methyl-2-dimethoxymethyl-3,4-dihydro-2H-1-benzopyran The same procedure as example 10 was accomplished, except for using the compound (151 mg, 0.29 mmol) obtained in example 35. The crude product was purified by silica gel column chromatography (developing solvent-n-hexane:ethyl acetate=1:4), to give desired compound (90 mg, yield: 64%).

¹H NMR (CDCl₃, 200 MHz): δ 1.43 (dd, 3H), 1.54 (s, 3H), 3.51 (s,3H), 3.54 (s, 3H), 3.97 (d, 1H), 4.30-4.45 (m, 4H), 4.65-4.78 (m, 3H), 5.47 (d, 1H), 6.47-6.56 (m, 2H), 6.68-6.77 (m, 3H), 6.99 (d, 1H), 7.16 (t, 1H)

EXAMPLE 37

Preparation of (2S,3R,4S)-6-nitro-4-[N-(2-methyl-4-fluorophenyl)-N-(2-methyl-2H-tetrazol-5-ylmethyl) amino]-3-hydroxy-2-methyl-2-dimethoxymethyl-3,4-dihydro-2H-1-benzopyran The same procedure as step 3 of example 1 was accomplished, except for using the epoxide compound (450 mg, 1.6 mmol) obtained in step 1 of example 2 and N-[(2-methyl-4-fluoro)phenyl]-N-(2-methyl-2H-tetrazol-5-ylmethyl)amine. The crude product was purified by silica gel column chromatography (developing solvent-n-hexane:ethyl acetate=2:1), to give desired compound (323 mg, yield: 40%).

¹H NMR (CDCl₃, 200 MHz): δ 1.63 (s, 3H), 2.47 (s, 3H), 3.38 (s, 3H), 3.40 (s, 3H), 3.99 (d, 1H), 4.12 (d, 1H), 4.23 (s, 1H), 4.33 (d, 1H), 4.47 (s, 1H), 4.67 (d, 1H), 4.78 (d, 1H), 6.75-6.85 (m, 2H), 7.55 (dd, 1H), 8.06 (dd, 1H), 9.02 (d, 1H).

EXAMPLE 38

Preparation of (2S,3R,4S)-6-amino-4-[N-(2-methyl-4-fluorophenyl)-N-(2-methyl-2H-tetrazol-5-ylmethyl)amino]-3-hydroxy-2-methyl-2-dimethoxymethyl-3,4-dihydro-2H-1-benzopyran The same procedure as example 10 was accomplished, except for using the compound (205 mg, 0.41 mmol) obtained in example 37. The crude product was purified by silica gel column chromatography (developing solvent-n-hexane:ethyl acetate=1:4), to give desired compound (143 mg, yield: 74%).

¹H NMR (CDCl₃, 200 MHz): δ 1.49 (s, 3H), 2.43 (s, 3H), 2.98 (d, 1H), 9.31 (s, 3H), 3.46 (s, 3H), 4.19 (s, 3H), 4.23 (d, 1H), 4.37 (d, 1H), 4.43 (s, 3H), 4.81 (d, 1H), 6.58 (dd, 1H), 6.65-6.80 (m, 3H), 7.40 (dd, 1H), 7.68 (d, 1H)

EXAMPLE 39

Preparation of (2S,3R,4S)-6-nitro-4-[N-(4-methoxyphenyl)-N-(2-methyl-2H-tetrazol-5-ylmethyl) amino]-3-hydroxy-2-methyl-2-dimethoxymethyl-3,4-dihydro-2H-1-benzopyran The same procedure as step 3 of example 1 was accomplished, except for using the epoxide compound (300 mg, 1.07 mmol) obtained in step 1 of example 2 and N-(4-methoxyphenyl)-N-(2-methyl-2H-tetrazol-5-ylmethyl)amine. The crude product was purified by silica gel column chromatography (developing solvent-n-hexane:ethyl acetate=2:1), to give desired compound (417 mg, yield: 78%).

¹H NMR (CDCl₃, 200 MHz): δ 1.62 (s, 3H), 3.48 (s, 3H), 3.54 (s,3H), 3.74 (s, 3H), 3.93 (dd, 1H), 4.32 (m, 4H), 4.72 (s, 1H), 4.83 (d, 1H), 5.34 (d, 1H), 5.46 (d, 2H), 6.76-6.95 (m, 3H), 8.03 (d, 1H), 8.08 (dd, 1H).

EXAMPLE 40

Preparation of (2S,3R,4S)-6-amino-4-[N-(4-methoxyphenyl)-N-(2-methyl-2H-tetrazol-5-ylmethyl) amino]-3-hydroxy-2-methyl-2-dimethoxymethyl-3,4-dihydro-2H-1-benzopyran The same procedure as example 10 was accomplished, except for using the compound (300 mg, 0.6 mmol) obtained in example 39. The crude product was purified by silica gel column chromatography (developing solvent-n-hexane:ethyl acetate=1:4), to give desired compound (270 mg, yield: 96%).

¹H NMR (CDCl₃, 200 MHz): δ 1.53 (s, 3H), 3.39 (s, 2H), 3.48 (s, 3H), 3.51 (s, 3H), 3.73 (s, 3H), 3.93 (dd, 1H), 4.30 (s, 3H), 4.44 (d, 1H), 4.61 (m, 1H), 4.67 (d, 1H), 5.17 (d, 1H), 6.54 (m, 1H), 6.69 (d, 1H), 6.77 (d, 2H), 6.89 (d, 2H)

EXAMPLE 41

Preparation of (2S,3R,4S)-6-nitro-4-[N-(2-methyl-4-chlorophenyl)-N-(2-methyl-2H-tetrazol-5-ylmethyl) amino]-3-hydroxy-2-methyl-2-dimethoxymethyl-3,4-dihydro-2H-1-benzopyran The same procedure as step 3 of example 1 was accomplished, except for using the epoxide compound (450 mg, 1.6 mmol) obtained in step 1 of example 2 and N-[(2-methyl-4-chlorophenyl)]-N-(2-methyl-2H-tetrazol-5-ylmethyl)amine. The crude product was purified by silica gel column chromatography (developing solvent-n-hexane:ethyl acetate=2:1), to give desired compound (235 mg, yield: 28%).

¹H NMR (CDCl₃, 200 MHz): δ 1.63 (s, 3H), 2.46 (s, 3H), 3.38 (s, 3H), 3.41 (s, 3H), 3.99-4.18 (m, 2H), 4.23 (s, 3H), 4.33 (d, 1H), 4.48 (s, 1H), 4.67 (d, 1H), 4.87 (s, 1H), 6.90 (d, 1H), 7.01-7.09 (m, 2H), 7.50 (d, 1H), 8.07 (dd, 1H), 8.99 (d, 1H).

EXAMPLE 42

Preparation of (2S,3R,4S)-6-amino-4-[N-(2-methyl-4-chlorophenyl)-N-(2-methyl-2H-tetrazol-5-ylmethyl)amino]-3-hydroxy-2-methyl-2-dimethoxymethyl-3,4-dihydro-2H-1-benzopyran The same procedure as example 10 was accomplished, except for using the compound (164 mg, 0.31 mmol) obtained in example 41. The crude product was purified by silica gel column chromatography (developing solvent-n-hexane:ethyl acetate=1:4), to give desired compound (86 mg, yield: 57%).

¹H NMR (CDCl₃, 200 MHz): δ 1.50 (s, 3H), 2.42 (s, 3H), 2.99 (d, 1H), 3.32 (s, 3H), 3.46 (s, 3H), 4.03-4.23 (m, 4H), 4.19 (s, 3H), 4.43 (s, 1H), 4.48 (d, 1H), 4.81 (d, 1H), 6.58 (dd, 1H), 6.68 (d, 1H), 6.96-7.04 (m, 2H), 7.34 (d, 1H), 7.65 (d, 1H).

EXAMPLE 43

Preparation of (2S,3R,4S)-6-nitro-4-[N-(2-methoxy-5-methylphenyl)-N-(2-methyl-2H-tetrazol-5-ylmethyl)amino]-3-hydroxy-2-methyl-2-dimethoxymethyl-3,4-dihydro-2H-1-benzopyran The same procedure as step 3 of example 1 was accomplished, except for using the epoxide compound (400 mg, 1.4 mmol) obtained in step 1 of example 2 and N-[(2-methoxy-5-methyl)phenyl]-N-(2-methyl-2H-tetrazol-5-ylmethyl) amine. The crude product was purified by silica gel column chromatography (developing solvent-n-hexane:ethyl acetate=2:1), to give desired compound (615 mg, yield: 85%).

¹H NMR (CDCl₃, 200 MHz): δ 1.64 (s, 3H), 3.37 (s, 3H), 3.50 (s, 3H), 3.93 (s, 3H), 4.13 (d, 1H), 4.23 (s, 1H), 4.75 (s, 1H), 4.85 (d, 1H), 4.68 (s, 1H), 4.99 (d, 1H), 5.76 (d, 1H), 5.79 (d, 1H), 6.80 (s, 2H), 6.87 (d, 1H), 7.35 (s, 1H), 8.02 (dd, 1H), 8.83 (d, 1H).

EXAMPLE 44

Preparation of (2S,3R,4S)-6-amino-4-[N-(2-methoxy-5-methylphenyl)-N-(2-methyl-2H-tetrazol-5-ylmethyl)amino]-3-hydroxy-2-methyl-2-dimethoxymethyl-3,4-dihydro-2H-1-benzopyran The same procedure as example 10 was accomplished, except for using the compound (414 mg, 0.8 mmol) obtained in example 43. The crude product was purified by silica gel column chromatography (developing solvent-n-hexane:ethyl acetate=1:4), to give desired compound (285 mg, yield: 74%).

$^1$H NMR (CDCl$_3$, 200 MHz): δ 1.53 (s, 3H), 2.21 (s, 3H), 3.41 (s, 3H), 3.44 (s, 3H), 3.83 (s, 3H), 4.00-4.11 (m, 2H), 4.20 (s, 3H), 4.49 (d, 1H), 4.53 (s, 1H), 4.61 (d, 1H), 4.98 (d, 1H), 6.54 (dd, 1H), 6.64-6.76 (m, 3H), 7.18 (s, 1H), 7.25 (s, 1H).

EXAMPLE 45

Preparation of (2S,3R,4S)-6-nitro-4-[N-(2,4-dimethylphenyl)-N-(2-methyl-2H-tetrazol-5-ylmethyl)amino]-3-hydroxy-2-methyl-2-dimethoxymethyl-3,4-dihydro-2H-1-benzopyran The same procedure as step 3 of example 1 was accomplished, except for using the epoxide compound (250 mg, 0.89 mmol) obtained in step 1 of example 2 and N-(2,4-dimethylphenyl)-N-(2-methyl-2H-tetrazol-5-ylmethyl)amine. The crude product was purified by silica gel column chromatography (developing solvent-n-hexane:ethyl acetate=2:1), to give desired compound (256 mg, yield: 57%).

$^1$H NMR (CDCl$_3$, 200 MHz): δ 1.62 (s, 3H), 2.23 (s, 3H), 2.46 (s, 3H), 3.39 (s, 3H), 3.40 (s, 3H), 4.12-4.16 (m, 2H), 4.22 (s, 3H), 4.40 (d, 1H), 4.51 (s, 1H), 4.64 (d, 1H), 4.89 (d, 1H), 6.87-6.94 (m, 1H), 7.48 (d, 1H), 8.05 (dd, 1H), 8.99 (dd, 1H).

EXAMPLE 46

Preparation of (2S,3R,4S)-6-amino-4-[N-(2,4-dimethylphenyl)-N-(2-methyl-2H-tetrazol-5-ylmethyl)amino]-3-hydroxy-2-methyl-2-dimethoxymethyl-3,4-dihydro-2H-1-benzopyran The same procedure as example 10 was accomplished, except for using the compound (180 mg, 0.36 mmol) obtained in example 45. The crude product was purified by silica gel column chromatography (developing solvent-n-hexane:ethyl acetate=1:4), to give desired compound (155 mg, yield: 92%).

$^1$H NMR (CDCl$_3$, 200 MHz): δ 1.49 (s, 3H), 2.20 (s, 3H), 2.42 (s, 3H), 3.10 (brs, 3H), 3.32 (s, 3H), 3.45 (s, 3H), 4.12 (d, 1H), 4.16 (s, 3H), 4.20 (d, 1H), 4.45 (s, 1H), 4.49 (d, 1H), 4.82 (d, 1H), 6.56 (dd, 1H), 6.67 (d, 1H), 6.83 (s, 1H), 6.88 (s, 1H), 7.33 (d, 1H), 7.67 (d, 1H).

EXAMPLE 47

Preparation of (2S,3R,4S)-6-nitro-4-[N-(2,6-dimethylphenyl)-N-(2-methyl-2H-tetrazol-5-ylmethyl)amino]-3-hydroxy-2-methyl-2-dimethoxymethyl-3,4-dihydro-2H-1-benzopyran The same procedure as step 3 of example 1 was accomplished, except for using the epoxide compound (300 mg, 1.1 mmol) obtained in step 1 of example 2 and N-(2,6-dimethylphenyl)-N-(2-methyl-2H-tetrazol-5-ylmethyl)amine. The crude product was purified by silica gel column chromatography (developing solvent-n-hexane:ethyl acetate=2:1), to give desired compound (153 mg, yield: 29%).

$^1$H NMR (CDCl$_3$, 200 MHz): δ 1.63 (s, 3H), 2.55 (brs, 6H), 3.13 (d, 1H), 3.30 (s, 3H), 3.40 (s, 3H), 3.62 (d, 1H), 4.15 (d, 1H), 4.22 (s, 3H), 4.37 (s, 1H), 4.62 (d, 1H), 4.93 (d, 1H), 6.89-6.94 (m, 4H), 8.05 (dd, 1H), 9.17 (d, 1H).

EXAMPLE 48

Preparation of (2S,3R,4S)-6-amino-4-[N-(2,6-dimethylphenyl)-N-(2-methyl-2H-tetrazol-5-ylmethyl)amino]-3-hydroxy-2-methyl-2-dimethoxymethyl-3,4-dihydro-2H-1-benzopyran The same procedure as example 10 was accomplished, except for using the compound (107 mg, 0.21 mmol) obtained in example 47. The crude product was purified by silica gel column chromatography (developing solvent-n-hexane:ethyl acetate=1:4), to give desired compound (78 mg, yield: 80%).

$^1$H NMR (CDCl$_3$, 200 MHz): δ 1.51 (s, 3H), 2.53 (s, 6H), 2.91 (d, 1H), 3.28 (s, 3H), 3.45 (s, 3H), 3.54 (s, 1H), 3.60 (d, 1H), 3.98-4.13 (m, 1H), 4.15 (s, 3H), 4.29 (d, 1H), 4.46 (s, 1H), 4.87 (d, 1H), 6.59 (d, 1H), 6.64 (d, 1H), 6.68-6.86 (m, 3H), 7.84 (s, 1H).

EXAMPLE 49

Preparation of (2S,3R,4S)-6-nitro-4-[N-(2,3-dimethylphenyl)-N-(2-methyl-2H-tetrazol-5-ylmethyl)amino]-3-hydroxy-2-methyl-2-dimethoxymethyl-3,4-dihydro-2H-1-benzopyran The same procedure as step 3 of example 1 was accomplished, except for using the epoxide compound (300 mg, 1.07 mmol) obtained in step 1 of example 2 and N-(2,3-dimethylphenyl)-N-(2-methyl-2H-tetrazol-5-ylmethyl)amine. The crude product was purified by silica gel column chromatography (developing solvent-n-hexane:ethyl acetate=2:1), to give desired compound (253 mg, yield: 47%).

$^1$H NMR (CDCl$_3$, 200 MHz): δ 1.63 (s, 3H), 2.26 (s, 3H), 2.40 (s, 3H), 3.38 (s, 3H), 3.39 (s, 3H), 4.04 (d, 1H), 4.13 (d, 1H), 4.21 (s, 3H), 4.40 (d, 1H), 4.49 (s, 1H), 4.67 (d, 1H), 4.89 (d, 1H), 6.85 (d, 1H), 6.89 (d, 1H), 7.02 (t, 1H), 7.47 (d, 1H), 8.06 (dd, 1H), 9.00 (d, 1H).

EXAMPLE 50

Preparation of (2S,3R,4S)-6-amino-4-[N-2,3-dimethylphenyl]-N-(2-methyl-2H-tetrazol-5-ylmethyl)amino]-3-hydroxy-2-methyl-2-dimethoxymethyl-3,4-dihydro-2H-1-benzopyran The same procedure as example 10 was accomplished, except for using the compound (177 mg, 0.35 mmol) obtained in example 49. The crude product was purified by silica gel column chromatography (developing solvent-n-hexane:ethyl acetate=1:4), to give desired compound (131 mg, yield: 80%).

H NMR (CDCl$_3$, 200 MHz): δ 1.48 (s, 3H), 2.23 (s, 3H), 2.35 (s, 3H), 2.90 (s, 1H), 3.30 (s, 3H), 3.45 (s, 3H), 4.07-4.25 (m, 2H), 4.18 (s, 3H), 4.44 (s, 1H), 4.51 (d, 1H), 4.83 (d, 1H), 6.58 (dd, 1H), 6.68 (d, 1H), 6.78 (d, 1H), 6.96 (t, 1H), 7.31 (d, 1H), 7.71 (d, 1H).

EXAMPLE 51

Preparation of (2S,3R,4S)-6-nitro-4-[N-(2-isopropylphenyl)-N-(2-methyl-2H-tetrazol-5-ylmethyl) amino]-3-hydroxy-2-methyl-2-dimethoxymethyl-3, 4-dihydro-2H-1-benzopyran The same procedure as step 3 of example 1 was accomplished, except for using the epoxide compound (300 mg, 1.07 mmol) obtained in step 1 of example 2 and N-(2-isopropylphenyl)-N-(2-methyl-2H-tetrazol-5-ylmethyl)amine. The crude product was purified by silica gel column chromatography (developing solvent-n-hexane:ethyl acetate=2:1), to give desired compound (192 mg, yield: 35%).

$^1$H NMR (CDCl$_3$, 200 MHz): δ 1.27 (d, 3H), 1.63 (s, 3H), 3.38 (s, 3H), 3.36 (s, 3H), 4.15 (d, 1H), 4.20 (s, 3H), 4.31 (d, 1H), 4.45 (s, 1H), 4.75 (d, 1H), 4.82 (d, 1H), 6.90 (d, 1H), 7.02-7.12 (m, 2H), 7.23 (d, 1H), 7.60 (dd, 1H), 8.07 (dd, 1H), 9.02 (dd, 1H).

EXAMPLE 52

Preparation of (2S,3R,4S)-6-amino-4-[N-(2-isopropylphenyl)-N-(2-methyl-2H-tetrazol-5-ylmethyl) amino]-3-hydroxy-2-methyl-2-dimethoxymethyl-3, 4-dihydro-2H-1-benzopyran The same procedure as example 10 was accomplished, except for using the compound (140 mg, 0.27 mmol) obtained in example 51. The crude product was purified by silica gel column chromatography (developing solvent-n-hexane:ethyl acetate=1:4), to give desired compound (83 mg, yield: 64%).

$^1$H NMR (CDCl$_3$, 200 MHz): δ 1.23 (d, 3H), 1.27 (d, 3H), 1.49 (s, 3H), 2.90 (brs, 1H), 3.27 (s, 3H), 3.44 (s, 3H), 3.61 (m, 1H), 4.10-4.20 (m, 4H), 4.41 (s, 1H), 4.44 (d, 1H), 4.88 (d, 1H), 6.59 (dd, 1H), 6.68 (d, 1H), 6.95-7.06 (m, 2H), 7.19 (dd, 1H), 7.48 (dd, 1H), 7.65 (d, 1H).

EXAMPLE 53

Preparation of (2S,3R,4S)-6-nitro-4-[N-(4-ethoxycarbonylphenyl)-N-(2-methyl-2H-tetrazol-5-ylmetyl) amino]-3-hydroxy-2-methyl-2-dimethoxymethyl-3, 4-dihydro-2H-1-benzopyran The same procedure as step 3 of example 1 was accomplished, except for using the epoxide compound (400 mg, 1.42 mmol) obtained in step 1 of example 2 and N-[(4-ethoxycarbonyl)phenyl]-N-(2-methyl-2H-tetrazol-5-ylmethyl)amine. The crude product was purified by silica gel column chromatography (developing solvent-n-hexane:ethyl acetate=2:1), to give desired compound (161 mg, yield: 33%).

$^1$H NMR (CDCl$_3$, 200 MHz): δ 1.35 (t, 3H), 1.63 (s, 3H), 3.52 (s, 3H), 3.55 (s, 3H), 3.92 (s, 1H), 4.33 (m, 6H), 4.51-4.75 (m, 2H), 4.91 (d, 1H), 5.49 (s, 1H), 5.81 (d, 1H), 6.89-6.99 (m, 3H), 7.87-8.10 (m, 4H).

EXAMPLE 54

Preparation of (2S,3R,4S)-6-amino-4-[N-(4-ethoxycarbonylphenyl)-N-(2-methyl-2H-tetrazol-5-ylmethyl)amino]-3-hydroxy-2-methyl-2-dimethoxymethyl-3,4-dihydro-2H-1-benzopyran The same procedure as example 10 was accomplished, except for using the compound (118 mg, 0.22 mmol) obtained in example 53. The crude product was purified by silica gel column chromatography (developing solvent-n-hexane:ethyl acetate=1:4), to give desired compound (49 mg, yield: 44%).

$^1$H NMR (CDCl$_3$, 200 MHz): δ 1.33 (t, 3H), 1.54 (s, 3H), 3.25 (s, 1H), 3.49 (s, 3H), 3.52 (s, 3H), 3.99 (s, 1H), 4.24-4.42 (m, 5H), 4.64-4.81 (m, 3H), 5.58 (s, 1H), 6.53 (dd, 1H), 6.70 (d, 1H), 6.89 (d, 2H), 7.87 (d, 2H).

EXAMPLE 55

Preparation of (2S,3R,4S)-6-amino-4-[N-(2-methyl-2H-tetrazol-5-ylmethyl)phenylamino]-3-hydroxy-2-methyl-2-dimethoxymethyl-3,4-dihydro-2H-1-benzopyran The same procedure as example 10 was accomplished, except for using the compound (217 mg, 0.46 mmol) obtained in example 4. The crude product was purified by silica gel column chromatography (developing solvent-n-hexane:ethyl acetate=1:4), to give desired compound (157 mg, yield: 77%).

$^1$H NMR (CDCl$_3$, 200 MHz): δ 1.54 (s, 3H), 3.30 (s, 1H), 3.49 (s, 3H), 3.52 (s, 3H), 3.96 (d, 1H), 4.30 (s, 3H), 4.45 (d; 1H), 4.64 (s, 1H), 4.71 (d, 1H), 5.43 (d, 1H), 6.46 (s, 1H), 6.52 (dd, 1H), 6.69 (d, 1H), 6.76 (d, 1H), 6.90 (d, 1H), 7.25 (t, 2H).

EXAMPLE 56

Preparation of (2S,3R,4S)-6-amino-4-[N-(4-fluorophenyl)-N-(2-methyl-2H-tetrazol-5-ylmethyl) amino]-3-hydroxy-2-methyl-2-dimethoxymethyl-3, 4-dihydro-2H-1-benzopyran The same procedure as example 10 was accomplished, except for using the compound (104 mg, 0.21 mmol) obtained in example 6. The crude product was purified by silica gel column chromatography (developing solvent-n-hexane:ethyl acetate=1:4), to give desired compound (85 mg, yield: 88%).

$^1$H NMR (CDCl$_3$, 200 MHz): δ 1.53 (s, 3H), 3.48 (s, 3H), 3.51 (s, 3H), 3.96 (d, 1H), 4.29 (s, 3H), 4.44 (d, 1H), 4.61 (s, 1H), 4.67 (d, 1H), 5.26 (d, 1H), 6.53 (d, 2H), 6.69 (d, 1H), 6.85 (d, 2H), 6.88 (d, 2H).

EXAMPLE 57

Preparation of (2S,3R,4S)-6-amino-4[N-benzyl-N-(2-methyl-2H-tetrazol-5-ylmethyl)amino]-3-hydroxy-2-methyl-2-dimethoxymethyl-3,4-dihydro-2H-1-benzopyran The same procedure as example 10 was accomplished, except for using the compound (75 mg, 0.15 mmol) obtained in example 8. The crude product was purified by silica gel column chromatography (developing solvent-n-hexane:ethyl acetate=1:4), to give desired compound (57 mg, yield: 87%).

$^1$H NMR (CDCl$_3$, 200 MHz): δ 1.51 (s, 3H), 3.22 (s, 3H), 3.39 (s, 3H), 3.61 (d, 1H), 3.83 (d, 1H), 3.92 (d, 1H), 4.02 (d, 1H), 4.12-4.27 (m, 3H), 4.31 (s, 3H), 6.52 (dd, 1H), 6.59 (d, 1H), 7.22-7.37 (m, 4H), 7.48 (d, 2H).

EXAMPLE 58

Preparation of (2S,3R,4S)-6-nitro-4-[N-(3-methoxycarbonylphenyl)-N-(2-methyl-2H-tetrazol-5-ylmethyl)amino]-3-hydroxy-2-methyl-2-dimethoxymethyl-3,4-dihydro-2H-1-benzopyran The same procedure as step 3 of example 1 was accomplished, except for using the epoxide compound (460 mg, 1.65 mmol) obtained in step 1 of example 2 and N-[(3-methoxycarbonyl)phenyl]-N-(2-methyl-2H-tetrazol-5-ylmethyl) amine. The crude product was purified by silica gel column chromatography (developing solvent-n-hexane:ethyl acetate=2:1), to give desired compound (360 mg, yield: 40%).

$^1$H NMR (CDCl$_3$, 200 MHz): δ 1.22 (s, 3H), 3.57 (s, 3H), 3.89 (s, 3H), 4.13 (m, 2H), 4.30 (s, 3H), 4.88 (s, 1H), 6.98 (m, 2H), 7.27 (d, 1H), 7.30 (d, 1H), 7.69 (1H), 7.96 (m, 1H), 8.07 (dd, 1H).

EXAMPLE 59

Preparation of (2S,3R,4S)-6-amino-4-[N-(3-methoxycarbonylphenyl)-N-(2-methyl-2H-tetrazol-5-ylmethyl)amino]-3-hydroxy-2-methyl-2-methoxymethyl-3,4-dihydro-2H-1-benzopyran The same procedure as example 10 was accomplished, except for using the compound (520 mg, 0.57 mmol) obtained in example 58. The crude product was purified by silica gel column chromatography (developing solvent-n-hexane:ethyl acetate=1:2), to give desired compound (360 mg, yield: 40%).

$^1$H NMR (CDCl$_3$, 200 MHz): δ 1.53 (s, 3H), 3.59 (d, 6H), 3.84 (s, 3H), 3.98 (m, 2H), 4.12 (s, 3H), 4.15 (m, 1H), 4.78 (s, 1H), 5.55 (m, 1H), 6.66 (m, 2H), 6.71 (d, 1H), 7.01 (m, 1H), 7.17 (t, 1H), 7.38 (m, 1H), 7.68 (m, 1H).

EXAMPLE 60

Preparation of (2S,3R,4S)-6-nitro-4-[N-(2-hydroxyphenyl)-N-(2-methyl-2H-tetrazol-5-ylmethyl)amino]-3-hydroxy-2-methyl-2-dimethoxymethyl-3,4-dihydro-2H-1-benzopyran The same procedure as step 3 of example 1 was accomplished, except for using the epoxide compound (370 mg, 1.32 mmol) obtained in step 1 of example 2 and N-(2-hydroxyphenyl)-N-(2-methyl-2H-tetrazol-5-ylmethyl)amine. The crude product was purified by silica gel column chromatography (developing solvent-n-hexane:ethyl acetate=1:2), to give desired compound (140 mg, yield: 21%).

$^1$H NMR (CDCl$_3$, 200 MHz): δ 1.66 (s, 3H), 3.44 (d, 6H), 4.13 (m, 2H), 4.33 (s, 3H), 4.81 (s, 1H), 4.91 (m, 1H), 4.99 (m, 1H), 6.99 (m, 1H), 7.55 (m, 1H), 8.02 (dd, 1H), 8.54 (dd, 1H).

EXAMPLE 61

Preparation of (2S,3R,4S)-6-amino-4-[N-(2-hydroxyphenyl)-N-(2-methyl-2H-tetrazol-5-ylmethyl)amino]-3-hydroxy-2-methyl-2-dimethoxymethyl-3,4-dihydro-2H-1-benzopyran The same procedure as example 10 was accomplished, except for using the compound (210 mg, 0.42 mmol) obtained in example 60. The crude product was purified by silica gel column chromatography (developing solvent-n-hexane:ethyl acetate=1:4), to give desired compound (71 mg, yield: 37%).

$^1$H NMR (CDCl$_3$, 200 MHz): δ 1.57 (s, 3H), 3.55 (d, 6H), 4.15 (m, 2H), 4.33 (s, 3H), 4.44 (s, 1H), 4.75 (m, 1H), 4.84 (m, 1H), 6.86 (m, 6H) 7.49 (m, 1H).

EXAMPLE 62

Preparation of (2S,3R,4S)-6-nitro-4-[N-(2-methoxy-4-methoxycarbonylphenyl)-N-(2-methyl-2H-tetrazol-5-ylmethyl)amino]-3-hydroxy-2-methyl-2-dimethoxymethyl-3,4-dihydro-2H-1-benzopyran The same procedure as step 3 of example 1 was accomplished, except for using the epoxide compound (380 mg, 1.36 mmol) obtained in step 1 of example 2 and N-[(2-methoxy-4-methoxycarbonyl)phenyl]-N-(2-methyl-2H-tetrazol-5-ylmethyl)amine. The crude product was purified by silica gel column chromatography (developing solvent-n-hexane:ethyl acetate=1:3), to give desired compound (250 mg, yield: 48%).

$^1$H NMR (CDCl$_3$, 200 MHz): δ 1.64 (s, 3H), 3.48 (d, 6H), 3.90 (s, 3H), 4.01 (s, 3H), 4.33 (m, 2H), 4.66 (s, 1H), 4.99 (m, 1H), 5.19 (m, 1H), 6.92 (d, 1H), 7.55 (m, 3H), 8.02 (dd, 1H), 8.74 (,m, 1H).

EXAMPLE 63

Preparation of (2S,3R,4S)-6-amino-4-[N-(2-methoxy-4-methoxycarbonylphenyl)-N-(2-methyl-2H-tetrazol-5-ylmethyl)amino]-3-hydroxy-2-methyl-2-dimethoxymethyl-3,4-dihydro-2H-1-benzopyran The same procedure as example 10 was accomplished, except for using the compound (200 mg, 0.37 mmol) obtained in example 62. The crude product was purified by silica gel column chromatography (developing solvent-n-hexane:ethyl acetate=1:4), to give desired compound (90 mg, yield: 45%).

$^1$H NMR (CDCl$_3$, 200 MHz): δ 1.52 (s, 3H), 3.42 (d, 6H), 3.58 (m, 1H), 3.75 (s, 3H), 3.77 (s, 3H), 3.98 (m, 1H), 4.49 (s, 1H), 4.57 (m, 1H), 4.68 (m, 1H), 5.26 (d, 1H), 6.57 (m, 1H), 7.27 (m, 2H), 7.55 (m, 2H).

EXAMPLE 64

Preparation of (2S,3R,4S)-6-nitro-4-[N-(2-methyl-4-hydroxyphenyl)-N-(2-methyl-2H-tetrazol-5-ylmethyl)amino]-3-hydroxy-2-methyl-2-dimethoxymethyl-3,4-dihydro-2H-1-benzopyran The same procedure as step 3 of example 1 was accomplished, except for using the epoxide compound (350 mg, 1.26 mmol) obtained in step 1 of example 2 and N-[(2-methyl-4-hydroxy)phenyl]-N-(2-methyl-2H-tetrazol-5-ylmethyl)amine. The crude product was purified by silica gel column chromatography (developing solvent-n-hexane:ethyl acetate=1:2), to give desired compound (190 mg, yield: 30%).

$^1$H NMR (CDCl$_3$, 200 MHz): δ 1.61 (s, 3H), 2.43 (s, 6H), 3.39 (d, 6H,) 3.64 (m, 1H), 3.96 (m, 1H), 4.16 (s, 1H), 4.46 (s, 1H), 4.68 (m, 1H), 4.72 (m, 1H), 5.81 (brs, 1H), 6.59 (dd, 1H), 6.61 (m, 1H), 6.91 (d, 1H), 7.27 (d, 1H), 8.04 (dd, 1H), 9.05 (m, 1H).

EXAMPLE 65

Preparation of (2S, 3R,4S)-6-amino-4-[N-(2methyl-4-hydroxyphenyl)-N-(2-methyl-2H-tetrazol-5-ylmethyl)amino]-3-hydroxy-2-methyl-2-dimethoxymethyl-3,4-dihydro-2H-1-benzopyran The same procedure as example 10 was accomplished, except for using the compound (140 mg, 0.29 mmol) obtained in example 64. The crude product was purified by silica gel column chromatography (developing solvent-n-hexane:ethyl acetate=1:4), to give desired compound (70 mg, yield: 53%).

$^1$H NMR (CDCl$_3$, 200 MHz): δ 1.48 (s, 3H), 2.32 (s, 3H), 3.31 (d, 6H,) 3.63 (m, 1H), 3.78 (m, 1H), 4.10 (s, 3H), 4.23 (m, 1H), 4.33 (s, 1H), 4.82 (m, 1H), 6.34 (dd, 1H), 6.59 (m, 3H), 7.26 (m, 1H), 7.71 (m, 1H).

EXAMPLE 66

Preparation of (2S,3R,4S)-6-nitro-4-[N-(2-ethylphenyl)-N-(2-methyl-2H-tetrazol-5-ylmethyl)amino]-3-hydroxy-2-methyl-2-dimethoxymethyl-3,4-dihydro-2H-1-benzopyran The same procedure as step 3 of example 1 was accomplished, except for using the epoxide compound (270 mg, 0.98 mmol) obtained in step 1 of example 2 and N-(2-ethylphenyl)-N-(2-methyl-2H-tetrazol-5-ylmethyl)amine. The crude product was purified by silica gel column chromatography (developing solvent-n-hexane:ethyl acetate=1:2), to give desired compound (100 mg, yield: 22%).

$^1$H NMR (CDCl$_3$, 200 MHz): δ 1.27 (t, 3H), 1.62 (s, 3H), 2.89 (t, 2H,) 3.36 (d, 6H), 3.82 (d, 1H), 4.10 (d, 1H), 4.18 (s, 3H), 4.28 (d, 1H), 4.35 (s, 1H), 4.84 (d, 1H), 7.10 (m, 4H), 7.59 (dd, 1H), 8.08 (dd, 1H), 9.02 (m, 1H).

EXAMPLE 67

Preparation of (2S,3R,4S)-6-amino-4-[N-(2-ethylphenyl)-N-(2-methyl-2H-tetrazol-5-ylmethyl)amino]-3-hydroxy-2-methyl-2-dimethoxymethyl-3,4-dihydro-2H-1-benzopyran The same procedure as example 10 was accomplished, except for using the compound (190 mg, 0.39 mmol) obtained in example 66. The crude product was purified by silica gel column chromatography (developing solvent-n-hexane:ethyl acetate=1:4), to give desired compound (30 mg, yield: 14%).

$^1$H NMR (CDCl$_3$, 200 MHz): δ 1.24 (t, 3H), 1.49 (s, 3H), 2.65 (m, 1H,) 2.91 (m, 1H), 3.27 (d, 6H), 4.09 (m, 2H), 4.14 (s, 3H), 4.42 (s, 1H), 4.45 (m, 1H), 4.92 (m, 1H), 6.70 (m, 2H), 7.05 (m, 3H), 7.45 (d, 1H), 7.67 (m, 1H).

EXAMPLE 68

Preparation of (2S,3R,4S)-6-nitro-4-[N-(2-methyl-5-methoxycarbonylphenyl)-N-(2-methyl-2H-tetrazol-5-ylmethyl)amino]-3-hydroxy-2-methyl-2-dimethoxymethyl-3,4-dihydro-2H-1-benzopyran The same procedure as step 3 of example 1 was accomplished, except for using the epoxide compound (420 mg, 1.48 mmol) obtained in step 1 of example 2 and N-(2-methyl-5-(methoxycarbonyl)phenyl)-N-(2-methyl-2H-tetrazol-5-ylmethyl)amine. The crude product was purified by silica gel column chromatography (developing solvent-n-hexane:ethyl acetate=1:2), to give desired compound (520 mg, yield: 51%).

$^1$H NMR (CDCl$_3$, 200 MHz): δ 1.64 (s, 1H), 2.56 (s, 3H), 3.41 (d, 6H,) 3.87 (s, 3H), 4.07 (m, 2H), 4.10 (s, 3H), 4.48 (s, 1H), 4.80 (d, 1H), 4.93 (d, 1H), 6.93 (d, 1H), 7.17 (d, 1H), 7.61 (m, 1H), 8.07 (dd, 1H), 8.25 (m, 1H), 8.97 (m, 1H)

EXAMPLE 69

Preparation of (2S,3R,4S)-6-amino-4-[N-(2-methyl-5-methoxycarbonylphenyl)-N-(2-methyl-2H-tetrazol-5-ylmethyl)amino]-3-hydroxy-2-methyl-2-dimethoxymethyl-3,4-dihydro-2H-1-benzopyran The same procedure as example 10 was accomplished, except for using the compound (220 mg, 0.40 mmol) obtained in example 68. The crude product was purified by silica gel column chromatography (developing solvent-n-hexane:ethyl acetate=1:4), to give desired compound (90 mg, yield: 44%).

$^1$H NMR (CDCl$_3$, 200 MHz): δ 1.48 (s, 3H), 2.49 (s, 3H), 3.44 (d, 6H,) 3.72 (m, 1H), 3.83 (m, 1H), 4.05 (s, 3H), 4.49 (s, 1H), 4.54 (d, 1H), 4.96 (d, 1H), 6.68 (m, 2H), 7.25 (d, 1H), 7.49 (m, 2H), 8.05 (m, 1H).

EXAMPLE 70

Preparation of (2S,3R,4S)-6-nitro-4-[N-(2-hydroxy-5-methylphenyl)-N-(2-methyl-2H-tetrazol-5-ylmethyl)amino]-3-hydroxy-2-methyl-2-dimethoxymethyl-3,4-dihydro-2H-1-benzopyran The same procedure as step 3 of example 1 was accomplished, except for using the epoxide compound (400 mg, 1.43 mmol) obtained in step 1 of example 2 and N-(2-hydroxy-5-methylphenyl)-N-(2-methyl-2H-tetrazol-5-ylmethyl)amine. The crude product was purified by silica gel column chromatography (developing solvent-n-hexane:ethyl acetate=1:2), to give desired compound (280 mg, yield: 39%).

$^1$H NMR (CDCl$_3$, 200 MHz): δ 1.67 (s, 3H), 2.33 (s, 3H), 3.46 (d, 6H,) 4.07 (m, 2H), 4.25 (s, 3H), 4.87 (s, 1H), 4.86 (d, 1H), 4.93 (d, 1H), 6.80 (s, 1H), 6.94 (d, 1H), 7.39 (m, 1H), 8.07 (dd, 1H), 8.33 (m, 1H), 8.53 (m, 1H).

EXAMPLE 71

Preparation of (2S,3R,4S)-6-amino-4-[N-(2-hydroxy-5-methylphenyl)-N-(2-methyl-2H-tetrazol-5-ylmethyl)amino]-3-hydroxy-2-methyl-2-dimethoxymethyl-3,4-dihydro-2H-1-benzopyran The same procedure as example 10 was accomplished, except for using the compound (140 mg, 0.29 mmol) obtained in example 70. The crude product was purified by silica gel column chromatography (developing solvent-n-hexane:ethyl acetate=1:4), to give desired compound (70 mg, yield: 53%).

$^1$H NMR (CDCl$_3$, 200 MHz): δ 1.62 (s, 3H), 2.33 (s, 3H), 3.30 (d, 6H,) 3.62 (m, 1H), 3.74 (m, 1H), 3.78 (s, 3H), 4.17 (m, 1H), 4.33 (s, 1H), 4.82 (d, 1H), 6.35 (m, 1H), 6.59 (m, 3H), 7.22 (m, 1H), 7.71 (m, 1H).

EXAMPLE 72

Preparation of (2S,3R,4S)-6-nitro-4-[N-(2,4,6-trimethylphenyl)-N-(2-methyl-2H-tetrazol-5-ylmethyl)amino]-3-hydroxy-2-methyl-2-dimethoxymethyl-3,4-dihydro-2H-1-benzopyran The same procedure as step 3 of example 1 was accomplished, except for using the epoxide compound (400 mg, 1.43 mmol) obtained in step 1 of example 2 and N-(2,4,6-trimethylphenyl)-N-(2-methyl-2H-tetrazol-5-ylmethyl)amine. The crude product was purified by silica gel column chromatography (developing solvent-n-hexane:ethyl acetate=1:2), to give desired compound (260 mg, yield: 35%).

$^1$H NMR (CDCl$_3$, 200 MHz): δ 1.62 (s, 3H), 2.20 (s, 3H), 2.49 (m, 6H,) 3.30 (d, 6H), 3.68 (m, 2H), 4.10 (m, 1H), 4.17 (s, 3H), 4.20 (s, 1H), 4.68 (m, 1H), 4.93 (m, 1H), 6.88 (m, 2H), 6.93 (d, 1H), 8.07 (dd, 1H), 9.14 (m, 1H).

EXAMPLE 73

Preparation of (2S,3R,4S)-6-amino-4-[N-(2,4,6-trimethylphenyl)-N-(2-methyl-2H-tetrazol-5-ylmethyl) amino]-3-hydroxy-2-methyl-2-dimethoxymethyl-3,4-dihydro-2H-1-benzopyran The same procedure as example 10 was accomplished, except for using the compound (190 mg, 0.37 mmol) obtained in example 72. The crude product was purified by silica gel column chromatography (developing solvent-n-hexane:ethyl acetate=1:4), to give desired compound (90 mg, yield: 52%).

$^1$H NMR (CDCl$_3$, 200 MHz): δ 1.64 (s, 3H), 2.17 (s, 3H), 2.52 (m, 6H,) 3.31 (d, 6H), 3.65 (m, 2H), 4.07 (s, 3H), 4.30 (m, 1H), 4.47 (s, 1H), 4.89 (m, 1H), 6.56 (m, 1H), 6.73 (m, 3H), 7.84 (m, 1H).

EXAMPLE 74

Preparation of (2S,3S,4R)-6-nitro-4-[N-(4-trifluoromethylphenyl)-N-(2-methyl-2H-tetrazol-5-ylmethyl)amino]-3-hydroxy-2-methyl-2-dimethoxymethyl-3,4-dihydro-2H-1-benzopyran The same procedure as step 3 of example 1 was accomplished, except for using the epoxide compound (340 mg, 1.21 mmol) obtained in step 1 of example 1 and N-(4-trifluoromethylphenyl)-N-(2-methyl-2H-tetrazol-5-ylmethyl) amine. The crude product was purified by silica gel column chromatography (developing solvent-n-hexane:ethyl acetate=2:1), to give desired compound (522 mg, yield: 82%).

$^1$H NMR (CDCl$_3$, 200 MHz): δ 1.50 (s, 3H), 3.59 (s, 3H), 3.63 (s, 3H,) 4.38 (s, 5H), 4.60 (s, 1H), 4.90 (m, 1H), 5.30 (m, 2H), 7.00 (m, 3H), 7.43 (m, 2H), 8.10 (m, 2H).

EXAMPLE 75

Preparation of (2S,3S,4R)-6-amino-4-[N-(4-trifluoromethylphenyl)-N-(2-methyl-2H-tetrazol-5-ylmethyl)amino]-3-hydroxy-2-methyl-2-dimethoxymethyl-3,4-dihydro-2H-1-benzopyran The same procedure as example 10 was accomplished, except for using the compound (200 mg, 0.37 mmol) obtained in example 74. The crude product was purified by silica gel column chromatography (developing solvent-n-hexane:ethyl acetate=1:2), to give desired compound (155 mg, yield: 81%).

$^1$H NMR (CDCl$_3$, 200 MHz): δ 1.50 (s, 3H), 3.63 (s, 3H), 3.68 (s, 3H,) 4.40 (s, 5H), 4.63 (s, 1H), 4.80 (m, 1H), 4.98 (m, 1H), 5.20 (m, 1H), 6.50 (m, 1H), 6.63 (m, 1H), 6.90 (d, 1H), 7.00 (m, 2H), 7.50 (m, 2H).

EXAMPLE 76

Preparation of (2R,3S,4R)-6-nitro-4-[N-(4-trifluoromethylphenyl)-N-(2-methyl-2H-tetrazol-5-ylmethyl)amino]-3-hydroxy-2-methyl-2-dimethoxymethyl-3,4-dihydro-2H-1-benzopyran Step 1: Preparation of (2R,3S,4S)-6-nitro-2-methyl-2-dimethoxymethyl-3,4-epoxy-3,4-dihydro-2H-1-benzopyran The same procedure as step 1 of example 1 was accomplished, except for using (2R)-6-nitro-2-methyl-2-dimethoxymethyl-2H-1-benzopyran (1.5 g, 5.7 mmol). The crude product was purified by silica gel column chromatography (developing solvent-n-hexane:ethyl acetate=4:1), to give desired compound (1.3 g, yield: 82%).

$^1$H NMR (CDCl$_3$, 200 MHz): δ 1.28 (s, 3H), 3.60 (s, 3H), 3.67 (s, 3H), 3.80 (d, 1H), 3.97 (d, 1H), 4.47 (s, 1H), 6.94 (d, 1H,) 8.15 (dd, 1H), 8.30 (d, 1H)

Step 2: Preparation of (2R,3S,4R)-6-nitro-4-[N-(4-trifluoromethylphenyl)-N-(2-methyl-2H-tetrazol-5-ylmethyl) amino]-3-hydroxy-2-methyl-2-dimethoxymethyl-3,4-dihydro-2H-1-benzopyran The same procedure as step 3 of example 1 was accomplished, except for using epoxide compound (426 mg, 1.51 mmol) obtained in the above step 1 and N-(4-trifluoromethylphenyl)-N-(2-methyl-2H-tetrazol-5-ylmethyl)amine (391 mg, 1.51 mmol). The crude product was purified by silica gel column chromatography (developing solvent-n-hexane:ethyl acetate=2:1), to give desired compound (111 mg, yield: 14%).

$^1$H NMR (CDCl$_3$, 200 MHz): δ 1.63 (s, 3H), 3.50 (s, 3H), 3.55 (s, 3H,) 3.92 (q, 1H), 4.30 (brs, 1H), 4.35 (s, 3H), 4.73 (s, 1H), 4.85 (d, 1H), 5.47 (s, 1H), 5.62 (d, 2H), 6.86 (d, 2H), 6.96 (d, 1H), 7.07 (d, 2H), 7.99 (s, 1H), 8.07 (dd, 1H).

EXAMPLE 77

Preparation of (2R,3S,4R)-6-amino-4-[N-(4-trifluoromethylphenyl)-N-(2-methyl-2H-tetrazol-5-ylmethyl)amino]-3-hydroxy-2-methyl-2-dimethoxymethyl-3,4-dihydro-2H-1-benzopyran The same procedure as example 10 was accomplished, except for using the compound (93 mg, 0.17 mmol) obtained in example 76. The crude product was purified by silica gel column chromatography (developing solvent-n-hexane:ethyl acetate=1:4), to give desired compound (73 mg, yield: 84%).

$^1$H NMR (CDCl$_3$, 200 MHz): δ 1.54 (s, 3H), 3.48 (s, 3H), 3.52 (s, 3H,) 3.95 (q, 1H), 4.32 (s, 1H), 4.41 (d, 1H), 4.66-4.74 (m, 3H), 5.36 (d, 1H), 6.46 (s, 1H), 6.54 (dd, 1H), 6.70 (d, 1H), 6.86 (d, 2H), 7.03 (d, 2H).

EXAMPLE 78

Preparation of (2R,3R,4S)-6-nitro-4-[N-(4-trifluoromethylphenyl)-N-(2-methyl-2H-tetrazol-5-ylmethyl)amino]-3-hydroxy-2-methyl-2-dimethoxymethyl-3,4-dihydro-2H-1-benzopyran Step 1: Preparation of (2R,3R,4R)-6-nitro-2-methyl-2-dimethoxymethyl-3,4-epoxy-3,4-dihydro-2H-1-benzopyran The same procedure as step 1 of example 2 was accomplished, except for using (2R)-6-nitro-2-methyl-2-dimethoxymethyl-2H-1-benzopyran (2.5 g, 9.4 mmol). The crude product was purified by silica gel column chromatography (developing solvent-n-hexane:ethyl acetate=4:1), to give desired compound (2.3 g, yield: 87%).

$^1$H NMR (CDCl$_3$, 200 MHz): δ 1.56 (s, 3H), 3.28 (s, 3H), 3.49 (s, 3H,) 3.82 (d, 1H), 3.99 (d, 1H), 4.21 (s, 1H), 6.85 (d, 1H), 8.13 (dd, 1H), 8.28 (d, 1H).

Step 2: Preparation of (2R,3R,4S)-6-nitro-4-[N-(4-trifluoromethylphenyl)-N-(2-methyl-2H-tetrazol-5-ylmethyl) amino]-3-hydroxy-2-methyl-2-dimethoxymethyl-34-dihydro-2H-1-benzopyran The same procedure as step 3 of example 1 was accomplished, except for using epoxide compound (604 mg, 2.15 mmol) obtained in the above step 1 and N-(4-trifluoromethylphenyl)-N-(2-methyl-1H-tetrazol-5-ylmethyl)amine (555 mg, 2.15 mmol). The crude product was purified by silica gel column chromatography (developing solvent-n-hexane:ethyl acetate=2:1), to give desired compound (700 mg, yield: 60%).

$^1$H NMR (CDCl$_3$, 200 MHz): δ 1.50 (s, 3H), 3.58 (s, 3H), 3.65 (s, 3H,) 4.38 (m, 5H), 4.60 (s, 1H), 4.90 (m, 1H), 5.30 (m, 2H), 7.05 (d, 1H), 7.01 (m, 1H), 7.43 (d, 2H), 8.10 (dd, 1H).

EXAMPLE 79

Preparation of (2R,3R,4S)-6-amino-4-[N-(4-trifluoromethylphenyl)-N-(2-methyl-2H-tetrazol-5-ylmethyl)amino]-3-hydroxy-2-methyl-2-dimethoxymethyl-3,4-dihydro-2H-1-benzopyran The same procedure as example 10 was accomplished, except for using the compound (376 mg, 0.70 mmol) obtained in example 78. The crude product was purified by silica gel column chromatography (developing solvent-n-hexane:ethyl acetate=1:3), to give desired compound (284 mg, yield: 80%).

$^1$H NMR (CDCl$_3$, 200 MHz): δ 1.42 (s, 3H), 3.56 (s, 3H), 3.62 (s, 3H,) 4.40 (s, 5H), 4.63 (s, 1H), 4.80 (m, 1H), 4.98 (m, 1H), 5.20 (m, 1H), 6.50 (m, 1H), 6.63 (m, 1H), 6.90 (d, 1H), 7.00 m, 2H), 7.50 (m, 2H).

EXAMPLE 80

Preparation of (2S,3S,4R)-6-nitro-4-[N-(4-trifluoromethoxyphenyl)-N-(2-methyl-2H-tetrazol-5-ylmethyl)amino]-3-hydroxy-2-methyl-2-dimethoxymethyl-3,4-dihydro-2H-1-benzopyran The same procedure as step 3 of example 1 was accomplished, except for using epoxide compound (293 mg, 1.04 mmol) obtained in the step 1 of example 1 and N-(4trifluoromethoxyphenyl)-N-(2-methyl-1H-tetrazol-5-ylmethyl)amine (285 mg, 1.04 mmol). The crude product was purified by silica gel column chromatography (developing solvent-n-hexane:ethyl acetate=2:1), to give desired compound (433 mg, yield: 75%).

$^1$H NMR (CDCl$_3$, 200 MHz): δ 1.45 (s, 3H), 3.59 (s, 3H), 3.63 (s, 3H,) 4.34 (s, 3H), 4.40 (m, 2H), 4.63 (s, 1H), 4.83 (d, 1H), 5.19 (m, 2H), 6.87 (m, 2H), 7.04 (m, 3H), 8.08 (m, 2H).

EXAMPLE 81

Preparation of (2S,3S,4R)-6-amino-4-[N-(4-trifluoromethoxyphenyl)-N-(2-methyl-2H-tetrazol-5-ylmethyl)amino]-3-hydroxy-2-methyl-2-dimethoxymethyl-3,4-dihydro-2H-1-benzopyran The same procedure as example 10 was accomplished, except for using the compound (240 mg, 0.43 mmol) obtained in example 80. The crude product was purified by silica gel column chromatography (developing solvent-n-hexane:ethyl acetate=1:4), to give desired compound (189 mg, yield: 83%).

$^1$H NMR (CDCl$_3$, 200 MHz): δ 1.43 (s, 3H), 3.60 (s, 3H), 3.63 (s, 3H,) 4.39 (s, 3H), 4.40 (m, 2H), 4.60 (s, 1H), 4.76 (d, 2H), 4.90 (s, 1H), 5.16 (m, 1H), 6.43 (s, 1H), 6.59 (m, 1H), 6.88 (m, 3H), 7.18 (m, 2H).

EXAMPLE 82

Preparation of (2R,3R,4S)-6-nitro-4-[N-(4-trifluoromethoxyphenyl)-N-(2-methyl-2H-tetrazol-5-ylmethyl)amino]-3-hydroxy-2-methyl-2-dimethoxymethyl-3,4-dihydro-2H-1-benzopyran The same procedure as step 3 of example 1 was accomplished, except for using epoxide compound (260 mg, 0.92 mmol) obtained in the said step 1 of example 78 and N-(4-trifluoromethoxyphenyl)-N-(2-methyl-1H-tetrazol-5-ylmethyl)amine (253 mg, 0.92 mmol). The crude product was purified by silica gel column chromatography (developing solvent-n-hexane:ethyl acetate=2:1), to give desired compound (406 mg, yield: 80%).

$^1$H NMR (CDCl$_3$, 200 MHz): δ 1.45 (s, 3H), 3.59 (s, 3H), 3.63 (s, 3H,) 4.34 (d, 3H), 4.40 (m, 2H), 4.63 (s, 1H), 4.83 (d, 1H), 5.19 (m, 2H), 6.87 (m, 2H), 7.04 (m, 3H), 8.08 (m, 2H).

EXAMPLE 83

Preparation of (2R,3R,4S)-6-amino-4-[N-(4-trifluoromethoxyphenyl)-N-(2-methyl-2H-tetrazol-5-ylmethyl)amino]-3-hydroxy-2-methyl-2-dimethoxymethyl-3,4-dihydro-2H-1-benzopyran The same procedure as example 10 was accomplished, except for using the compound (240 mg, 0.43 mmol) obtained in example 82. The crude product was purified by silica gel column chromatography (developing solvent-n-hexane:ethyl acetate=1:4), to give desired compound (176 mg, yield: 78%).

$^1$H NMR (CDCl$_3$, 200 MHz): δ 1.40 (s, 3H), 3.56 (s, 3H), 3.61 (s, 3H,) 4.37 (s, 3H), 4.40 (m, 2H), 4.60 (s, 1H), 4.76 (d, 2H), 4.90 (s, 1H), 5.16 (m, 1H), 6.43 (s, 1H), 6.59 (m, 1H), 6.88 (m, 3H), 7.18 (m, 2H).

EXAMPLE 84

Preparation of (2R,3S,4R)-6-nitro-4-[N-(4-trifluoromethoxyphenyl)-N-(2-methyl-2H-tetrazol-5-ylmethyl)amino]-3-hydroxy-2-methyl-2-dimethoxymethyl-3,4-dihydro-2H-1-benzopyran The same procedure as step 3 of example 1 was accomplished, except for using epoxide compound (504 mg, 1.79 mmol) obtained in the above step 1 of example 76 and N-(4-trifluoromethoxyphenyl)-N-(2-methyl-1H-tetrazol-5-ylmethyl)amine (490 mg, 1.79 mmol). The crude product was purified by silica gel column chromatography (developing solvent-n-hexane:ethyl acetate=2:1), to give desired compound (645 mg, yield: 65%).

$^1$H NMR (CDCl$_3$, 200 MHz): δ 1.63 (s, 3H), 3.50 (s, 3H), 3.55 (s, 3H,) 3.92 (q, 1H), 4.30 (brs, 1H), 4.35 (s, 3H), 4.73 (s, 1H), 4.85 (d, 1H), 5.47 (s, 1H), 5.62 (d, 2H), 6.86 (d, 2H), 6.96 (d, 1H), 7.07 (d, 2H), 7.99 (s, 1H), 8.09 (dd, 1H)

EXAMPLE 85

Preparation of (2R,3S,4R)-6-amino-4-[N-(4-trifluoromethoxyphenyl)-N-(2-methyl-2H-tetrazol-5ylmethyl)amino]-3-hydroxy-2-methyl-2-dimethoxymethyl-3,4-dihydro-2H-1-benzopyran The same procedure as example 10 was accomplished, except for using the compound (295 mg, 0.53 mmol) obtained in example 84. The crude product was purified by silica gel column chromatography (developing solvent-n-hexane:ethyl acetate=1:3), to give desired compound (225 mg, yield: 81%).

$^1$H NMR (CDCl$_3$, 200 MHz): δ 1.54 (s, 3H), 3.48 (s, 3H), 3.52 (s, 3H), 3.95 (q, 1H), 4.32 (s, 1H), 4.41 (d, 1H), 4.66-4.74 (m, 3H), 5.36 (d, 1H), 6.46 (s, 1H), 6.54 (dd, 1H), 6.70 (d, 1H), 6.86 (d, 2H), 7.03 (d, 2H).

EXAMPLE 86

Preparation of (2S,3S,4R)-6-nitro-4-[N-(4-chlorophenyl)-N-(2-methyl-2H-tetrazol-5-ylmethyl)amino]-3-acetoxy-2-methyl-2-dimethoxymethyl-3,4-dihydro-2H-1-benzopyran The compound (700 mg, 1.43 mmol) obtained in the above example 21 was dissolved in dichloromethane (5 ml), thereto triethylamine (0.3 ml) and acetic anhydride (160 μl) were added. 4-Dimethylaminopyridine (50 mg) was added to the reaction mixture. The reaction mixture was stirred at the room temperature for 5 hours. Water (30 ml) was added to the reaction mixture. The reaction mixture was extracted with ethyl acetate (30 ml), and the organic layer was washed with saturated brine solution (20 ml), dried over anhydrous magnesium sulfate, and concentrated. The crude product was purified by silica gel column chromatography (developing solvent-n-hexane:ethyl acetate=1:1), to give desired compound (652 mg, 83%).

$^1$H NMR (CDCl$_3$, 200 MHz): δ 1.41 (s, 3H), 1.65 (d, 3H), 3.52 (s, 3H), 3.57 (s, 3H), 4.25 (s, 5H), 4.76 (d, 1H), 5.24 (d, 1H), 5.71 (d, 1H), 6.90 (d, 2H), 7.00 (d, 1H), 7.15 (d, 2H), 8.08 (dd, 1H), 8.71 (d, 1H).

EXAMPLE 87

Preparation of (2S,3S,4R)-6-acetamino-4-[N-(4-chlorophenyl)-N-(2-methyl-2H-tetrazol-5-ylmethyl)amino]-3-acetoxy-2-methyl-2-dimethoxymethyl-3,4-dihydro-2H-1-benzopyran The compound (150 mg, 0.32 mmol) obtained in the above example 10 was dissolved in dichloromethane (3 ml), thereto triethylamine (0.11 ml) and acetic anhydride (65 μl) were added. 4-dimethylaminopyridine (11 mg) was added to the reaction mixture. The reaction mixture was stirred at the room temperature for 12 hours. Water (20 ml) was added to the reaction mixture. The reaction mixture was extracted with ethyl acetate (20 ml), and the organic layer was washed with saturated brine solution (20 ml), dried over anhydrous magnesium sulfate, and concentrated. The crude product was purified by silica gel column chromatography (developing solvent-n-hexane:ethyl acetate=1:4), to give desired compound (158 mg, 88%).

$^1$H NMR (CDCl$_3$, 200 MHz): δ 1.32 (s, 3H), 1.65 (s, 3H), δ 2.08 (s, 3H), 3.47 (s, 3H), 3.56 (s, 3H), 4.33-4.21 (brs, 5H), 4.68 (d, 1H), 5.13 (d, 1H), 5.62 (d, 1H), 6.86 (d, 3H), 7.11 (d, 2H), 7.39 (brs, 1H), 7.49 (s, 1H), 7.63 (d, 1H).

EXAMPLE 88

Preparation of (2S,3S,4R)-6-acetamino-4-[N-(4-chlorophenyl)-N-(2-methyl-2H-tetrazol-5-ylmethyl)amino]-3-hydroxy-2-methyl-2-dimethoxymethyl-3,4-dihydro-2H-1-benzopyran The same procedure as example 86 was accomplished, except for using the compound (359 mg, 0.76 mmol) obtained in example 10. The crude product was purified by silica gel column chromatography (developing solvent-n-hexane:ethyl acetate=1:4), to give desired compound (376 mg, yield: 96%).

$^1$H NMR (CDCl$_3$, 200 MHz): δ 1.41 (s, 3H), 2.07 (s, 3H), 3.56 (s, 3H), 3.61 (s, 3H), 4.31 (brs, 4H), 4.57 (s, 1H), 4.72 (d, 1H), 4.94 (brs, 1H), 5.06 (d, 1H), 6.83 (brs, 1H), 6.90 (d, 2H), 7.10 (d, 3H), 7.20 (brs, 1H), 7.38 (dd, 1H).

EXAMPLE 89

Preparation of (2S,3S,4R)-6-amino-4-[N-(4-chlorophenyl)-N-(2-methyl-2H-tetrazol-5-ylmethyl)amino]-3-acetoxy-2-methyl-2-dimethoxymethyl-3,4-dihydro-2H-1-benzopyran The same procedure as example 10 was accomplished, except for using the compound (150 mg, 0.28 mmol) obtained in example 86. The crude product was purified by silica gel column chromatography (developing solvent-n-hexane:ethyl acetate=1:3), to give desired compound (102 mg, yield: 77%).

$^1$H NMR (CDCl$_3$, 200 MHz): δ 1.30 (s, 3H), 1.62 (s, 3H), 3.45 (s, 3H), 3.56 (s, 3H), 4.18 (s, 1H), 4.23 (s, 1H), 4.31 (d, 1H), 4.68 (d, 1H), 5.12 (d, 1H), 5.58 (d, 1H), 6.57 (dd, 1H), 6.72 (d, 1H), 6.87 (d, 2H), 7.03 (d, 1H), 7.11 (d, 2H).

EXAMPLE 90

Preparation of (2S,3R,4S)-6-bromo-4-[N-(4-chlorophenyl)-N-(2-methyl-2H-tetrazol-5-ylmethyl)amino]-3-hydroxy-2-methyl-2-dimethoxymethyl-3,4-dihydro-2H-1-benzopyran The same procedure as step 3 of example 1 was accomplished, except for using (2S,3R,4R)-6-bromo-2-methyl-2-dimethoxymethyl-3,4-epoxy-3,4-dihydro-2H-1-benzopyran (192 mg, 0.61 mmol) and N-(4-chlorophenyl)-N-(2-methyl-2H-tetrazol-5-ylmethyl)amine (136 mg, 0.60 mmol). The crude product was purified by silica gel column chromatography (developing solvent-n-hexane:ethyl acetate=1:2), to give desired compound (55 mg, yield: 17%).

$^1$H NMR (CDCl$_3$, 200 MHz): δ 1.26-1.31 (m, 3H), 1.57 (s, 3H), 3.48 (s, 3H), 3.52 (s, 3H), 3.96-3.91 (m, 1H), 4.32 (s, 3H), 4.68 (d, 1H), 4.78 (d, 1H), 5.05 (brs, 1H), 5.49 (d, 1H), 6.88-6.74 (m, 3H), 7.27-7.12 (m, 5H).

EXAMPLE 91

Preparation of (2R,3R,4S)-6-bromo-4-[N-(4-chlorophenyl)-N-(2-methyl-2H-tetrazol-5-ylmethyl)amino]-3-hydroxy-2-methyl-2-dimethoxymethyl-3,4-dihydro-2H-1-benzopyran The same procedure as step 3 of example 1 was accomplished, except for using (2R,3R,4R)-6-bromo-2-methyl-2-dimethoxymethyl-3,4-epoxy-3,4-dihydro-2H-1-benzopyran (232 mg, 0.74 mmol) and N-(4-chlorophenyl)-N-(2-methyl-2H-tetrazol-5-ylmethyl)amine (164 mg, 0.74 mmol). The crude product was purified by silica gel column chromatography (developing solvent-n-hexane:ethyl acetate=3:1), to give desired compound (165 mg, yield: 41%).

$^1$H NMR (CDCl$_3$, 200 MHz): δ 1.28-1.25 (m, 3H), 1.42 (s, 3H), 3.55 (s, 3H), 3.61 (s, 3H), 4.33-4.30 (brs, 5H), 4.58 (s, 1H), 4.75 (d, 1H), 5.14-5.05 (brs, 1H), 6.87-6.82 (m, 3H), 7.12 (d, 2H), 7.28-7.23 (m, 2H).

EXAMPLE 92

Preparation of (2S,3R,4S)-6-bromo-4-[N-(4-fluorophenyl)-N-(2-methyl-2H-tetrazol-5-ylmethyl)amino]-3-hydroxy-2-methyl-2-dimethoxymethyl-3,4-dihydro-2H-1-benzopyran The same procedure as step 3 of example 1 was accomplished, except for using (2S,3R,4R)-6-bromo-2-methyl-2-dimethoxymethyl-3,4-epoxy-3,4-dihydro-2H-1-benzopyran (209 mg, 0.66 mmol) and N-(4-fluorophenyl)-N-(2-methyl-2H-tetrazol-5-ylmethyl)amine (138 mg, 0.66 mmol). The crude product was purified by silica gel column chromatography (developing solvent-n-hexane:ethyl acetate=6:1), to give desired compound (165 mg, yield: 51%).
$^1$H NMR (CDCl$_3$, 200 MHz): δ 1.28-1.21 (m, 3H), 1.56 (s, 3H), 3.47 (d, 3H), 3.51 (s, 3H), 4.92 (d, 1H), 4.30 (d, 3H), 4.40 (s, 1H), 4.66 (d, 1H), 4.76 (d,1H), 5.00 (brs, 1H), 5.41 (d, 1H), 6.94-6.72 (m, 5H), 7.21-7.26 (m, 2H).

EXAMPLE 93

Preparation of (2R,3R,4S)-6-bromo-4-[N-(4-fluorophenyl)-N-(2-methyl-2H-tetrazol-5-ylmethyl)amino]-3-hydroxy-2-methyl-2-dimethoxymethyl-3,4-dihydro-2H-1-benzopyran The same procedure as step 3 of example 1 was accomplished, except for using (2R,3R,4R)-6-bromo-2-methyl-2-dimethoxymethyl-3,4-epoxy-3,4-dihydro-2H-1-benzopyran (198 mg, 0.63 mmol) and N-(4-fluorophenyl)-N-(2-methyl-2H-tetrazol-5-ylmethyl)amine (130 mg, 0.63 mmol). The crude product was purified by silica gel column chromatography (developing solvent-n-hexane:ethyl acetate=4:1), to give desired compound (175 mg, yield: 53%).
$^1$H NMR (CDCl$_3$, 200 MHz): δ 1.20-1.27 (m, 3H), 1.40 (s, 3H), 2.03 (d, 3H), 3.55 (s, 3H), 3.60 (s, 3H), 4.28-4.33 (m, 5H), 4.56 (s, 1H), 4.73 (d, 1H), 5.02 (d, 1H), 6.80-6.88 (m, 5H), 7.22-7.26 (m, 2H).

EXAMPLE 94

Preparation of (2R,3R,4S)-6-bromo-4-[N-(2-methyl-2H-tetrazol-5-ylmethyl)phenylamino]-3-hydroxy-2-methyl-2-dimethoxymethyl-3,4-dihydro-2H-1-benzopyran The same procedure as step 3 of example 1 was accomplished, except for using (2R,3R,4R)-6-bromo-2-methyl-2-dimethoxymethyl-3,4-epoxy-3,4-dihydro-2H-1-benzopyran (204 mg, 0.65 mmol) and N-(2-methyl-2H-tetazole-5-ylmethyl)phenylamine (123 mg, 0.65 mmol). The crude product was purified by silica gel column chromatography (developing solvent-n-hexane:ethyl acetate=3:1), to give desired compound (196 mg, yield: 60%).
$^1$H NMR (CDCl$_3$, 200 MHz): δ 1.27-1.39 (m, 3H), 1.60 (s, 3H), 3.50 (d, 3H), 3.53 (s, 3H), 3.91 (d, 1H), 4.30-4.50 (brs, 3H), 4.77 (d, 1H), 4.80 (d, 1H), 5.02 (brs, 1H), 5.40 (d, 1H), 6.62-6.89 (m, 5H), 7.10-7.40 (m, 5H).

EXAMPLE 95

Preparation of (2R,3S,4R)-6-methanesulfonyloxy-4-[N-(4-chlorophenyl)-N-(2-methyl-2H-tetrazol-5-ylmethyl)amino]-3-hydroxy-2-methyl-2-dimethoxymethyl-3,4-dihydro-2H-1-benzopyran The same procedure as step 3 of example 1 was accomplished, except for using (2R,3S,4S)-6-methane sulfonyloxy-2-methyl-2-dimethoxymethyl-3,4-epoxy-3,4-dihydro-2H-1-benzopyran (231 mg, 0.70 mmol) and N-(4-chlorophenyl)-N-(2-methyl-2H-tetrazol-5-ylmethyl)amine (187 mg, 0. 84 mmol). The crude product was purified by silica gel column chromatography (developing solvent-n-hexane:ethyl acetate=1:1), to give desired compound (104 mg, yield: 27%).
$^1$H NMR (CDCl$_3$, 200 MHz): δ 1.58 (s, 3H), 3.06 (s, 3H), 3.52 (d, 6H), 4.07 (m, 2H), 4.32 (s, 3H), 4.67 (s, 1H), 5.10 (s, 1H), 5.50 (d, 1H), 6.78-7.15 (m, 7H).

EXAMPLE 96

Preparation of (2S,3S,4R)-6-methane sulfonyloxy-4-[N-(4-chlorophenyl)-N-(2-methyl-2H-tetrazol-5-ylmethyl)amino]-3-hydroxy-2-methyl-2-dimethoxymethyl-3,4-dihydro-2H-1-benzopyran The same procedure as example 95 was accomplished. The crude product was purified by silica gel column chromatography (developing solvent-n-hexane:ethyl acetate=1:1), to give desired compound (64 mg, yield: 17%).
$^1$H NMR (CDCl$_3$, 200 MHz): δ 1.44 (s, 3H), 3.04 (s, 3H), 3.59 (d, 6H), 4.32 (s, 3H), 4.57 (s, 1H), 4.78 (d, 1H), 5.10 (d, 1H), 6.94-7.14 (m, 7H).

EXAMPLE 97

Preparation of (2S,3S,4R)-6-hydroxy-4-[N-(4-chlorophenyl)-N-(2-methyl-2H-tetrazol-5-ylmethyl)amino]-3-hydroxy-2-methyl-2-dimethoxymethyl-3,4-dihydro-2H-1-benzopyran The compound (50 mg, 0.09 mmol) obtained in the example 96 was dissolved in ethyl alcohol (2 ml), thereto 6 N KOH (1 ml) was added. The reaction mixture was heated at reflux for 1 hour, thereto 1N HCl (10 ml) was added. The reaction mixture was extracted with ethyl acetate (20 ml). The organic layer was dried over anhydrous magnesium sulfate and concentrated to obtain a crude product. The crude product was purified by silica gel column chromatography (developing solvent-n-hexane:ethyl acetate=1:1), to give desired compound (40 mg, yield: 93%).
$^1$H NMR (CDCl$_3$, 200 MHz): δ 1.38 (s, 3H), 3.56 (d, 3H), 4.28 (s, 3H), 4.55 (s, 1H), 4.90 (s, 1H), 5.10 (d, 1H), 6.75-7.10 (m, 7H).

EXAMPLE 98

Preparation of (2S,3S,4R)-6-nitro-5-methyl-4-[N-(4-chlorophenyl)-N-(2-methyl-2H-tetrazol-5-ylmethyl)amino]-3-hydroxy-2-methyl-2-dimethoxymethyl-3,4-dihydro-2H-1-benzopyran The same procedure as step 3 of example 1 was accomplished, except for using (2S,3S,4S)-6-nitro-5-methyl-2-methyl-2-dimethoxymethyl-3,4-epoxy-3,4-dihydro-2H-1-benzopyran (100 ml, 0.34 mmol). The crude product was purified by silica gel column chromatography (developing solvent-n-hexane:ethyl acetate=1:1), to give desired compound (80 mg, yield: 45%).
$^1$H NMR (CDCl$_3$, 200 MHz): δ 1.30 (s, 3H), 2.12 (s, 3H), 3.60 (d, 6H), 4.10 (s, 3H), 4.23 (s, 3H), 4.30 (s, 2H), 4.62 (d, 1H), 5.08 (d, 1H), 6.80-7.80 (m, 6H).

EXAMPLE 99

Preparation of (2S,3S,4R)-6-nitro-4-[N-(4-fluorophenyl)-N-(2-methyl-2H-tetrazol-5-ylmethyl)amino]-3-hydroxy-2-methyl-2-methoxymethyl-3,4-dihydro-2H-1-benzopyran The same procedure as step 3 of example 1 was accomplished, except for using (2S,3S,4S)-6-nitro-2-methyl-2-methoxymethyl-3,4-epoxy-3,4-dihydro-2H-1-benzopyran (100 mg, 0.40 mmol) and amine compound (116 mg, 0.52 mmol) obtained in step 2 of example 1. The crude product was purified by silica gel column chromatography (developing solvent-n-hexane:ethyl acetate=1:1), to give desired compound (110 mg, yield: 58%).

$^1$H NMR (CDCl$_3$, 200 MHz): δ 1.40 (s, 3H), 3.43 (s, 3H), 3.70 (dd, 2H), 4.28 (s, 2H), 4.90 (d, 1H), 5.12 (d, 1H), 6.80-7.20 (m, 5H), 8.05 (m, 2H).

EXAMPLE 100

Preparation of (3R,4S)-6-cyano-4-[N-(4-chlorophenyl)-N-(2-methyl-2H-tetrazol-5-ylmethyl)amino]-3-hydroxy-2,2-dimethyl-3,4-dihydro-2H-1-benzopyran The same procedure as step 3 of example 1 was accomplished, except for using (3R,4R)-6-cyano-2,2-dimethyl-3,4-epoxy-3,4-dihydro-2H-1-benzopyran (300 mg, 1.49 mmol) and amine compound (270 mg, 1.19 mmol) obtained in step 2 of example 1. The crude product was purified by silica gel column chromatography (developing solvent-n-hexane:ethyl acetate=2:1), to give desired compound (109 mg, yield: 22%).

$^1$H NMR (CDCl$_3$, 200 MHz): δ 1.42 (s, 3H), 1.58 (s, 3H), 3.85 (d, 1H), 4.13 (s, 3H), 4.22 (dd, 1H), 4.77 (d, 1H), 5.10 (d, 1H), 5.20 (d, 1H), 6.81-6.93 (m, 3H), 7.15 (d, 1H), 7.36 (s, 1H), 7.46 (dd, 1H).

EXAMPLE 101

Preparation of (3R,4S)-6-cyano-4-[N-(2-methyl-2H-tetrazol-5-ylmethyl)phenylamino]-3-hydroxy-2,2-dimethyl-3,4-dihydro-2H-1-benzopyran The same procedure as step 3 of example 1 was accomplished, except for using (3R,4R)-6-cyano-2,2-dimethyl-3,4-epoxy-3,4-dihydro-2H-1-benzopyran (200 mg, 0.99 mmol) and N-(2-methyl-2H-tetrazol-5-ylmethyl)phenylamine (188 mg, 0.99 mmol). The crude product was purified, to give desired compound (299 mg, yield: 77%).

$^1$H NMR (CDCl$_3$, 200 MHz): δ 1.43 (s, 3H), 1.59 (s, 3H), 3.88 (d, 1H), 4.32 (dd, 1H), 4.33 (s, 3H), 4.80 (d, 1H), 5.19 (d, 1H), 5.39 (d, 1H), 6.92-6.70 (m, 4H), 7.20 (d, 2H), 7.40 (s, 1H), 7.45 (dd, 1H).

EXAMPLE 102

Preparation of (2S,3S,4R)-6-hydroxy-4-[N-(4-chlorophenyl)-N-(2-methyl-2H-tetrazol-5-ylmethyl)amino]-3-hydroxy-2-methyl-2-dimethoxymethyl-3,4-dihydro-2H-1-benzopyran The compound (64 mg, 0.1 mmol) obtained in the example 96 was dissolved in ethyl alcohol (2 ml), thereto 6 N KOH (1 ml) was added. The reaction mixture was stirred at the room temperature for 1 hour. The reaction mixture was neutralized with 1N HCl, and was extracted with ethyl acetate (20 ml). The organic layer was dried over anhydrous magnesium sulfate, and concentrated. The crude product was purified by silica gel column chromatography (developing solvent-n-hexane:ethyl acetate=1:2), to give desired compound (45 mg, yield: 82%).

$^1$H NMR (CDCl$_3$, 200 MHz): δ 1.38 (s, 3H), 3.53 (s, 3H), 3.56 (s, 3H), 4.28 (s, 3H), 4.55 (s, 1H), 4.90 (s, 1H), 5.10 (d, 1H), 6.75-7.10 (m, 7H).

EXAMPLE 103

Preparation of (2S,3S,4R)-8-nitro-4-[N-(4-chlorophenyl)-N-(2-methyl-2H-tetrazol-5-ylmethyl)amino]-3-hydroxy-2-methyl-2-dimethoxymethyl-3,4-dihydro-2H-1-benzopyran The same procedure as step 3 of example 1 was accomplished, except for using (2S,3S,4S)-8-nitro-2-methyl-2-dimethoxymethyl-3,4-epoxy-3,4-dihydro-2H-1-benzopyran (751 mg, 2.67 mmol) and N-(4-chlorophenyl)-N-(2-methyl-2H-tetrazol-5-ylmethyl)amine (597 mg, 2.67 mmol). The crude product was purified by silica gel column chromatography (developing solvent-n-hexane:ethyl acetate=2:1), to give desired compound (691 mg, yield: 51%).

$^1$H NMR (CDCl$_3$, 200 MHz): δ 1.41 (s, 3H), 3.49 (s, 3H), 3.53 (s, 3H), 4.24 (s, 3H), 4.46-4.72 (m, 4H), 5.06 (d, 1H), 6.79 (d, 1H), 6.91 (t, 1H), 7.04 (d, 2H), 7.45 (d, 1H), 7.67 (d, 1H).

EXAMPLE 104

Preparation of (2S,3S,4R)-8-amino-4-[N-(4-chlorophenyl)-N-(2-methyl-2H-tetrazol-5-ylmethyl)amino]-3-hydroxy-2-methyl-2-dimethoxymethyl-3,4-dihydro-2H-1-benzopyran The same procedure as example 10 was accomplished, except for using the compound (170 mg, 0.34 mmol) obtained in example 103. The crude product was purified by silica gel column chromatography (developing solvent-n-hexane:ethyl acetate=1:2), to give desired compound (128 mg, yield: 80%).

$^1$H NMR (CDCl$_3$, 200 MHz): δ 1.43 (s, 3H), 3.55 (s, 3H), 3.60 (s, 3H), 4.29 (s, 3H), 4.35 (d, 1H), 4.62 (s, 2H), 4.89 (brs, 1H), 5.12 (d, 1H), 6.45 (d, 1H), 6.60-6.72 (m, 2H), 6.82 (d, 2H), 7.10 (d, 2H)

EXAMPLE 105

Preparation of (2R,3S,4R)-8-nitro-4-[N-(4-chlorophenyl)-N-(2-methyl-2H-tetrazol-5-ylmethyl)amino]-3-hydroxy-2-methyl-2-dimethoxymethyl-3,4-dihydro-2H-1-benzopyran The same procedure as step 3 of example 1 was accomplished, except for using (2R,3S,4S)-8-nitro-2-methyl-2-dimethoxymethyl-3,4-epoxy-3,4-dihydro-2H-1-benzopyran (751 mg, 2.67 mmol) and N-(4-chlorophenyl)-N-(2-methyl-2H-tetrazol-5-ylmethyl)amine (597 mg, 2.67 mmol). The crude product was purified by silica gel column chromatography (developing solvent-n-hexane:ethyl acetate=2:1), to give desired compound (200 mg, yield: 15%).

$^1$H NMR (CDCl$_3$, 200 MHz): δ 1.63 (s, 3H), 3.46 (s, 6H), 4.00 (d, 1H), 4.31 (s, 3H), 4.76 (s, 2H), 5.30 (brs, 1H), 5.59 (d, 1H), 6.78-6.94 (m, 3H), 7.13 (d, 2H), 7.23 (d, 1H), 7.66 (d, 1H).

EXAMPLE 106

Preparation of (2R,3S,4R)-8-amino-4-[N-(4-chlorophenyl)-N-(2-methyl-2H-tetrazol-5-ylmethyl)amino]-3-hydroxy-2-methyl-2-dimethoxymethyl-3,4-dihydro-2H-1-benzopyran The same procedure as example 10 was accomplished, except for using the compound (100 mg, 0.20 mmol) obtained in example 105. The crude product was purified by silica gel column chromatography (developing solvent-n-hexane:ethyl acetate=1:1), to give desired compound (70 mg, yield: 74%).

$^1$H NMR (CDCl$_3$, 200 MHz): δ 1.60 (s, 3H), 3.48 (s, 3H), 3.53 (s, 3H), 4.00 (d, 1H), 4.30 (s, 3H), 4.42 (brs, 1H), 4.63 (s, 2H), 5.40 (d, 1H), 6.45 (d, 1H), 6.61-6.70 (m, 2H), 6.83 (d, 2H), 7.11 (d, 2H).

EXAMPLE 107

Preparation of (2R,3R,4S)-6-nitro-4-[N-(4-chlorophenyl)-N-(2-methyl-2H-tetrazol-5-ylmethyl)amino]-3-hydroxy-2-methyl-2-dimethoxymethyl-3,4-dihydro-2H-1-benzopyran The same procedure as step 3 of example 1 was accomplished, except for using the epoxide compound (250 mg, 0.9 mmol) obtained in step 1 of example 2. The crude product was purified by silica gel column chromatography (developing solvent-n-hexane:ethyl acetate=2:1), to give desired compound (340 mg, yield: 82%).

$^1$H NMR (CDCl$_3$, 200 MHz): δ 1.67 (s, 3H), 3.49 (s, 3H), 3.59 (s, 3H,) 3.95 (dd, 1H), 4.32 (d, 1H), 4.48 (s, 3H), 4.83 (d, 1H), 4.72 (s, 1H), 5.60 (d, 1H), 6.82 (d, 2H), 6.95 (d, 1H), 7.16 (d, 2H), 7.99 (d, 1H), 8.06 (dd, 1H).

EXAMPLE 108

Preparation of (2R,3R,4S)-6-amino-4-[N-(4-chlorophenyl)-N-(2-methyl-2H-tetrazol-5-ylmethyl)amino]-3-hydroxy-2-methyl-2-dimethoxymethyl-3,4-dihydro-2H-1-benzopyran (2R,3R,4S)-6-nitro-4-[N-(4-chlorophenyl)-N-(2-methyl-2H-tetrazol-5-ylmethyl)amino]-3-hydroxy-2-methyl-2-dimethoxymethyl-3,4-dihydro-2H-1-benzopyran (100 mg, 0.2 mmol) prepared in example 107 was dissolved in methanol (2 ml), thereto Cu(OAc)$_2$ aqueous solution (0.38 ml, 0.4 M aqueous solution, 0.15 mmol) was added. Sodium borohydride (NaBH$_4$, 113 mg, 3.0 mmol) was slowly added to the solution at the room temperature for 30 min. The reaction mixture was stirred for 1 hour, thereto ethyl acetate (5 ml) was added. The reaction mixture was filtered to remove the black precipitation. NaHCO$_3$ aqueous solution (5 ml) was added to the resultant filtrate. The filtrate was extracted with ethyl acetate (30 ml). The organic layer was washed with saturated brine solution, dried over magnesium sulfate and concentrated. The crude product was purified by silica gel column chromatography (developing solvent-n-hexane:ethyl acetate=1:3), to give desired compound (60 mg, yield: 63%).

$^1$H NMR (CDCl$_3$, 200 MHz): δ 1.34 (s, 3H), 3.51 (s, 3H), 3.61 (s, 3H,) 4.02 (s, 3H), 4.10 (dd, 1H), 4.33 (d, 1H), 4.47 (s, 1H), 4.68 (d, 1H), 4.80-4.97 (m, 2H), 6.35 (d, 1H), 6.54 (dd, 1H), 6.74 (d, 2H), 6.81 (d, 2H), 7.14 (d, 2H).

EXAMPLE 109

Preparation of (2R,3S,4R)-6-nitro-4-[N-(4-chlorophenyl)-N-(2-methyl-2H-tetrazol-5-ylmethyl)amino]-3-hydroxy-2-methyl-2-dimethoxymethyl-3,4-dihydro-2H-1-benzopyran The epoxide compound (450 mg, 1.6 mmol) prepared in the step 1 of example 1 was dissolved in acetonitrile (0.5 ml). To the solution was added the secondary amine (363 mg, 1.6 mmol) containing tetrazole group, prepared in the step 2 of example 1 with magnesium perchloate ((MgClO$_4$)$_2$), 357 mg, 1.6 mmol). The reaction mixture was stirred for 10 hours, thereto NaHCO$_3$ aqueous solution (20 ml) was added. The reaction mixture was extracted with ethyl acetate (30 ml). The organic layer was washed with saturated brine solution, dried over magnesium sulfate and concentrated. The crude product was purified by silica gel column chromatography (developing solvent-n-hexane:ethyl acetate=2:1), to give desired compound (480 mg, yield: 60%).

$^1$H NMR (CDCl$_3$, 200 MHz): δ 1.48 (s, 3H), 3.58 (s, 3H), 4.29 (s, 3H,) 4.42 (dd, 1H), 4.61 (s, 1H), 4.82 (d, 1H), 5.13 (d, 1H), 5.18 (d, 1H), 6.84 (d, 1H), 7.05 (d, 1H), 7.15 (d, 2H), 8.08 (dd, 1H), 8.10 (d, 1H).

EXAMPLE 110

Preparation of (2R,3S,4R)-6-amino-4-[N-(4-chlorophenyl)-N-(2-methyl-2H-tetrazol-5-ylmethyl)amino]-3-hydroxy-2-methyl-2-dimethoxymethyl-3,4-dihydro-2H-1-benzopyran (2R,3S,4R)-6-nitro-4-[N-(4-chlorophenyl)-N-(2-methyl-2H-tetrazol-5-ylmethyl)amino]-3-hydroxy-2-methyl-2-dimethoxymethyl-3,4-dihydro-2H-1-benzopyran (100 mg, 0.2 mmol) prepared in example 109 was dissolved in methanol (2 ml), thereto Cu(OAc)$_2$ aqueous solution (0.38 ml, 0.4 M aqueous solution, 0.15 mmol) was added. To the solution sodium borohydride (NaBH$_4$, 113 mg, 3.0 mmol) was slowly added at the room temperature for 30 min. The reaction mixture was stirred for 1 hour, thereto ethyl acetate (5 ml) was added. The reaction mixture was filtered to remove the black precipitation. NaHCO$_3$ aqueous solution (5 ml) was added to the resulting filtrate. The filtrate was extracted with ethyl acetate (30 ml). The organic layer was washed with saturated brine solution, dried over magnesium sulfate and concentrated. The crude product was purified by silica gel column chromatography (developing solvent-n-hexane:ethyl acetate=1:3), to give desired compound (58 mg, yield: 62%).

$^1$H NMR (CDCl$_3$, 200 MHz): δ 1.54 (s, 3H), 3.49 (s, 3H), 3.52 (s, 3H,) 4.30 (d, 1H), 4.32 (s, 3H), 4.41-4.70 (m, 3H), 5.33 (d, 1H), 6.45 (s, 1H), 6.55 (dd, 1H), 6.68 (d, 1H), 6.82 (d, 2H), 7.13 (d, 2H).

EXAMPLE 111

Preparation of (2S,3R,4R)-6-nitro-4-[N-(4-chlorophenyl)-N-(2-methyl-2H-tetrazol-5-ylmethyl)amino]-3-hydroxy-2-methyl-2-dimethoxymethyl-3,4-dihydro-2H-1-benzopyran (2S,3S,4R)-6-nitro-4-[N-(4-chlorophenyl)-N-(2-methyl-2H-tetrazol-5-ylmethyl)amino]-3-hydroxy-2-methyl-2-dimethoxymethyl-3,4-dihydro-2H-1-benzopyran (100 mg, 0.20 mmol) was dissolved in the mixed solvent (3.8 ml, toluene/tetrahydrofuran=1/1). Triphenyl phosphine (268 mg, 0.99 mmol) and 4-nitrobenzoic acid (149 mg, 0.87 mmol) were added to the solution at 0° C. Thereafter, diethyl azocarboxylte (156 μl, 0.99 mmol) was slowly added to the reaction through syringe. The reaction mixture was stirred for 3 days at the room temperature. The solvent was removed under reduced pressure to obtain a crude product. The crude product was purified by short silica gel column chromatoghaphy to semi-product. Further purification was not accomplished. The crude product was dissolved in dichloromethane. DIBAL-H (1 M in hexane, 1.36 mmol) was slowly added to the solution dropwise at −20° C. The reaction mixture was stirred for 20 min. To terminate the reaction, the saturated brine solution was added to the reaction mixture. The organic layer was separated. The solvent was removed under reduced pressure to obtain a crude product. The crude product was purified by silica gel column chromatography (developing solvent-n-hexane:ethyl acetate=1:2), to give desired compound (18 mg, yield: 19%).

$^1$H NMR (CDCl$_3$, 200 MHz): δ 1.52 (s, 3H), 3.63 (s, 3H), 3.69 (s, 3H,) 4.32 (s, 3H), 4.48 (d, 1H), 4.53 (m, 2H), 4.74 (s, 1H), 5.32 (d, 1H), 5.45 (d, 1H), 6.85 (d, 2H), 7.03 (d, 1H), 7.16 (d, 2H), 8.11 (dd, 1H).

EXAMPLE 112

Preparation of (2S,3R,4R)-6-amino-4-[N-(4-chlorophenyl)-N-(2-methyl-2H-tetrazol-5-ylmethyl)amino]-3-hydroxy-2-methyl-2-dimethoxymethyl-3,4-dihydro-2H-1-benzopyran The same procedure as example 110 was accomplished, except for using (2S,3R,4R)-6-nitro-4-[N-(4-chlorophenyl)-N-(2-methyl-2H-tetrazol-5-ylmethyl)amino]-3-hydroxy-2-methyl-2-dimethoxymethyl-3,4-dihydro-2H-1-benzopyran (100 mg, 0.2 mmol) prepared in example 111. The desired compound (62 mg, yield: 67%) was obtained.

$^1$H NMR (CDCl$_3$, 200 MHz): δ 1.48 (s, 3H), 3.52 (s, 3H), 3.56 (s, 3H), 4.01 (s, 3H), 4.13 (m, 1H), 4.48 (d, 1H), 4.75 (m, 1H), 4.90 (m, 3H), 6.42 (d, 1H), 6.62 (dd, 1H), 6.82 (d, 2H), 6.94 (d, 2H), 7.18 (d, 2H).

EXAMPLE 113

Preparation of (2S,3S,4S)-6-nitro-4-[N-(4-chlorophenyl)-N-(2-methyl-2H-tetrazol-5-ylmethyl)amino]-3-hydroxy-2-methyl-2-dimethoxymethyl-3,4-dihydro-2H-1-benzopyran The same procedure as example 111 was accomplished, except for using (2S,3R,4S)-6-nitro-4-[N-(4-chlorophenyl)-N-(2-methyl-2H-tetrazol-5-ylmethyl)amino]-3-hydroxy-2-methyl-2-dimethoxymethyl-3,4-dihydro-2H-1-benzopyran (100 mg, 0.20 mmol) prepared in example 2. The desired compound (14 mg, yield: 14%) was obtained.

$^1$H NMR (CDCl$_3$, 200 MHz): δ 1.57 (s, 3H), 3.53 (s, 3H), 3.62 (s, 3H), 4.34 (s, 3H), 4.52 (d, 1H), 4.67 (m, 2H), 4.82 (m, 1H), 5.41 (d, 1H), 5.47 (d, 1H), 6.86 (d, 2H), 7.12 (d, 1H), 7.18 (d, 2H), 8.12 (d, 1H), 8.14 (dd, 1H).

EXAMPLE 114

Preparation of (2S,3S,4S)-6-amino-4-[N-(4-chlorophenyl)-N-(2-methyl-2H-tetrazol-5-ylmethyl)amino]-3-hydroxy-2-methyl-2-dimethoxymethyl-3,4-dihydro-2H-1-benzopyran The same procedure as example 110 was accomplished, except for using (2S,3S,4S)-6-nitro-4-[N-(4-chlorophenyl)-N-(2-methyl-2H-tetrazol-5-ylmethyl)amino]-3-hydroxy-2-methyl-2-dimethoxymethyl-3,4-dihydro-2H-1-benzopyran (100 mg, 0.20 mmol) prepared in example 113. The desired compound (55 mg, yield: 57%) was obtained.

$^1$H NMR (CDCl$_3$, 200 MHz): δ 1.48 (s, 3H), 3.53 (s, 3H), 3.58 (s, 3H), 4.02 (dd, 3H), 4.35 (m, 1H), 4.38 (d, 1H), 4.92 (m, 2H), 5.35 (m, 2H), 6.42 (d, 1H), 6.59 (d, 1H), 6.73 (d, 1H), 6.92 (d, 2H), 7.19 (d, 2H).

EXAMPLE 115

Preparation of (2R,3R,4R)-6-nitro-4-[N-(4-chlorophenyl)-N-(2-methyl-2H-tetrazol-5-ylmethyl)amino]-3-hydroxy-2-methyl-2-dimethoxymethyl-3,4-dihydro-2H-1-benzopyran The same procedure as example 111 was accomplished, except for using (2R,3S,4R)-6-nitro-4-[N-(4-chlorophenyl)-N-(2-methyl-2H-tetrazol-5-ylmethyl)amino]-3-hydroxy-2-methyl-2-dimethoxymethyl-3,4-dihydro-2H-1-benzopyran (100 mg, 0.20 mmol) prepared in example 2. The desired compound (11 mg, yield: 11%) was obtained.

$^1$H NMR (CDCl$_3$, 200 MHz): δ 1.57 (s, 3H), 3.53 (s, 3H), 3.62 (s, 3H), 4.34 (s, 3H), 4.52 (d, 1H), 4.67 (m, 2H), 4.82 (m, 1H), 5.41 (d, 1H), 5.47 (d, 1H), 6.86 (d, 2H), 7.12 (d, 1H), 7.18 (d, 2H), 8.12 (d, 1H), 8.14 (dd, 1H).

EXAMPLE 116

Preparation of (2R,3R,4R)-6-amino-4-[N-(4-chlorophenyl)-N-(2-methyl-2H-tetrazol-5-ylmethyl)amino]-3-hydroxy-2-methyl-2-dimethoxymethyl-3,4-dihydro-2H-1-benzopyran The same procedure as example 110 was accomplished, except for using (2R,3R,4R)-6-nitro-4-[N-(4-chlorophenyl)-N-(2-methyl-2H-tetrazol-5-ylmethyl)amino]-3-hydroxy-2-methyl-2-dimethoxymethyl-3,4-dihydro-2H-1-benzopyran (100 mg, 0.20 mmol) prepared in example 115. The desired compound (51 mg, yield: 55%) was obtained.

$^1$H NMR (CDCl$_3$, 200 MHz): δ 1.48 (s, 3H), 3.53 (s, 3H), 3.58 (s, 3H), 4.02 (dd, 3H), 4.35 (m, 1H), 4.38 (d, 1H), 4.92 (m, 2H), 5.35 (m, 2H), 6.42 (d, 1H), 6.59 (dd, 1H), 6.73 (d, 1H), 6.92 (d, 2H), 7.19 (d, 2H).

EXAMPLE 117

Preparation of (2R,3S,4S)-6-nitro-4-[N-(4-chlorophenyl)-N-(2-methyl-2H-tetrazol-5-ylmethyl)amino]-3-hydroxy-2-methyl-2-dimethoxymethyl-3,4-dihydro-2H-1-benzopyran The same procedure as example 111 was accomplished, except for using (2R,3R,4S)-6-nitro-4-[N-(4-chlorophenyl)-N-(2-methyl-2H-tetrazol-5-ylmethyl)amino]-3-hydroxy-2-methyl-2-dimethoxymethyl-3,4-dihydro-2H-1-benzopyran (100 mg, 0.20 mmol) prepared in example 107. The desired compound (13 mg, yield: 13%) was obtained.

$^1$H NMR (CDCl$_3$, 200 MHz): δ 1.52 (s, 3H), 3.63 (s, 3H), 3.69 (s, 3H), 4.32 (s, 3H), 4.48 (d, 1H), 4.53 (m, 2H), 4.74 (m, 1H), 5.32 (d, 1H), 5.45 (d, 1H), 6.85 (d, 2H), 7.03 (d, 1H), 7.16 (d, 2H), 8.09 (d, 1H), 8.11 (dd, 1H).

EXAMPLE 118

Preparation of (2R,3S,4S)-6-amino-4-[N-(4-chlorophenyl)-N-(2-methyl-2H-tetrazol-5-ylmethyl)amino]-3-hydroxy-2-methyl-2-dimethoxymethyl-3,4-dihydro-2H-1-benzopyran The same procedure as example 110 was accomplished, except for using (2R,3S,4S)-6-nitro-4-[N-(4-chlorophenyl)-N-(2-methyl-2H-tetrazol-5-ylmethyl)amino]-3hydroxy-2-methyl-2-dimethoxymethyl-3,4-dihydro-2H-1-benzopyran (100 mg, 0.20 mmol) prepared in example 117. The desired compound (55 mg, yield: 59%) was obtained.

$^1$H NMR (CDCl$_3$, 200 MHz): δ 1.48 (s, 3H), 3.52 (s, 3H), 3.56 (s, 3H), 4.01 (s, 3H), 4.13 (m, 1H),-4.48 (d, 1H), 4.75 (m,

1H), 4.90 (m, 3H), 6.42 (d, 1H), 6.62 (dd, 1H), 6.82 (d, 1H), 6.94 (d, 2H), 7.18 (d, 2H).

The compounds of the present invention, prepared in the above examples were shown in table 1.

TABLE 1a

| Example No | R₁ substituents | R₁ position | R₂ | R₃ | R₄ substituents | R₄ position | R₅ substituents | R₅ position | R₆ substituents | R₆ position | n | m | stereochemistry |
|---|---|---|---|---|---|---|---|---|---|---|---|---|---|
| 1 | NO₂ | 6 |  | OH | Cl | 4 | H | | CH₃ | 2 | 0 | 1 | 2S, 3S, 4R |
| 2 | NO₂ | 6 | | | Cl | 4 | | | | | 0 | | 2S, 3R, 4S |
| 3 | NO₂ | 6 | | | H | | | | | | 0 | | 2S, 3S, 4R |
| 4 | NO₂ | 6 | | | H | | | | | | 0 | | 2S, 3R, 4S |
| 5 | NO₂ | 6 | | | F | 4 | | | | | 0 | | 2S, 3S, 4R |
| 6 | NO₂ | 6 | | | F | 4 | | | | | 0 | | 2S, 3R, 4S |
| 7 | NO₂ | 6 | | | H | | | | | | 1 | | 2S, 3S, 4R |
| 8 | NO₂ | 6 | | | H | | | | | | 1 | | 2S, 3R, 4S |
| 9 | NO₂ | 6 | | | NO₂ | 4 | | | | | 0 | | 2S, 3S, 4R |
| 10 | NH₂ | 6 | | | Cl | 4 | | | | | 0 | | 2S, 3S, 4R |
| 11 | NH₂ | 6 | | | Cl | 4 | | | | | 0 | | 2S, 3R, 4S |
| 12 | NO₂ | 6 | | | Cl | 4 | | | | 1 | 0 | | 2S, 3S, 4R |
| 13 | NO₂ | 6 | | | H | | | | | | 0 | | 2S, 3S, 4R |
| 14 | NO₂ | 6 | | | F | 4 | | | | | 0 | | 2S, 3S, 4R |
| 15 | NO₂ | 6 | | | H | | | | | | 1 | | 2S, 3S, 4R |
| 16 | NO₂ | 6 | | | H | | | | | | 1 | | 2S, 3R, 4S |
| 17 | NH₂ | 6 | | | Cl | 4 | | | | | 0 | | 2S, 3S, 4R |
| 18 | NO₂ | 6 | | | Cl | 4 | | | H | | 0 | | 2S, 3S, 4R |
| 19 | NO₂ | 6 | | | H | | | | | | 0 | | 2S, 3S, 4R |
| 20 | NO₂ | 6 | | | H | | | | | | 1 | | 2S, 3S, 4R |
| 21 | NO₂ | 6 | | | Cl | 3 | | | CH₃ | 2 | 0 | | 2S, 3S, 4R |
| 22 | NH₂ | 6 | | | Cl | 3 | | | | | | | 2S, 3S, 4R |
| 23 | NO₂ | 6 | | | CH₃ | 4 | | | | | | | 2S, 3S, 4R |
| 24 | NH₂ | 6 | | | CH₃ | 4 | | | | | | | 2S, 3S, 4R |
| 25 | NO₂ | 6 | | | Cl | 3 | | | | | | | 2S, 3R, 4S |
| 26 | NH₂ | 6 | | | Cl | 3 | | | | | | | 2S, 3R, 4S |
| 27 | NO₂ | 6 | | | CH₃ | 4 | | | | | | | 2S, 3R, 4S |
| 28 | NH₂ | 6 | | | CH₃ | 4 | | | | | | | 2S, 3R, 4S |
| 29 | NO₂ | 6 | | | Cl | 2 | | | | | | | 2S, 3R, 4S |
| 30 | NH₂ | 6 | | | Cl | 2 | | | | | | | 2S, 3R, 4S |
| 31 | NO₂ | 6 | | | OCF₃ | 4 | | | | | | | 2S, 3R, 4S |
| 32 | NH₂ | 6 | | | OCF₃ | 4 | | | | | | | 2S, 3R, 4S |
| 33 | NO₂ | 6 | | | CF₃ | 4 | | | | | | | 2S, 3R, 4S |
| 34 | NH₂ | 6 | | | CF₃ | 4 | | | | | | | 2S, 3R, 4S |
| 35 | NO₂ | 6 | | | COCH₃ | 3 | | | | | | | 2S, 3R, 4S |
| 36 | NH₂ | 6 | | | CH(OH)CH₃ | 3 | | | | | | | 2S, 3R, 4S |
| 37 | NO₂ | 6 | | | F | 4 | CH₃ | 2 | | | | | 2S, 3R, 4S |
| 38 | NH₂ | 6 | | | F | 4 | CH₃ | 2 | | | | | 2S, 3R, 4S |
| 39 | NO₂ | 6 | | | OCH₃ | 4 | H | | | | | | 2S, 3R, 4S |
| 40 | NH₂ | 6 | | | OCH₃ | 4 | | | | | | | 2S, 3R, 4S |
| 41 | NO₂ | 6 | | | Cl | 4 | CH₃ | 2 | | | | | 2S, 3R, 4S |
| 42 | NH₂ | 6 | | | Cl | 4 | CH₃ | 2 | | | | | 2S, 3R, 4S |
| 43 | NO₂ | 6 | | | OCH₃ | 2 | CH₃ | 5 | | | | | 2S, 3R, 4S |
| 44 | NH₂ | 6 | | | OCH₃ | 2 | CH₃ | 5 | | | | | 2S, 3R, 4S |
| 45 | NO₂ | 6 | | | CH₃ | 2 | CH₃ | 4 | | | | | 2S, 3R, 4S |
| 46 | NH₂ | 6 | | | CH₃ | 2 | CH₃ | 4 | | | | | 2S, 3R, 4S |
| 47 | NO₂ | 6 | | | CH₃ | 2 | CH₃ | 6 | | | | | 2S, 3R, 4S |
| 48 | NH₂ | 6 | | | CH₃ | 2 | CH₃ | 6 | | | | | 2S, 3R, 4S |
| 49 | NO₂ | 6 | | | CH₃ | 2 | CH₃ | 3 | | | | | 2S, 3R, 4S |
| 50 | NH₂ | 6 | | | CH₃ | 2 | CH₃ | 3 | | | | | 2S, 3R, 4S |
| 51 | NO₂ | 6 | | | CH(CH₃)₂ | 2 | H | | | | | | 2S, 3R, 4S |
| 52 | NH₂ | 6 | | | CH(CH₃)₂ | 2 | H | | | | | | 2S, 3R, 4S |
| 53 | NO₂ | 6 | | | COOEt | 4 | H | | | | | | 2S, 3R, 4S |
| 54 | NH₂ | 6 | | | COOEt | 4 | H | | | | | | 2S, 3R, 4S |
| 55 | NH₂ | 6 | | | H | | H | | | | | | 2S, 3R, 4S |
| 56 | NH₂ | 6 | | | F | 4 | H | | | | | | 2S, 3R, 4S |
| 57 | NH₂ | 6 | | | H | | H | | | | 1 | | 2S, 3R, 4S |
| 58 | NO₂ | 6 | | | COOMe | 3 | H | | | | 0 | | 2S, 3R, 4S |
| 59 | NH₂ | 6 | | | COOMe | 3 | H | | | | | | 2S, 3R, 4S |
| 60 | NO₂ | 6 | | | OH | 2 | H | | | | | | 2S, 3R, 4S |
| 61 | NH₂ | 6 | | | OH | 2 | H | | | | | | 2S, 3R, 4S |
| 62 | NO₂ | 6 | | | COOMe | 4 | OMe | 2 | | | | | 2S, 3R, 4S |
| 63 | NH₂ | 6 | | | COOMe | 4 | OMe | 2 | | | | | 2S, 3R, 4S |
| 64 | NO₂ | 6 | | | OH | 4 | CH₃ | 2 | | | | | 2S, 3R, 4S |
| 65 | NH₂ | 6 | | | OH | 4 | CH₃ | 2 | | | | | 2S, 3R, 4S |
| 66 | NO₂ | 6 | | | Et | 2 | H | | | | | | 2S, 3R, 4S |

TABLE 1a-continued

| Example No | R₁ substituents | R₁ position | R₂ | R₃ | R₄ substituents | R₄ position | R₅ substituents | R₅ position | R₆ substituents | R₆ position | n | m | stereochemistry |
|---|---|---|---|---|---|---|---|---|---|---|---|---|---|
| 67 | NH₂ | 6 | | | Et | 2 | H | | | | | | 2S, 3R, 4S |
| 68 | NO₂ | 6 | | | COOMe | 5 | CH₃ | 2 | | | | | 2S, 3R, 4S |
| 69 | NH₂ | 6 | | | COOMe | 5 | CH₃ | 2 | | | | | 2S, 3R, 4S |
| 70 | NO₂ | 6 | | | OH | 2 | CH₃ | 5 | | | | | 2S, 3R, 4S |
| 71 | NH₂ | 6 | | | OH | 2 | CH₃ | 5 | | | | | 2S, 3R, 4S |
| 72 | NO₂ | 6 | | | CH₃ | 4 | CH₃ | 2.6 | | | | | 2S, 3R, 4S |
| 73 | NH₂ | 6 | | | CH₃ | 4 | CH₃ | 2.6 | | | | | 2S, 3R, 4S |
| 74 | NO₂ | 6 | | | CF₃ | 4 | H | | | | | | 2S, 3S, 4R |
| 75 | NH₂ | 6 | | | CF₃ | 4 | H | | | | | | 2S, 3S, 4R |
| 76 | NO₂ | 6 | | | CF₃ | 4 | H | | | | | | 2R, 3S, 4R |
| 77 | NH₂ | 6 | | | CF₃ | 4 | H | | | | | | 2R, 3S, 4R |
| 78 | NO₂ | 6 | | | CF₃ | 4 | H | | | | | | 2R, 3R, 4S |
| 79 | NH₂ | 6 | | | CF₃ | 4 | H | | | | | | 2R, 3R, 4S |
| 80 | NO₂ | 6 | | | OCF₃ | 4 | H | | | | | | 2S, 3S, 4R |
| 81 | NH₂ | 6 | | | OCF₃ | 4 | H | | | | | | 2S, 3S, 4R |
| 82 | NO₂ | 6 | | OH | OCF₃ | 4 | | | | | | | 2R, 3R, 4S |
| 83 | NH₂ | 6 | | OH | OCF₃ | 4 | | | | | | | 2R, 3R, 4S |
| 84 | NO₂ | 6 | | OH | OCF₃ | 4 | | | | | | | 2R, 3S, 4R |
| 85 | NH₂ | 6 | | OH | OCF₃ | 4 | | | | | | | 2R, 3S, 4R |
| 86 | NO₂ | 6 | | OC(O)CH₃ | Cl | 4 | | | | | | | 2S, 3S, 4R |
| 87 | NHC(O)CH₃ | 6 | | OC(O)CH₃ | Cl | 4 | | | | | | | 2S, 3S, 4R |
| 88 | NHC(O)CH₃ | 6 | | OH | Cl | 4 | | | | | | | 2S, 3S, 4R |
| 89 | NH₂ | 6 | | OC(O)CH₃ | Cl | 4 | | | | | | | 2S, 3S, 4R |
| 90 | Br | 6 | | OH | Cl | 4 | | | | | | | 2S, 3R, 4S |
| 91 | Br | 6 | | | Cl | 4 | | | | | | | 2R, 3R, 4S |
| 92 | Br | 6 | | | F | 4 | | | | | | | 2S, 3R, 4S |
| 93 | Br | 6 | | | F | 4 | | | | | | | 2R, 3R, 4S |
| 94 | Br | 6 | | | H | | | | | | | | 2R, 3R, 4S |
| 95 | OS(O)₂CH₃ | 6 | | | Cl | 4 | | | | | | | 2R, 3S, 4R |
| 96 | OS(O)₂CH₃ | 6 | | | Cl | 4 | | | | | | | 2S, 3S, 4R |
| 97 | OH | 6 | | | Cl | 4 | | | | | | | 2S, 3S, 4R |
| 98 | NO₂, CH₃ | 6, 5 | | | Cl | 4 | | | | | | | 2S, 3S, 4R |
| 99 | NO₂ | 6 | CH₂OCH₃ | | F | 4 | | | | | | | 2S, 3S, 4R |
| 100 | CN | 6 | CH₃ | | Cl | 4 | | | | | | | 3R, 4S |
| 101 | CN | 6 | CH₃ | | H | | | | | | | | 3R, 4S |
| 102 | OH | 6 | CH(OCH₃)₂ | | Cl | 4 | | | | | | | 2S, 3S, 4R |
| 103 | NO₂ | 8 | | | Cl | 4 | | | | | | | 2S, 3S, 4R |
| 104 | NH₂ | 8 | | | Cl | 4 | | | | | | | 2S, 3S, 4R |
| 105 | NO₂ | 8 | | | Cl | 4 | | | | | | | 2R, 3R, 4R |

TABLE 1a-continued

| Example No | R1 substituents | R1 position | R2 | R3 | R4 substituents | R4 position | R5 substituents | R5 position | R6 substituents | R6 position | n | m | stereochemistry |
|---|---|---|---|---|---|---|---|---|---|---|---|---|---|
| 106 | NH2 | 8 | | | Cl | 4 | | | | | | | 2R, 3S, 4R |
| 107 | NO2 | 6 | | | Cl | 4 | | | | | | | 2R, 3R, 4S |
| 108 | NH2 | 6 | | | Cl | 4 | | | | | | | 2R, 3R, 4S |
| 109 | NO2 | 6 | | | Cl | 4 | | | | | | | 2R, 3S, 4R |
| 110 | NH2 | 6 | | | Cl | 4 | | | | | | | 2R, 3S, 4R |
| 111 | NO2 | 6 | | | Cl | 4 | | | | | | | 2S, 3R, 4R |
| 112 | NH2 | 6 | | | Cl | 4 | | | | | | | 2S, 3R, 4R |
| 113 | NO2 | 6 | | | Cl | 4 | | | | | | | 2S, 3S, 4S |
| 114 | NH2 | 6 | | | Cl | 4 | | | | | | | 2S, 3S, 4S |
| 115 | NO2 | 6 | | | Cl | 4 | | | | | | | 2S, 3R, 4R |
| 116 | NH2 | 6 | | | Cl | 4 | | | | | | | 2S, 3R, 4R |
| 117 | NO2 | 6 | | | Cl | 4 | | | | | | | 2R, 3S, 4S |
| 118 | NH2 | 6 | | | Cl | 4 | | | | | | | 2R, 3S, 4S |

The experiment confirming the pharmacological effect of the compounds of formula 1 according to the present invention was accomplished in the below.

EXPERIMENTAL EXAMPLE 1

Vasodilating Effect on Blood Vessel Excised from Rats

The experiment confirming whether the compounds of formula 1 according to the present invention have the vasodilating effect on blood vessel was accomplished in the below.

Rats (350~450 g, obtained from the Experimental Animal Team of the Korea Research Institute of Chemical Technology) were knocked to be unconscious by hitting the occipital region, sacrificed by cervical dislocation, and underwent thoracotomy. After being quickly removed, the thoracic aorta was deprived of the adipose tissue and cut into aortic rings of 3 mm width. The aorta was lightly rubbed with cotton club soaked in a modified Krebs Henseleit buffer (Physiological salt solution) to remove the inner epithelial layer therefrom. While being hung in an organ bath containing a physiological buffer, the vascular smooth muscle was allowed to equilibrate under a resting tension of 2 g and then, stand for 1 hour at 37° C. for stabilization, supplying a carbogen consisting of 95% $O_2$~5% $CO_2$.

Thereafter, the vascular smooth muscle was constricted with $10^{-5}$M phenylephrine and washed several times with physiological saline solution. The said procedure was repeated again to ensure the stable reactivity of vascular smooth muscle to repetitive constriction/relaxation.

Thereafter, $3\times10^{-6}$ M methoxamine was applied to induce an intensive constriction in the vascular smooth muscle. When the vasoconstriction induced by the methoxamine was reached and maintained to a maximum, test compounds and control material was cumulatively added to the organ bath in concentration of 1, 3, 10 and 30 μM, respectively, to examine the vasodilating effect. Cromakalim, BMS-180448 (the compound of formula 4) and BMS-191095 (the compound of formula 5), known to be the first generation KATP opener with potent vasodilating effect were used as control materials.

The change rate of constriction by the addition of the drugs compared to the maximal constriction induced by methoxamine was calculated to plot a concentration-relaxation response curve. Through a least linear regression analysis, $IC_{50}$ that the drug concentration at which the vascular tissue is relaxed to 50% extent of the maximal constriction, was obtained for each drug. The results are shown in table 2, below.

TABLE 2

Vasodilating effect of the compounds of formula 1

| Compound | Concentration for inhibition of constriction induced by methoxamine in rat arota ($IC_{50}$, μM) |
|---|---|
| BMS-180448 (the compound of formula 4) | 1.38 |
| BMS-191095 (the compound of formula 5) | 2.14 |
| Example 1 | 7.14 |
| Example 7 | 5.59 |
| Example 10 | >30 |
| Example 11 | >30 |
| Example 17 | >30 |
| Example 22 | >30 |
| Example 24 | >30 |
| Example 25 | 27.45 |
| Example 26 | 24.6 |
| Example 28 | >30 |
| Example 31 | >30 |
| Example 32 | >30 |
| Example 34 | >30 |
| Example 61 | >30 |
| Example 65 | >30 |
| Example 70 | >30 |
| Example 75 | >30 |
| Example 77 | >30 |
| Example 81 | >30 |
| Example 83 | >30 |
| Example 85 | >30 |
| Example 98 | 7.34 |

As shown in the above table 2, Cromakalim represented a potent vasorelaxation effect having 0.067 μM of $IC_{50}$ on the isolated rat aorta constricted with methoxamine (3 μM) while $IC_{50}$s of BMS-180448 and BMS-191095 were 1.38 μM and 2.14 μM, respectively, showing twenty and thirty times weaker vasorelaxation effects than that of Cromakalim. On the other hand, the compounds of the present invention ranged, in $IC_{50}$, from 5.59 μM to greater than 30 μM, so that their vasorelaxation effects were significantly weaker than those of the controls, Cromakalim, BMS-180448 and BMS-191095.

When exerting their actions on the KATP present in the heart, the compounds according to the present invention play a role in protecting the heart. On the other hand, the KATP openers acting on the KATP present in peripheral vascular smooth muscle dilate the blood vessels, lowering the blood pressure. Hypotension may mask any cardioprotective effects due to reduction in coronary artery perfusion pressure, and would limit utility in treating myocardial ischemia. Therefore, the compounds of the present invention may be more optimal for cardioprotectives by virtue of their weak vasorelaxation activity.

EXPERIMENTAL EXAMPLE 2

Protective Effect on Iron-induced Neuronal Cells

The experiment confirming whether the compounds of formula 1 according to the present invention suppress the iron-induced neuronal cells was accomplished in the below.

From the brains of 17~18 day-old embryos, cortical neuron cells were isolated and then, cultured at 37° C. for 7~9 days in a 5% $CO_2$ incubator. The said cortical cell cultures were washed twice with MEM (Minimum essential medium) to reduce the serum level to 0.2%. Test compounds were serially diluted four times to make the final concentration of 30, 7.5, 1.875 and 0.469 μM, respectively. Then, the compound of the said concentration was pre-treated for 30 min, respectively. For the experiment, test compound was dissolved in DMSO and diluted in a medium. At this time, the final concentration of DMSO was not allowed to exceed 0.1%. For control group, only vehicle was applied.

After the said pre-treatment, $FeSO_4$ was added to the medium for a final concentration to be 50 μM. The medium was cultured in $CO_2$ incubator for 24 hours. During the incubation, lactate dehydrogenase (LDH) was released by iron. The serum level of lactate dehydrogenase released into the medium was measured to assess necrosis of neuronal cell by the oxidative toxicity of iron. The protective effect on neuron cells of the test compounds was evaluated by calculating the LDH reduction rate of treatment-group compared with that of the control group. The concentration-protective effect curve was generated and $IC_{50}$ value, drug concentration producing 50% of the maximal effect, was calculated from a least linear regression analysis. The results are shown in table 3, below.

TABLE 3

Protective effect on iron-induced neuronal cell injury

| compound | protective effect on neuron cell | |
|---|---|---|
| | Inhibition (%, 30 μM compound addition) | $IC_{50}$ (μM) |
| Example 1 | 71 | 18.1 |
| Example 7 | 59 | 34.1 |
| Example 10 | 103 | 2.2 |
| Example 11 | 93 | 2.0 |
| Example 17 | 110 | 2.0 |
| Example 22 | 97 | 5.9 |
| Example 24 | 98 | 6.1 |
| Example 25 | 83 | — |
| Example 26 | 97 | 2.2 |
| Example 28 | 103 | 4.1 |
| Example 30 | 103 | — |
| Example 31 | 86 | 1.8 |
| Example 32 | 108 | 1.6 |
| Example 33 | 91 | 6.0 |
| Example 34 | 111 | 1.5 |
| Example 42 | 103 | 2.6 |
| Example 52 | 91 | 3.0 |
| Example 54 | 98 | 1.5 |

TABLE 3-continued

Protective effect on iron-induced neuronal cell injury

| compound | protective effect on neuron cell | |
|---|---|---|
| | Inhibition (%, 30 μM compound addition) | $IC_{50}$ (μM) |
| Example 56 | 100 | 5.3 |
| Example 57 | 94 | 3.1 |
| Example 59 | 77 | 1.8 |
| Example 60 | 87 | 0.7 |
| Example 61 | 89 | 1.2 |
| Example 70 | 85 | 1.4 |
| Example 71 | 89 | 0.9 |
| Example 74 | 90 | 5.3 |
| Example 75 | 125 | 1.8 |
| Example 76 | 52 | 5.7 |
| Example 77 | 111 | 1.9 |
| Example 78 | 69 | 4.4 |
| Example 79 | 107 | 1.7 |
| Example 80 | 95 | 5.0 |
| Example 81 | 120 | 1.5 |
| Example 82 | 69 | 1.3 |
| Example 83 | 80 | 3.7 |
| Example 84 | 48 | 5.6 |
| Example 85 | 119 | 1.8 |
| Example 98 | 85 | 10.5 |
| Example 99 | 69 | 20.8 |

As shown in table 3, the compounds of the present invention had the protective effect on iron-induced neuronal cell injury. Preferably, $IC_{50}$ of the compounds prepared in example 11, 17, 31, 32, 54, 59, 61, 70, 75, 77, 79, 81, 82 and 85 were below 2 μM. More preferably, $IC_{50}$ of the compounds prepared in example 60 and 71 were below 1 μM. Therefore, the compounds of the present invention had the strong protective effect on iron-induced neuronal cell injury.

Since benzopyran derivatives substituted with secondary amine, containing tetrazole group according to the present invention had a strong protective effect on iron-induced neuron toxicity, they can be used as agents for prevention or treatment of the neurological disorders caused by the neuronal injury, such as cerebral stroke and dementia as well as inflammatory disease such as arthritis, cardiac infarction, and acute/chronic tissue damage (S. Miranda et al., The role of oxidative stress in the toxicity induced by amyloid-peptide in Alzheimer's disease Progress in Neurobiology, 2000, 62, 633-648; S. A. Cook, P. H. Sugden, A. Clerk, Regulation of Bcl-2 Family Proteins During Development and in Response to Oxidative Stress in Cardiac Myocytes Association with Changes in Mitochondrial Membrane Potential Circulation Research, 1999, 85, 940-949; J. M. McCord, The Evolution of Free Radicals and Oxidative Stress. *Am J Med,* 2000, 108, 652-659).

EXPERIMENTAL EXAMPLE 3

Protective Effect on Hydrogen Peroxide Induced Neuronal Cell Injury

The experiment confirming whether the compounds of formula 1 according to the present invention suppress the hydrogen peroxide-induced neuronal cell damage was accomplished in the below.

The same procedure as example 2 was accomplished, except for that concentration of test compound was added to be 30 μM, and the final concentration of hydrogen peroxide was 30 μM. The result was shown in table 4.

TABLE 4 protective effect on hydrogen peroxide induced neuronal cell injury

| Compound | Addition(μM) | Inhibition(%) |
|---|---|---|
| Example 11 | 30 | 96 |
| BMS-180448 | 30 | -5 |
| BMS-191095 | 30 | 27 |
| Propyl gallate | 10 | 94 |
| Promethazine | 5 | 97 |

As shown in the above, the reference compound of formula 5 (BMS-191095) exerted a protective effect (27%) at concentration of 30 μM. However, the compound of formula 11 according to the present invention had a high inhibitory rate (96%). Therefore, benzopyran derivatives substituted with secondary amine, containing tetrazole group according to the present invention had the similar protective effect to common antioxidants such as propyl gallate and promethazine. Also, the compounds of the present invention had a strong protective effect on neuron cells to the hydrogen peroxide-induced neuronal toxicity, they can be used as a therapeutic agent for prevention or treatment of the neurological disorders caused by oxidative stress-induced neuronal death, the hydrogen peroxide-induced damage or necrosis of neurons, such as cerebral stroke and dementia as well as inflammatory disease such as arthritis, cardiac infarction, and acute/chronic tissue damage (S. Miranda et al., The role of oxidative stress in the toxicity induced by amyloid-peptide in Alzheimer's disease Progress in Neurobiology, 2000, 62, 633-648; S. A. Cook, P. H. Sugden, A. Clerk, Regulation of Bcl-2 Family Proteins During Development and in Response to Oxidative Stress in Cardiac Myocytes Association with Changes in Mitochondrial Membrane Potential Circulation Research, 1999, 85, 940-949; J. M. McCord, The Evolution of Free Radicals and Oxidative Stress. *Am J Med,* 2000, 108, 652-659).

EXPERIMENTAL EXAMPLE 4

Inhibitory Effect Against Lipid Peroxidation by Iron

The experiment confirming whether the compound of formula 1 according to the present invention suppresses the iron-induced lipid peroxidation was accomplished in the below.

The rat brain was homogenized in a Krebs buffer (15 mM HEPES, 10 mM glucose, 140 mM NaCl, 3.6 mM KCl, 1.5 mM $CaCl_2$, 1.4 mM $KH_2PO_4$, 0.7 mM $MgCl_2$, PH 7.4) and the supernatant separated by centrifugation at 12,000 rpm for 10 min was used for further experiments. $FeCl_2$ was added for the final concentration to be 400 μM. Then the brain homogenate was allowed to stand at 37° C. for 30 min for the facilitation of oxidation. Each of the test compounds was added at a concentration of 100 μM. For control group, only vehicle was applied.

Iron facilitates the oxidation of the said brain homogenate to produce malondialdehyde (MDA), lipid peroxidation product. Thus, the lipid peroxidation was determined by MDA quantification. The inhibitory effect against lipid peroxidation of the test compounds was evaluated by calculating MDA reduction rate of the test compounds compared with that of the control group.

Typically, the MDA quantification is achieved by reacting samples with 2-thiobarbituric acid (TBA) and measuring the absorbance at 530 nm. However, this method is unsuitable to treat samples on a large scale because of a boiling step. Thus, in this experiment, N-methyl-2-phenylindole was used instead of TBA. In this case, one molecule of MDA reacts with two molecules of N-methyl-2-phenylindole to form a chromagen which shows a maximal absorbance at 586 nm and requires no boiling steps. Bioxytech® LPO-586 Kit was used for MDA quantification. The result was shown in table 5, below.

TABLE 5 inhibitory effect against lipid peroxidation induced by iron

| Compound | inhibitory effect against lipid peroxidation induced by iron (%, 100 μM) |
|---|---|
| Example 10 | 90 |
| Example 11 | 91 |
| Example 17 | 87 |
| Example 22 | 108 |
| Example 24 | 94 |
| Example 26 | 101 |
| Example 28 | 83 |
| Example 30 | 84 |
| Example 32 | 89 |
| Example 34 | 103 |
| Example 42 | 85 |
| Example 52 | 88 |
| Example 54 | 87 |
| Example 56 | 76 |
| Example 57 | 95 |
| Example 59 | 70 |
| Example 60 | 85 |
| Example 61 | 87 |
| Example 64 | 79 |
| Example 70 | 95 |
| Example 71 | 93 |
| Example 81 | 89 |
| Example 83 | 97 |
| Example 85 | 101 |
| Example 89 | 81 |

As shown in the above, the compounds prepared in example 10, 11, 22, 24, 26, 34, 57, 70, 71, 83, 85 and 108 had very potent inhibitory effect against the iron-induced lipid peroxidation with higher than 90% of inhibitory effect. Also, the compounds prepared in example 11, 17, 32, 54, 59, 60, 61, 70, 71, 81 and 85 had simultaneously inhibitory effect against lipid peroxidation as well as protective effect on oxidative stress induced neuronal injury by iron or copper (table 3 and 4). Therefore, the compounds of the present invention can be used as a therapeutic agent for prevention or treatment of the neurological disorders caused by the accumulation of oxidation product with facilitation of lipid peroxidation, such as cerebral stroke and dementia as well as inflammatory disease such as arthritis, cardiac infarction, and acute/chronic tissue damage (Chul Lee, Antioxidant ability of caffein and its metabolites based on the study of oxygen radical absorbing capacity and inhibition of LDL peroxidation. Clinica Chimica Acta, 2000, 295, 141-154; P-E. Chabrier et al FBN 80933, a dual inhibitor of neuronal nitric oxide synthase and lipid peroxidationL A promising neuroprotective strategy. Pro. Natl. Acad Sci USA, 1999, 96, 10824-10829).

EXPERIMENTAL EXAMPLE 5

Inhibitory Effect Against Lipid Peroxidation Induced by Copper

The experiment confirming whether the compounds of formula 1 according to the present invention suppress the copper-induced low density lipoprotein (LDL) oxidation was accomplished in the below.

Low density lipoprotein of human (human LDL, sigma) was dissolved in water to be final concentration of 1 mg/ml. To remove EDTA (ethylenediamine tetraacetate), the aqueous solution was dialyzed in phosphate buffer at 4° C. for 18 hours. At this dialysis, phosphate buffer was changed three times. Phosphate buffer was added to LDL (100 µg LDL protein/ml) which EDTA was removed from the aqueous solution, additionally thereto $CuSO_4$ 10 µM as oxidant was added. Thus, the final concentration of tocopherol for test compounds and control material was $10^{-9}$, $10^{-7}$ and $10^{-5}$ M, respectively. Group to which $CUSO_4$ was not added was used as blank group. Group to which $CUSO_4$ and vehicle were added in place of test compounds was used as control group. The mixture was incubated at 37° C. for 18 hours. EDTA 200 p M was added to the mixture to terminate the oxidation reaction.

As shown in example 4, $Cu^{2+}$ facilitates the oxidation reaction to produce malondialdehyde (MDA), lipid peroxidation product. The MDA quantification is achieved by reacting samples with 2-thiobarbituric acid (TBA) and measuring the absorbance at 530 nm. Also, 1,1,3,3-tetramethoxypropane purchased from sigma was used as standard materials. Inhibitory effect against lipid peroxidation of the test compounds was measured by MDA (nmol) to protein (mg). Decrease of MDA to that of control group was calculated. The result was shown in table 6, below.

TABLE 6

Inhibitory effect against lipid peroxidation induced by copper

| Addition(M) | Iinhibitory effect(%) | | |
|---|---|---|---|
| | Example 11 | tocopherol | Probucol |
| $10^{-7}$ | 27.3 | 21.3 | 33.7 |
| $10^{-6}$ | 54.9 | | 58.7 |
| $10^{-5}$ | 63.9 | 29.7 | 66.7 |

As shown in table 6, the compound of formula 11 of the present invention had significant inhibitory effect against lipid peroxidation induced by copper depending upon the concentration of the compounds. Also, the compound of the present invention had inhibitory effect twice as much as that of tocopherol (reference compound) at a concentration of $10^{-5}$M. Also, the compound of the present invention had inhibitory effect similar to that of probucol.

Since benzopyran derivatives substituted with secondary amine, containing tetrazole group according to the present invention had very potent inhibitory effect against the copper-induced lipid peroxidation, they can be used as an agent for prevention or treatment of the neurological disorders caused by the accumulation of oxidation product with facilitation of lipid peroxidation, such as cerebral stroke and dementia as well as inflammatory disease such as arthritis, cardiac infarction, and acute/chronic tissue damage (Chul Lee, Antioxidant ability of caffein and its metabolites based on the study of oxygen radical absorbing capacity and inhibition of LDL peroxidation. Clinica Chimica Acta, 2000, 295, 141-154; P-E. Chabrier et al FBN 80933, a dual inhibitor of neuronal nitric oxide synthase and lipid peroxidation, A promising neuroprotective strategy. Pro. Natl. Acad Sci USA, 1999, 96, 10824-10829).

EXPERIMENTAL EXAMPLE 6

Inhibitory Effect on Accumulation of Reactive Oxygen Species Induced by Hydrogen Peroxide The experiment confirming whether the compounds of formula 1 according to the present invention suppress the hydrogen peroxide-induced reactive oxygen species was accomplished in the below.

To measure reactive oxygen species, $H_2DCFDA$ (2',7'-dichlorodihydrofluorescein diacetate, Molecular Probes, Eugene, Oreg., USA) was used. If $H_2DCFDA$, nonpolar material is transferred through cell membrane, it is changed to $H_2DCF$ (2',7'-dichlorodihydrofluorescein), material impermeable to membrane by intracellular esterase. H2DCF is changed to high fluorescent DCF (2',7'-dichlorofluorescein) by low fluorescent peroxidated oxygen or hydroxyl radical. $H_2DCFDA$ solution (10 mM) dissolved in DMSO was used before the experiment. A7r5 (Rat thoracic aorta smooth muscle cell line, ATCC), as smooth muscle cell was incubated in DMEM (Dulbecco's Modified Eagle's Medium) containing 10% of FBS (fetal bovine serum). Thereafter, the cell was incubated in 48 well plate for two days, then was incubated in serum-free DMEM for 24 hours to use for experiment. Krebs-linger buffer (Krebs-Ringer (K-R), 99.01 mM NaCl, 4.69 mM KCl, 1.87 mM $CaCl_2$, 1.2 mM $MgSO_4$, 1.03 mM $K_2HPO_4$, 25 mM $NaHCO_3$, 20 mM Hepes, 11.1 mM D-glucose, pH 7.4) was used for washing and process of cell monolayers. After cell monolayers media was removed, each of test compounds (0.2 ml) was pre-treated to media, then incubated at 37° C. for 15 min. Final concentration was 50 µM, hydrogen peroxide was added. The media was allowed to stand for 30 min. The said solution from media was removed. The media was washed one time. $H_2DCFDA$ 20 µM was added to the media. The media was allowed to stand for 30 min. the media was washed two times. Thereafter, oxidation of $H_2DCFDA$ was measured by Fluorescence reader (FL600, Biotech Instruments, 485 nm excitation, 530 nm emission). The result was shown in table 7.

TABLE 7

Inhibitory effect against reactive oxygen species accumulation

| Compound | addition(µM) | Inhibitory(%) |
|---|---|---|
| Example 11 | 30 | 124 |
| Example 11 | 10 | 82 |
| Example 11 | 3 | 6 |
| Propyl gallate | 30 | 108 |
| Propyl gallate | 10 | 94 |
| Propyl gallate | 3 | 57 |

If hydrogen peroxide was added to A7r5 cells, cell damage was induced by reactive oxygen species, which led to the increase in DCF fluorescence. However, the increase in DCF fluorescence induced by hydrogen peroxide was inhibited by treatment of the compound of formula 11 of the present invention, in a dose dependent manner. Most preferably, DCF fluorescence was completely inhibited by treatment of 30 µM. Since the compound of formula 11 of the present invention had potent inhibitory effect against reactive oxygen species accumulation induced by hydrogen peroxide, they can be used as a therapeutic agent for prevention or treatment of the neurological disorders caused by the accumulation of oxidation product with facilitation of lipid peroxidation, such as cerebral stroke and dementia as well as inflammatory disease such as arthritis, cardiac infarction, and acute/chronic tissue damage (G. J. Gross, J. R. Kersten, D. C. Warltier Mechanism of post ischemic contractile dysfunction Ann Thoar Sur, 1999, 68, 1898-1904; S. Okubo, Myocardial preconditioning: Basic concepts and potential mechanisms. Molecular and Cellular Biochemistry 1999, 196, 3-12; I Cantuti-Castelvetri, B. Shukitt-HAle, J. A. Joseph, Neurobehavioral aspects of antioxidants in aging Int. J. Neuroscience, 2000, 18, 267-381).

EXPERIMENTAL EXAMPLE 7

Protective Effect on Brain Damage Induced by Brain Ischemia-reperfusion

The experiment confirming whether the compound of formula 1 according to the present invention has the protective effect on brain damage induced by ischemia-reperfusion was accomplished in the below.

Male rat (Sprague-Dawley Rat, 350±50 g, Samyook) was anesthetized by administration of Pentobarbital sodium 40 mg/Kg. PE-19 tubing was inserted to the femoral vein and the artery, left carotid artery was exposed. Before the operation, heparin sulfate 20 μg was injected to the peritoneal cavity. Blood pressure measuring device was inserted to the femoral artery for the continuous measurement of arterial pressure. Blood (10 ml) was collected from the femoral vein to decrease blood pressure to 30 mmHg. If blood pressure is not decreased to 100 mmHg by collection of blood (7 ml), it is evaluated that sympathetic tone is very high. The said case was excluded for experiment, for mortality of rats is high 30 mmHg or even after success in reducing the blood pressure, the rats showed high mortality after the operation.

With blood pressure maintaining to be 30 mmHg, left carotid artery was closed by aneurysm clamp for 20 min to induce ischemia. Reperfusion was accomplished by the collected blood and 0.84% bicarbonate saline (5 ml). Body temperature of rats was constantly maintained to be 37±0.5° C., by using thermal blanket and incandescent light bulbs during the ischemia. After the operation, in recovering period, body temperature was constantly maintained for more than 2 hours. If rats were recovered entirely, they were transferred to animal laboratory. Condition of animal laboratory, such as temperature, humidity and light cycle was constantly maintained to be 27° C., 60% and 12-21 hours, respectively.

After 24 hours from the operation, rats were sacrificed. Then brain was enucleated from rat within 3 min. Enucleated brain was excised on the ice at the interval 2 mm by using brain matrix to produce six coronal sections. The said coronal sections were dyed in 2% 2,3,5-triphenyltetrazolium chloride solution at 37° C. for 30 min. The said dyed coronal section was developed and printed. Thereafter, the ratio of necrosis area to brain area was measured by using Image Analyzer.

Otherwise, test compounds were four times administered to abdominal cavity at a dose 30 mg/kg. Particularly, test compounds were administrated before 30 min prior to operation as well as after 2, 4, 16 hours from carotid artery closing. For a control group, vehicle was only administrated to the rat in place of test compounds. For a comparative group, (5R,10S)-(+)-5-methyl-10,11-dihydro-5H-dibenzo-[a,d]cyclohepten-5,10-imine hydrogen maleate (MK 801) as noncompetitive NMDA N-methyl-D-aspartate was administrated to the rats.

The protective effect on brain damage induced by brain ischemia-reperfusion was evaluated by calculating reduction of necrosis area to that of brain for a control group. The result was shown in table 8.

TABLE 8

Protective effect on brain damage induced by brain ischemia-reperfusion

| Test compound | Dose (mg/kg) | n number | Infarction volume Medium(%) | Decrease(%) |
|---|---|---|---|---|
| Control | | 13 | 40.3 ± 5.5 | |
| Comparative (MK 801) | 30 | 11 | 29.8 ± 4.9 | 25.9 |
| Example 11 | 30 | 14 | 21.5 ± 2.6 | 46.3 |

As shown in table 8, infarct volume of comparative group to which MK 801 was administrated at a dose of 30 mg/Kg was 29.8%, which resulted in reduction of the infarct volume by 24.8% relative to that of control group.

Otherwise, infarct volume of test group to which the compound of formula 11 was administrated at a dose of 30 mg/kg was 21.5%, which resulted in reduction of the infarct volume by 46.3% relative to that of control group. Therefore, the compound of the present invention had the protective effect on the brain damage induced by brain ischemia-reperfusion two times as much as the reference compound, MK 801 did.

Also, in MK 801-treated group as the comparative group, the side effect such as decrease in mobility in rats was observed. However, in the group to which the compound of formula 11 was administrated, the side effects including changes in motility were not observed. As shown in the table 2, due to the weak vasodilating effect ($IC_{50}$>30 μM) of the compound of the present invention, side effect induced by decrease in perfusion to the ischemic brain was greatly reduced.

Since benzopyran derivatives substituted with secondary amine, containing tetrazole group had the excellent protective effect on the brain damage induced by brain ischemia-reperfusion, they can be used as an agent for the prevention or treatment of disease caused by brain damage, such as cerebral stroke or dementia (E. V. Golanov, J. D. Christensen, D. J. Reis, Role of potassium channels in the central neurogenic neuroprotection elicited by cerebellar stimulation in rat. Brain Research, 1999, 842, 496-500).

EXPERIMENTAL EXAMPLE 8

Protective Effect on Ischemic-hypoxic Brain Injury

The experiment confirming whether the compound of formula 1 of the present invention had protective effect on ischemic-hypoxic brain injury, using MRS (magnetic resonance spectrum) was accomplished in the below.

It was reported that in ischemic-hypoxic model of rats, histological test result was significantly correlated to the change of magnetic resonance spectrum. By using the said report, the protective effect on brain damage induced by hypoxia in vitro was investigated. [Van der A. Toorn et al. Magnetic Resonance in Medicine, 1996, 36, 914-922]. It was reported that the lipid peak was increased in MRS by ischemic neuronal cell injury due to the destruction of cell membrane including blood-brain barrier. Also, it was reported that increase of lipid concentration was correlated to apoptosis. [A. Bizzi et al., Magnetic Resonance Imaging, 1996, 14, 581-592]. Therefore, it was reported that Lipid/NAA and Lipid/Cr obtained by comparing lipid with N-acetylaspartate (NAA) and creatine (Cr) as marker of neuronal cell was correlated to morphological changes and severity of apoptosis on hypoxic brain damage.

In new born rats (within 7 days, 10~15 g), left carotid artery were intermitted for 3 hours to induce hypoxia. Test compounds were intraperitoneally injected before 1 hour of hypoxia. Left eye of which the carotid artery was intermitted was used as ischemic-hypoxic model, right eye of which the carotid artery was not intermitted was used as hypoxic model. Magnetic resonance spectrum was obtained from both models, after histological test, accomplished in one day from damage. From the said result, Lipid/NAA or Lipid/Cr was measured. Also, viability and morphological score by macroscopic observation of infarct volume was calculated. The result was shown in table 9.

TABLE 9 protective effect on hypoxic brain damage

| | Control | | Example 11 (50 mg/kg) | |
|---|---|---|---|---|
| | Ischemic-hypoxic | hypoxic | Ischemic-hypoxic | Hypoxic |
| Lip/NAA | 11.55 | 4.63 | 5.43 | 1.69 |
| Lip/Cr | 13.90 | 4.11 | 5.16 | 1.55 |
| Survival | 13/26(50%) | | 19/24(79%) | |
| Morphological score | 3.0 | | 1.4 | |

As shown in table 9, the compound of formula 11 of the present invention reduced Lip/NAA and Lip/Cr obtained from magnetic resonance spectrum in ischemic-hypoxic or hypoxic new born rat model, two times or three times as much as that of control group, respectively. Therefore, the compound of the present invention had protective effect on brain damage. Also, in the comparison of viability, the compound of formula 11 significantly increased viability to 79%, more than that of control group (50%). The compound of formula 11 decreased morphological score obtained from macroscopic observation of infarct volume two times as low as that of control group.

Since benzopyran derivatives substituted with secondary amine, containing tetrazole group according to the present invention had protective effect on brain damage induced by ischemic-hypoxic or hypoxia. Therefore, the compound of the present invention can be used as an agent for prevention or treatment of newborn hypoxia (C. C. Huang et al Measurement of the urinary lactate:creatinine ratio for the early identification of newborn infants at risk for hypoxic-ischemic encephalopathy. New England J. of Medicine, 1999, 341 (5), 328-335).

EXPERIMENTAL EXAMPLE 9

Protective Effect on Neuronal Cells Damage by Axotomy of Optic Nerve

The experiment whether the compound of formula 1 of the present invention had protective effect on the cell neuronal damage induced by axotomy of optic nerve was shown in the below.

Test compounds were dissolved in DMSO to prepare stock solution (100 mM), which was diluted with physiological saline to the 20 µM. 10 µl of stock solution was injected vitreously.

Adult rats were anesthetized with chloral hydrate (400 mg/Kg), then optic nerve was exposed by bulbar conjunctiva. Thereafter, nerve corresponding to 0.5 mm or 3 mm from eye ball was excised, respectively. Or through upper eyelid cutaneous amputation was accomplished, then part of lacrimal gland was removed. Onto eye ball superior rectus muscle was excised in the ocular muscles to expose the optic nerve. The optic nerve was excised about 5 mm back from eye ball. Blood vessels of retina supplying blood to retina was not impaired. Condition of blood vessels of retina was checked with funduscope. Fluorogold (Fluorochrome Inc. 5% in PBS (phosphate buffered solution) was administrated to Half of test group, in the retrograde after axotomy of optic nerve. To investigate cell survival of the ganglion after axotomy, eyes was removed from rats, then retina was isolated in 3 days, 1 week, 2 weeks, 4 weeks, 2 months, 4 months, and 6 months. The isolated retina was investigated by transmission electron microscope. For quantitative analysis, at the same time tissue of retina was prepared. The prepared tissue was investigated by immunochemical dyeing or fluorescent microscope to which 530~560 nm filter was installed. The results were shown in table 10.

TABLE 10 protective effect on neuronal cells injury induced by axotomy of optic nerve

| | Survival of the ganglion cell(%) |
|---|---|
| Control | 22% |
| Example 11 (20 µM) | 43% |

As shown in table 10, after axotomy of optic nerve, survival rate of retina ganglion cell from control group was 22%. However, survival rate of retina ganglion cell from test group to which the compound of formula 11 was administrated at a concentration of 20 µM was 43%. Therefore, the compound of formula 11 significantly increased survival rate.

Since benzopyran derivatives substituted with secondary amine, containing tetrazole group had the protective effect on death of retina ganglion cell injury induced by axotomy of optic nerve, they can be used as an agent for prevention or treatment of glaucoma induced by impairment of ganglion cell (P. Hardy et al. Oxidant, nitric oxide and prostanoids in the developing ocular vasculature: a basis for ischemic retinopathy Car diovascular Research, 2000, 47, 489-509).

EXPERIMENTAL EXAMPLE 10

Effect on Motor Nerve Conduction Velocity in Diabetic Rats

The experiment confirming whether the compounds of formula 1 improve impaired motor nerve conduction velocity in diabetic rats was accomplished in the below.

Diabetes was induced with injection of Streptozotocin (65 mg/kg) in rats, then test compounds dissolved in 2 ml of media (physiological saline:ethanol:tween 80=1:1:1) were orally administrated once a day. Rats were anesthetized with pentotal, then the sciatic nerve was exposed to measure motor nerve conduction velocity. The nerve was stimulated at two points. The first stimulus electrode was inserted at proximal end, and second electrode stimulus electrode was inserted at the distal notch. The coaxia needle electrode was inserted into interdigitala muscle, then the muscle action potential induced by two points stimulation. The conduction velocity was calculated by dividing the distance between two stimulus points by the latency differences. Lipoic acid (100 mg/kg) was used in comparison with the compound of the present invention in recovery of impaired Motor Nerve Conduction Velocity (MNCV) in diabetic rats. The recovery (%) of Motor Nerve Conduction was calculated according to the following mathematical formula 1. The results were shown in table 11.

MATHEMATICAL FORMULA 1 recovery (%) of *MotorNerve* Conduction =

-continued $$\frac{(MNCV \text{ of the compound treated rats} - MNCV \text{ of diabetic rats})}{(MNCV \text{ of normal rats} - MNCV \text{ of diabetic rats})} \times 100$$

TABLE 11 effect on motor nerve conduction velocity in diabetic rats

|  | MNCV(msec) | Recovery(%) |
| --- | --- | --- |
| Normal | 59.78 | 100- |
| Diabetic | 49.03 | — |
| Example 11 (50 mg/kg) | 53.95 | 45.8 |

As shown in table 11, MNCV of diabetic rats were significantly decreased compared to that of normal control group. Administration of the compound of formula 11 at the dose of 50 mg/kg significantly improved MNCV in diabetic rats.

Since benzopyran derivatives substituted with secondary amine, containing tetrazole group according to the present invention improved MNCV in diabetic rats, they can be used as an agent for prevention or treatment of diabetic neuropathy or diabetic peripheral nerve disorder (K. Naka et al. Effects of stazol on development of experimental diabetic neuropathy: functional and structural studies, and $Na^+$-$K^+$-ATPase acidity in peripheral nerve in rats with streptozocin-induced diabetes. Diabetes Res. and Clinical Practice, 1995, 30, 153-162)

EXPERIMENTAL EXAMPLE 11

Inhibitory Effect on NO Production

The experiment confirming whether the compounds of formula 1 had an inhibitory effect on NO (nitric oxide) was accomplished in the below.

Using RPMI1640 media supplemented with 10% fetal bovine serum (FBS), RAW 264.7 cells (obtained from American Type Culture Collection), a murine macrophage cell line, were cultured at 37° C. in a 5% $CO_2$ incubator. The RAW 264.7 cells were harvested and cell density was adjusted to $5 \times 10^5$ cell/ml with a RPMI media supplemented with 0.5% FBS and plated at $5 \times 10^4$ cell/well to 96-well plate, which were then cultured for 20 hours in a $CO_2$ incubator. After removal of the media, the cells were pre-treated for 1 hour with fresh media containing 30 μM. The test compounds were dissolved in DMSO and diluted to respective concentration in the media. In order to minimize DMSO effect on the nitric oxide formation by the RAW 264.7 cells in the walls, the media were allowed to contain DMSO at a concentration of 0.1% or less.

After completion of one-hour pre-treatment, Lipopolysaccharide (*E. coli* serotype 055:B5) was added to activate the cells at a final concentration of 1 μg/ml, which were maintained for 24 hours in a $CO_2$ incubator. As a result of the activation of RAW 264.7 cells with LPS, NO was formed. The NO release into the media was in a form of nitrite ($NO_2^-$) and quantitatively measured using the Griess reagent. A control group was treated only with vehicle instead of test compounds. Using nitrite standard, it was shown that the test drugs themselves do not hinder the quantification of NO.

The inhibitory effect of the test compounds against NO production were determined as the reduction of NO quantity compared with that of the control group. The results were shown in table 12.

TABLE 12 inhibitory effect against No production

| Compound | Addition (μM) | Inihibition (%) |
| --- | --- | --- |
| Example 11 | 30 | 27 |
| Example 29 | 30 | 79 |
| Example 45 | 30 | 75 |
| Example 47 | 30 | 62 |
| Example 51 | 30 | 96 |
| Example 53 | 30 | 96 |
| Example 58 | 30 | 76 |
| Example 60 | 30 | 86 |
| Example 68 | 30 | 64 |
| Example 70 | 30 | 75 |

As shown in table 12, benzopyran derivatives substituted with secondary amine, containing tetrazol group according to the present invention had inhibitory effect against production of NO induced by endotoxin such as LPS. Preferably, the compounds prepared in example 29, 45, 58, 60 and 70 had inhibitory effect more than 75% at the concentration of 30 μM. Most preferably, the compounds prepared in example 51 and 53 had inhibitory effect more than 90% at the same concentration.

Since benzopyran derivatives substituted with secondary amine, containing tetrazole group according to the present invention had potent inhibitory effect against NO production, they can be used as an agent for prevention or treatment of the neurological disorders caused by excess production of NO, such as cerebral stroke and dementia as well as inflammatory disease such as arthritis, cardiac infarction, and acute/chronic tissue damage (J. F. Kerwin Jr. Nitric oxide: A New Paradigm for second Messengers J. Med. Chem, 1995, 38, 4343-4362).

EXPERIMENTAL EXAMPLE 12

Cardioprotective Effect in Ischemic Heart Models of Rats

The experiment confirming whether the compound of formula 1 had the protective effect (anti-ischemic effect) on ischemic heart was accomplished in the below.

Male rats (300~450 g, obtained form the experimental animal team of the Korea Research Institute of Chemical Technology) were anaesthetized by the intra-peritoneal injection of sodium pentobarbital at a dose of 100 mg/kg. Heparin (1,000 U/kg) was injected to the tail vein and then the heart was enucleated. Particularly, cannula (PE 240) was inserted to the organ. Rats were mechanically ventilated with a rodent ventilator, in situ aorta cannula was inserted into their aorta. In retorgrade perfusion, their hearts were enucleated, then just hung onto Langendorff Apparatus. Tissue attached at the heart was removed. Heart was perfused in oxygenated modified Krebs-Henseleit bicarbonate buffer (composition<mM/L>116 NaCl, 4.7 KCl, 1.1 $MgSO_4$, 1.17 $KH_2PO_4$, 24.9 $NaHCO_3$, 2.52 $CaCl_2$, 8.32 Glucose, 2.0 Pyruvate) at a constant perfusion pressure (85 mmHg). A metal cannula attached to latex balloon filled with solvent (ethanol: water=1:1 (v/v)) was placed in the left ventricle through pulmonary vein and connected to a isovolumetric pressure transducer (H.S.E., Germany) for measurement of left ventricular pressure (LVP). The hearts were allowed to equilibrate for 15 min, at which time left ventricular end-diastolic pressure (EDP) was adjusted to 5 mmHg and this balloon volume was maintained throughout the experiment.

Baseline cardiac contractile function, heart rate (HR), and coronary flow (CF) were measured. Cardiac contractile function was calculated by substracting LVSP (left ventricular peak systolic pressure) from LVEDP (left ventricular end diastolic pressure), yielding LVDP (left ventricular developed pressure). Double product RPP (rate-pressure product) (DP), another important parameter for indirectly assessing cardiac performance in Langendorff heart impossible to measure cardiac output was calculated by multiplying HR by LVDP.

Throughout the experiment, total coronary blood flow was measured by the use of coronary flow probe (diameter: 1.0 mm) installed in aortic cannula with electromagnetic flowmeter. Temperature of heart was steadily maintained by immersing the heart at 37° C. in physiological saline solution to which 95% $O_2$/5% $CO_2$ was constantly supplied. After stabilization for 15 min, the hearts were pre-treated for 10 min in vehicle (0.04% DMSO) or mixture containing the compound of the present invention or control material. Thereafter, cardiac contractile function, HR and CF were repeatedly measured. Global ischemia was induced by completely shutting off the perfusate for 30 min. Severity of ischemia was determined as the time to contracture (TTC, min) during global ischemia in which the first 5 mmHg increase in EDP was observed. Then, the hearts were reperfused and, 30 min later, contractile functions (LVDP, HR and CF) was repeatedly measured. After reperfusion was accomplished for 30 min, LDH (lactate dehydrogenase) was measured as a sensitive index for loss of cell viability with a kit. The results were shown in table 13.

TABLE 13 cardioprotective effect in ischemic heart models of rats

| Test compound | Cardioprotective effect in ischemic heart models of rats (10 μM) | | | |
|---|---|---|---|---|
| | LVDP X HR (%) | EDP (mmHg) | TTC (min) | LDH (u/g) |
| Vehicle | 23.0 | 43.4 | 20.3 | 29.9 |
| BMS-180448 | 67.6 | 16.5 | 27.8 | 17.2 |
| Example 1 | 46.8 | 29.3 | 24.8 | 15.2 |
| Example 11 | 24.8 | 47.6 | 19.9 | 16.5 |
| Example 32 | 64.7 | 17.0 | 27.9 | 15.7 |
| Example 61 | 52.7 | 23.0 | 20.0 | 22.4 |
| Example 70 | 31.9 | 37.0 | 22.0 | 18.4 |

In vehicle-treated group, reperfusion DP (LVDP×HR) a index for contractility function, was decreased to 23.0% of pre-treatment DP, and EDP was increased to 43.3 mmHg from 5 mmHg, and TTC was 20.3 min, and reperfusion LDH release was 29.9 u/g as shown in the above.

In BMS-180448 treated group, reperfusion contractile function (DP, LVDP×HR) was 67.6% of pre-treatment DP, which was significantly improved compared to vehicle treated group. EDP was 16.5 mmHg, significantly lower than control, and TTC was 27.8 min, prolonged than control, and reperfusion LDH release was 17.2 U/g, decreased than control. Then, in BMS-180448 treated group all parameters showed significant protective effect on ischemic heart.

When compared only in anti-ischemic effect from those parameters, cardiac contractile function, EDP, TTC, and LDH release, the compounds of the present invention were similar to or superior to BMS-180448. However, because the compounds of the present invention are remarkably lower vasorelaxant effect than BMS-180448 dose, they are far superior to the conventional drug in cardioselective antiischemic activity. Especially, the compound of example 30 showed a good cardioprotective effect, of which contractile function (LVDP×HR) was improved to 64.7% of pre-treatment index, and EDP was 17.0 mmHg, and TTC was 27.9 min, and reperfusion LDH release was 15.7 U/g, with very low vasodilation activity. So, it shows much better cardioselectivity upon vasodilation than is BMS-180448. Consequently, the compounds of the present invention can be used for the treatment of ischemic heart disease by virtue of their excellent selectivity and protective activity against ischemic cardiovascular disease. In addition, the compounds prepared in example 1, 11 and 32 of the present invention had the excellent protective effect against the cell damage by ischemia-reperfusion by decreasing reperfusion LDH release.

Since benzopyran derivatives substituted with secondary amine, containing tetrazole group according to the present invention had the protective effect on ischemic heart, similar to or superior to that of BMS-180448, more preferably they had low vasodilating effect relative to BMS-180448, they can be used as an agent for prevention or treatment of heart infarction, heart failure or angina by virtue of their excellent selectivity and protective activity (T. Miura et al. Roles of Mitochondrial ATP-sensitive K Channels and PKC in Anti-Infarct Tolerance afforded by Adenosine A1 receptor Activation. J Am Coll Cardiol, 1999, 35, 238-45; D. J. Chambers, D. J. Hearse Developments in Cardioprotection: "Polarized" Arrest as an Alternative to "Depolarized" Arrest Ann. Thorc. Surg, 1999, 68, 1960-6).

EXPERIMENTAL EXAMPLE 13

Inhibitory Effect Against HUVEC Tube Formation

The experiment confirming whether the compounds of the present invention had inhibitory effect against HUVEC tube formation was accomplished in the below.

HUVEC (Human Umbilical Vein Endothelial Cell) were cultured, and tubulogenesis (tube formation) was induced in vascular endothelial cells by plating them onto the surface of Matrigel for several hours. The effect on tube formation of the test compounds were compared with the vehicle-treated control group, then confirmed their in-vitro anti-angiogenic effect indirectly. The results were shown in table 14.

TABLE 14

| inhibitory effect against HUVEC tube formation | | |
|---|---|---|
| | Tube formation | |
| Control | 10 μM | 100 μM |
| Example 2 | + | ++ |
| Example 28 | +/− | + |

−: no effect,
+/−: slight effect
+: medium effect
++: strong effect

As shown in table 14, HUVEC tube formation was inhibited at concentration of 10 μM, and strongly inhibited at concentration of 100 μM in the compound prepared in example 2, in a concentration dependent manner. Also, the compound prepared in example 28 had inhibitory effect against tube formation, to suppress angiogenesis Since benzopyran derivatives substituted with secondary amine, containing tetrazole group according to the present invention had potent inhibitory effect against angiogenesis, they can be used for the medical treatment of various diseases related to angiogenesis, such as rheumatoid arthritis, psoriasis, AIDS complication, cancers, diabetic retinopathy, etc (P.

A. Burke, S. J. DeNardo Antiangiogenic agents and their promising potential in combined therapy. Critical Reviews in Oncology/Hematology, 2001, 39, 155-171).

EXPERIMENTAL EXAMPLE 14

Acute Oral Toxicity Test in Rats

The experiment confirming whether the compound of formula 1 of the present invention had acute oral toxicity was accomplished in the below.

In this test, six-week old SPF SD rats were used with two rats assigned to each group. Each group was consisted of two rats. The compounds prepared in example 1, 7, 11, 17, 22, 24, 26, 28, 30, 32, 34, 42, 52, 54, 55, 56, 57, 59, 60, 61, 70, 75, 77, 79, 81, 83, 85, and 89 were suspended in 0.5% methyl cellulose, respectively. Then, the suspensions were administrated orally at a single dose of 1 g/kg/15 ml. after the administration, the animals were observed for clinical signs of toxicity or mortality and the body weight changes were measured. Also, hematological test and biochemical analysis were accomplished. After sacrificing the animals, autopsy was performed for macroscopic observations of the organs and tissues. As a result, there was no significant changes in clinical symptoms, body weight and mortalities. Also in hematology, serum chemistry parameters, macroscopic observation and drug-related changes were not observed. As a result all the compounds tested did not show toxicity in rats up to a dose of 2 g/kg, and the lethal dose ($LD_{50}$) for oral administration was determined to be over 2 g/kg.

What is claimed is:

1. A compound represented by following formula 1, stereoisomer thereof or pharmaceutically acceptable salt thereof:

FORMULA 1

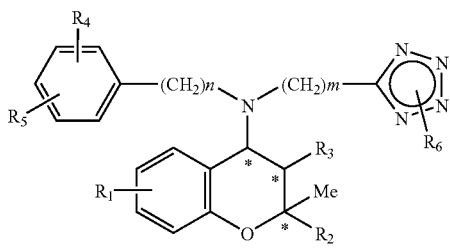

wherein, $R_1$ is Br, $NO_2$, CN, OH, $NH_2$,

or $OSO_2R^a$ provided that $R^a$ is $C_1$-$C_4$ straight or branched alkyl;

$R_2$ is $CH_2OR^a$ or

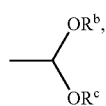

provided that $R^a$ is as defined in the above, $R^b$ and $R^c$ are independently $C_1$-$C_4$ straight or branched alkyl;

$R_3$ is OH or

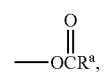

provided that $R^a$ is as defined in the above;

$R_4$ is H, F, Cl, $C_1$-$C_3$ straight or branched alkyl, $OR^a$, $CF_3$, $OCF_3$, $NO_2$, $CH(OH)CH_3$,

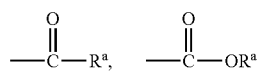

or $SO_3R^a$, provided that $R^a$ is as defined in the above;

$R_5$ is H, $OH_3$ or $OR^a$, provided that $R^a$ is as defined in the above;

$R_6$ is H, $C_1$-$C_3$ straight or branched alkyl;

n is 0 or 1 and m is 1;

\* represent a chiral carbon.

2. The compound of formula 1 according to claim 1, stereoisomer thereof or pharmaceutically acceptable salt thereof, the compound of formula 1 is selected from the group consisting of:

1) (2S,3S,4R)-6-nitro-4-[N-(4-chlorophenyl)-N-(2-methyl-2H-tetrazol-5-ylmethyl)amino]-3-hydroxy-2-methyl-2-dimethoxymethyl-3,4-dihydro-2H-1-benzopyran;

2) (2S,3R,4S)-6-nitro-4-[N-(4-chlorophenyl)-N-(2-methyl-2H-tetrazol-5-ylmethyl)amino]-3-hydroxy-2-methyl-2-dimethoxymethyl-3,4-dihydro-2H-1-benzopyran;

3) (2S,3S,4R)-6-nitro-4-[N-(2-methyl-2H-tetrazol-5-ylmethyl)phenylamino]-3-hydroxy-2-methyl-2-dimethoxymethyl-3,4-dihydro-2H-1-benzopyran;

4) (2S,3R,4S)-6-nitro-4-[N-(2-methyl-2H-tetrazol-5-ylmethyl)phenylamino]-3-hydroxy-2-methyl-2-dimethoxymethyl-3,4-dihydro-2H-1-benzopyran;

5) (2S,3S,4R)-6-nitro-4-[N-(4-fluorophenyl)-N-(2-methyl-2H-tetrazol-5-ylmethyl)amino]-3-hydroxy-2-methyl-2-dimethoxymethyl-3,4-dihydro-2H-1-benzopyran;

6) (2S,3R,4S)-6-nitro-4-[N-(4-fluorophenyl)-N-(2-methyl-2H-tetrazol-5-ylmethyl)amino]-3-hydroxy-2-methyl-2-dimethoxymethyl-3,4-dihydro-2H-1-benzopyran;

7) (2S,3S,4R)-6-nitro-4-[N-benzyl-N-(2-methyl-2H-tetrazo-5-ylmethyl)amino]-3-hydroxy-2-methyl-2-dimethoxymethyl-3,4-dihydro-2H-1-benzopyran;

8) (2S,3R,4S)-6-nitro-4-[N-benzyl-N-(2-methyl-2H-tetrazol-5-ylmethyl)amino]-3-hydroxy-2-methyl-2-dimethoxymethyl-3,4-dihydro-2H-1-benzopyran;

9) (2S,3S,4R)-6-nitro-4-[N-(4-nitrophenyl)-N-(2-methyl-2H-tetrazol-5-ylmethyl)amino]-3-hydroxy-2-methyl-2-dimethoxymethyl-3,4-dihydro-2H-1-benzopyran;

10) (2S,3S,4R)-6-amino-4-[N-(4-chlorophenyl)-N-(2-methyl-2H-tetrazol-5-ylmethyl)amino]-3-hydroxy-2-methyl-2-dimethoxymethyl-3,4-dihydro-2H-1-benzopyran;

11) (2S,3R,4S)-6-amino-4-[N-(4-chlorophenyl)-N-(2-methyl-2H-tetrazol-5-ylmethyl)amino]-3-hydroxy-2-methyl-2-dimethoxymethyl-3,4-dihydro-2H-1-benzopyran;

12) (2S,3S,4R)-6-nitro-4-[N-(4-chlorophenyl)-N-(1-methyl-1H-tetrazol-5-ylmethyl)amino]-3-hydroxy-2-methyl-2-dimethoxymethyl-3,4-dihydro-2H-1-benzopyran;

13) (2S,3S,4R)-6-nitro-4-[N-(1-methyl-1H-tetrazol-5-ylmethyl)phenylamino]-3-hydroxy-2-methyl-2-dimethoxymethyl-3,4-dihydro-2H-1-benzopyran;

14) (2S,3S,4R)-6-nitro-4-[N-(4-fluorophenyl)-N-(1-methyl-1H-tetrazol-5-ylmethyl)amino]-3-hydroxy-2-methyl-2-dimethoxymethyl-3,4-dihydro-2H-1-benzopyran;

15) (2S,3S,4R)-6-nitro-4-[N-benzyl-N-(1-methyl-1H-tetrazol-5-ylmethyl)amino]-3-hydroxy-2-methyl-2-dimethoxymethyl-3,4-dihydro-2H-1-benzopyran;

16) (2S,3R,4S)-6-nitro-4-[N-benzyl-N-(1-methyl-1H-tetrazol-5-ylmethyl)amino]-3-hydroxy-2-methyl-2-dimethoxymethyl-3,4-dihydro-2H-1-benzopyran;

17) (2S,3S,4R)-6-amino-4-[N-(4-chlorophenyl)-N-(1-methyl-1H-tetrazol-5-ylmethyl)amino]-3-hydroxy-2-methyl-2-dimethoxymethyl-3,4-dihydro-2H-1-benzopyran;

18) (2S,3S,4R)-6-nitro-4-[N-(4-chlorophenyl)-N-(1H-tetrazol-5-ylmethyl)amino]-3-hydroxy-2-methyl-2-dimethoxymethyl-3,4-dihydro-2H-1-benzopyran;

19) (2S,3S,4R)-6-nitro-4-[N-(1H-tetrazol-5-ylmethyl)phenylamino]-3-hydroxy-2-methyl-2-dimethoxymethyl-3,4-dihydro-2H-1-benzopyran;

20) (2S,3S,4R)-6-nitro-4-[N-benzyl-N-(1H-tetrazol-5-ylmethyl)amino]-3-hydroxy-2-methyl-2-dimethoxymethyl-3,4-dihydro-2H-1-benzopyran;

21) (2S,3S,4R)-6-nitro-4[N-(3-chlorophenyl)-N-(2-methyl-2H-tetrazol-5-ylmethyl)amino]-3-hydroxy-2-methyl-2-dimethoxymethyl-3,4-dihydro-2H-1-benzopyran;

22) (2S,3S,4R)-6-amino-4-[N-(3-chlorophenyl)-N-(2-methyl-2H-tetrazol-5-ylmethyl)amino]-3-hydroxy-2-methyl-2-dimethoxymethyl-3,4-dihydro-2H-1-benzopyran;

23) (2S,3S,4R)-6-nitro-4-[N-(4-methylphenyl)-N-(2-methyl-2H-tetrazol-5-ylmethyl)amino]-3-hydroxy-2-methyl-2-dimethoxymethyl-3,4-dihydro-2H-1-benzopyran;

24) (2S,3S,4R)-6-amino-4-[N-(4-methylphenyl)-N-(2-methyl-2H-tetrazol-5-ylmethyl)amino]-3-hydroxy-2-methyl-2-dimethoxymethyl-3,4-dihydro-2H-1-benzopyran;

25) (2S,3R,4S)-6-nitro-4-[N-(3-chlorophenyl)-N-(2-methyl-2H-tetrazol-5-ylmethyl)amino]-3-hydroxy-2-methyl-2-dimethoxymethyl-3,4-dihydro-2H-1-benzopyran;

26) (2S,3R,4S)-6-amino-4-[N-(3-chlorophenyl)-N-(2-methyl-2H-tetrazol-5-ylmethyl)amino]-3-hydroxy-2-methyl-2-dimethoxymethyl-3,4-dihydro-2H-1-benzopyran;

27) (2S,3R,4S)-6-nitro-4-[N-(4-methylphenyl)-N-(2-methyl-2H-tetrazol-5-ylmethyl)amino]-3-hydroxy-2-methyl-2-dimethoxymethyl-3,4-dihydro-2H-1-benzopyran;

28) (2S,3R,4S)-6-amino-4-[N-(4-methylphenyl)-N-(2-methyl-2H-tetrazol-5-ylmethyl)amino]-3-hydroxy-2-methyl-2-dimethoxymethyl-3,4-dihydro-2H-1-benzopyran;

29) (2S,3R,4S)-6-nitro-4-[N-(2-chlorophenyl)-N-(2-methyl-2H-tetrazol-5-ylmethyl)amino]-3-hydroxy-2-methyl-2-dimethoxymethyl-3,4-dihydro-2H-1-benzopyran;

30) (2S,3R,4S)-6-amino-4-[N-(2-chlorophenyl)-N-(2-methyl-2H-tetrazol-5-ylmethyl)amino]-3-hydroxy-2-methyl-2-dimethoxymethyl-3,4-dihydro-2H-1-benzopyran;

31) (2S,3R,4S)-6-nitro-4-[N-(4-trifluoromethoxyphenyl)-N-(2-methyl-2H-tetrazol-5-ylmethyl)amino]-3-hydroxy-2-methyl-2-dimethoxymethyl-3,4-dihydro-2H-1-benzopyran;

32) (2S,3R,4S)-6-amino-4-[N-(4-trifluoromethoxyphenyl)-N-(2-methyl-2H-tetrazol-5-ylmethyl)amino]-3-hydroxy-2-methyl-2-dimethoxymethyl-3,4-dihydro-2H-1-benzopyran;

33) (2S,3R,4S)-6-nitro-4-[N-(4-trifluoromethylphenyl)-N-(2-methyl-2H-tetrazol-5-ylmethyl)amino]-3-hydroxy-2-methyl-2-dimethoxymethyl-3,4-dihydro-2H-1-benzopyran;

34) (2S,3R,4S)-6-amino-4-[N-(4-trifluoromethylphenyl)-N-(2-methyl-2H-tetrazol-5-ylmethyl)amino]-3-hydroxy-2-methyl-2-dimethoxymethyl-3,4-dihydro-2H-1-benzopyran;

35) (2S,3R,4S)-6-nitro-4-[N-(3-acetylphenyl)-N-(2-methyl-2H-tetrazol-5-ylmethyl)amino]-3-hydroxy-2-methyl-2-dimethoxymethyl-3,4-dihydro-2H-1-benzopyran;

36) (2S,3R,4S)-6-amino-4-[N-[3-(1-hydroxyethyl)phenyl]-N-(2-methyl-2H-tetrazol-5-ylmethyl)amino]-3-hydroxy-2-methyl-2-dimethoxymethyl-3,4-dihydro-2H-1-benzopyran;

37) (2S,3R,4S)-6-nitro-4-[N-(2-methyl-4-fluorophenyl)-N-(2-methyl-2H-tetrazol-5-ylmethyl)amino]-3-hydroxy-2-methyl-2-dimethoxymethyl-3,4-dihydro-2H-1-benzopyran;

38) (2S,3R,4S)-6-amino-4-[N-(2-methyl-4-fluorophenyl)-N-(2-methyl-2H-tetrazol-5-ylmethyl)amino]-3-hydroxy-2-methyl-2-dimethoxymethyl-3,4-dihydro-2H-1-benzopyran;

39) (2S,3R,4S)-6-nitro-4-[N-(4-methoxyphenyl)-N-(2-methyl-2H-tetrazol-5-ylmethyl)amino]-3-hydroxy-2-methyl-2-dimethoxymethyl-3,4-dihydro-2H-1-benzopyran;

40) (2S,3R,4S)-6-amino-4-[N-(4-methoxyphenyl)-N-(2-methyl-2H-tetrazol-5-ylmethyl)amino]-3-hydroxy-2-methyl-2-dimethoxymethyl-3,4-dihydro-2H-1-benzopyran;

41) (2S,3R,4S)-6-nitro-4-[N-(2-methyl-4-chlorophenyl)-N-(2-methyl-2H-tetrazol-5-ylmethyl)amino]-3-hydroxy-2-methyl-2-dimethoxymethyl-3,4-dihydro-2H-1-benzopyran;

42) (2S,3R,4S)-6-amino-4-[N-(2-methyl-4-chlorophenyl)-N-(2-methyl-2H-tetrazol-5-ylmethyl)amino]-3-hydroxy-2-methyl-2-dimethoxymethyl-3,4-dihydro-2H-1-benzopyran;

43) (2S,3R,4S)-6-nitro-4-[N-(2-methoxy-5-methylphenyl)-N-(2-methyl-2H-tetrazol-5-ylmethyl)amino]-3-hydroxy-2-methyl-2-dimethoxymethyl-3,4-dihydro-2H-1-benzopyran;

44) (2S,3R,4S)-6-amino-4-[N-(2-methoxy-5-methylphenyl)-N-(2-methyl-2H-tetrazol-5-ylmethyl)amino]-3-hydroxy-2-methyl-2-dimethoxymethyl-3,4-dihydro-2H-1-benzopyran;

45) (2S,3R,4S)-6-nitro-4-[N-(2,4-dimethylphenyl)-N-(2-methyl-2H-tetrazol-5-ylmethyl)amino]-3-hydroxy-2-methyl-2-dimethoxymethyl-3,4-dihydro-2H-1-benzopyran;

46) (2S,3R,4S)-6-amino-4-[N-(2,4-dimethylphenyl)-N-(2-methyl-2H-tetrazol-5-ylmethyl)amino]-3-hydroxy-2-methyl-2-dimethoxymethyl-3,4-dihydro-2H-1-benzopyran;

47) (2S,3R,4S)-6-nitro-4-[N-(2,6-dimethylphenyl)-N-(2-methyl-2H-tetrazol-5-ylmethyl)amino]-3-hydroxy-2-methyl-2-dimethoxymethyl-3,4-dihydro-2H-1-benzopyran;

48) (2S,3R,4S)-6-amino-4-[N-(2,6-dimethylphenyl)-N-(2-methyl-2H-tetrazol-5-ylmethyl)amino]-3-hydroxy-2-methyl-2-dimethoxymethyl-3,4-dihydro-2H-1-benzopyran;
49) (2S,3R,4S)-6-nitro-4-[N-(2,3-dimethylphenyl)-N-(2-methyl-2H-tetrazol-5-ylmethyl)amino]-3-hydroxy-2-methyl-2-dimethoxymethyl-3,4-dihydro-2H-1-benzopyran;
50) (2S,3R,4S)-6-amino-4-[N-(2,3-dimethylphenyl)-N-(2-methyl-2H-tetrazol-5-ylmethyl)amino]-3-hydroxy-2-methyl-2-dimethoxymethyl-3,4-dihydro-2H-1-benzopyran;
51) (2S,3R,4S)-6-nitro-4-[N-(2-isopropylphenyl)-N-(2-methyl-2H-tetrazol-5-ylmethyl)amino]-3-hydroxy-2-methyl-2-dimethoxymethyl-3,4-dihydro-2H-1-benzopyran;
52) (2S,3R,4S)-6-amino-4-[N-(2-isopropylphenyl)-N-(2-methyl-2H-tetrazol-5-ylmethyl)amino]-3-hydroxy-2-methyl-2-dimethoxymethyl-3,4-dihydro-2H-1-benzopyran;
53) (2S,3R,4S)-6-nitro-4-[N-(4-ethoxycarbonylphenyl)-N-(2-methyl-2H-tetrazol-5-ylmethyl)amino]-3-hydroxy-2-methyl-2-dimethoxymethyl-3,4-dihydro-2H-1-benzopyran;
54) (2S,3R,4S)-6-amino-4-[N-(4-ethoxycarbonylphenyl)-N-(2-methyl-2H-tetrazol-5-ylmethyl)amino]-3-hydroxy-2-methyl-2-dimethoxymethyl-3,4-dihydro-2H-1-benzopyran;
55) (2S,3R,4S)-6-amino-4-[N-(2-methyl-2H-tetrazol-5-ylmethyl)phenylamino]-3-hydroxy-2-methyl-2-dimethoxymethyl-3,4-dihydro-2H-1-benzopyran;
56) (2S,3R,4S)-6-amino-4-[N-(4-fluorophenyl)-N-(2-methyl-2H-tetrazol-5-ylmethyl)amino]-3-hydroxy-2-methyl-2-dimethoxymethyl-3,4-dihydro-2H-1-benzopyran;
57) (2S,3R,4S)-6-amino-4-[N-benzyl-N-(2-methyl-2H-tetrazol-5-ylmethyl)amino]-3-hydroxy-2-methyl-2-dimethoxymethyl-3,4-dihydro-2H-1-benzopyran;
58) (2S,3R,4S)-6-nitro-4-[N-(3-methoxycarbonylphenyl)-N-(2-methyl-2H-tetrazol-5-ylmethyl)amino]-3-hydroxy-2-methyl-2-dimethoxymethyl-3,4-dihydro-2H-1-benzopyran;
59) (2S,3R,4S)-6-amino-4-[N-(3-methoxycarbonylphenyl)-N-(2-methyl-2H-tetrazol-5-ylmethyl)amino]-3-hydroxy-2-methyl-2-methoxymethyl-3,4-dihydro-2H-1-benzopyran;
60) (2S,3R,4S)-6-nitro-4-[N-(2-hydroxyphenyl)-N-(2-methyl-2H-tetrazol-5-ylmethyl)amino]-3-hydroxy-2-methyl-2-dimethoxymethyl-3,4-dihydro-2H-1-benzopyran;
61) (2S,3R,4S)-6-amino-4-[N-(2-hydroxyphenyl)-N-(2-methyl-2H-tetrazol-5-ylmethyl)amino]-3-hydroxy-2-methyl-2-dimethoxymethyl-3,4-dihydro-2H-1-benzopyran;
62) (2S,3R,4S)-6-nitro-4-[N-(2-methoxy-4-methoxycarbonylphenyl)-N-(2-methyl-2H-tetrazol-5-ylmethyl)amino]-3-hydroxy-2-methyl-2-dimethoxymethyl-3,4-dihydro-2H-1-benzopyran;
63) (2S,3R,4S)-6-amino-4-[N-(2-methoxy-4-methoxycarbonylphenyl)-N-(2-methyl-2H-tetrazol-5-ylmethyl)amino]-3-hydroxy-2-methyl-2-dimethoxymethyl-3,4-dihydro-2H-1-benzopyran;
64) (2S,3R,4S)-6-nitro-4-[N-(2-methyl-4-hydroxyphenyl)-N-(2-methyl-2H-tetrazol-5-ylmethyl)amino]-3-hydroxy-2-methyl-2-dimethoxymethyl-3,4-dihydro-2H-1-benzopyran;
65) (2S,3R,4S)-6-amino-4-[N-(2-methyl-4-hydroxyphenyl)-N-(2-methyl-2H-tetrazol-5-ylmethyl)amino]-3-hydroxy-2-methyl-2-dimethoxymethyl-3,4-dihydro-2H-1-benzopyran;
66) (2S,3R,4S)-6-nitro-4-[N-(2-ethylphenyl)-N-(2-methyl-2H-tetrazol-5-ylmethyl)amino]-3-hydroxy-2-methyl-2-dimethoxymethyl-3,4-dihydro-2H-1-benzopyran;
67) (2S,3R,4S)-6-amino-4-[N-(2-ethylphenyl)-N-(2-methyl-2H-tetrazol-5-ylmethyl)amino]-3-hydroxy-2-methyl-2-dimethoxymethyl-3,4-dihydro-2H-1-benzopyran;
68) (2S,3R,4S)-6-nitro-4-[N-(2-methyl-5-methoxycarbonylphenyl)-N-(2-methyl-2H-tetrazol-5-ylmethyl)amino]-3-hydroxy-2-methyl-2-dimethoxymethyl-3,4-dihydro-2H-1-benzopyran;
69) (2S,3R,4S)-6-amino-4-[N-(2-methyl-5-methoxycarbonylphenyl)-N-(2-methyl-2H-tetrazol-5-ylmethyl)amino]-3-hydroxy-2-methyl-2-dimethoxymethyl-3,4-dihydro-2H-1-benzopyran;
70) (2S,3R,4S)-6-nitro-4-[N-(2-hydroxy-5-methylphenyl)-N-(2-methyl-2H-tetrazol-5-ylmethyl)amino]-3-hydroxy-2-methyl-2-dimethoxymethyl-3,4-dihydro-2H-1-benzopyran;
71) (2S,3R,4S)-6-amino-4-[N-(2-hydroxy-5-methylphenyl)-N-(2-methyl-2H-tetrazol-5-ylmethyl)amino]-3-hydroxy-2-methyl-2-dimethoxymethyl-3,4-dihydro-2H-1-benzopyran;
72) (2S,3R,4S)-6-nitro-4-[N-(2,4,6-trimethylphenyl)-N-(2-methyl-2H-tetrazol-5-ylmethyl)amino]-3-hydroxy-2-methyl-2-dimethoxymethyl-3,4-dihydro-2H-1-benzopyran;
73) (2S,3R,4S)-6-amino-4-[N-(2,4,6-trimethylphenyl)-N-(2-methyl-2H-tetrazol-5-ylmethyl)amino]-3-hydroxy-2-methyl-2-dimethoxymethyl-3,4-dihydro-2H-1-benzopyran;
74) (2S,3S,4R)-6-nitro-4-[N-(4-trifluoromethylphenyl)-N-(2-methyl-2H-tetrazol-5-ylmethyl)amino]-3-hydroxy-2-methyl-2-dimethoxymethyl-3,4-dihydro-2H-1-benzopyran;
75) (2S,3S,4R)-6-amino-4-[N-(4-trifluoromethylphenyl)-N-(2-methyl-2H-tetrazol-5-ylmethyl)amino]-3-hydroxy-2-methyl-2-dimethoxymethyl-3,4-dihydro-2H-1-benzopyran;
76) (2R,3S,4R)-6-nitro-4-[N-(4-trifluoromethylphenyl)-N-(2-methyl-2H-tetrazol-5-ylmethyl)amino]-3-hydroxy-2-methyl-2-dimethoxymethyl-3,4-dihydro-2H-1-benzopyran;
77) (2R,3S,4 R)-6-amino-4-[N-(4-trifluoromethylphenyl)-N-(2-methyl-2H-tetrazol-5-ylmethyl)amino]-3-hydroxy-2-methyl-2-dimethoxymethyl-3,4-dihydro-2H-1-benzopyran;
78) (2R,3R,4S)-6-nitro-4-[N-(4-trifluoromethylphenyl)-N-(2-methyl-2H-tetrazol-5-ylmethyl)amino]-3-hydroxy-2-methyl-2-dimethoxymethyl-3,4-dihydro-2H-1-benzopyran;
79) (2R,3R,4S)-6-amino-4-[N-(4-trifluoromethylphenyl)-N-(2-methyl-2 H-tetrazol-5-ylmethyl)amino]-3-hydroxy-2-methyl-2-dimethoxymethyl-3,4-dihydro-2H-1-benzopyran;
80) (2S,3S,4R)-6-nitro-4-[N-(4-trifluoromethoxyphenyl)-N-(2-methyl-2H-tetrazol-5-ylmethyl)amino]-3-hydroxy-2-methyl-2-dimethoxymethyl-3,4-dihydro-2H-1-benzopyran;

81) (2S,3S,4R)-6-amino-4-[N-(4-trifluoromethoxyphenyl)-N-(2-methyl-2H-tetrazol-5-ylmethyl)amino]-3-hydroxy-2-methyl-2-dimethoxymethyl-3,4-dihydro-2H-1benzopyran;
82) (2R,3R,4S)-6-nitro-4-[N-(4-trifluoromethoxyphenyl)-N-(2-methyl-2H-tetrazol-5-ylmethyl)amino]-3-hydroxy-2-methyl-2-dimethoxymethyl-3,4-dihydro-2H-1-benzopyran;
83) (2R,3R,4S)-6-amino-4-[N-(4-trifluoromethoxyphenyl)-N-(2-methyl-2H-tetrazol-5-ylmethyl)amino]-3-hydroxy-2-methyl-2-dimethoxymethyl-3,4-dihydro-2H-1-benzopyran;
84) (2R,3S,4R)-6-nitro-4-[N-(4-trifluoromethoxyphenyl)-N-(2-methyl-2H-tetrazol-5-ylmethyl)amino]-3-hydroxy-2-methyl-2-dimethoxymethyl-3,4-dihydro-2H-1-benzopyran;
85) (2R,3S,4R)-6-amino-4-[N-(4-trifluoromethoxyphenyl)-N-(2-methyl-2H-tetrazol-5-ylmethyl)amino]-3-hydroxy-2-methyl-2-dimethoxymethyl-3,4-dihydro-2H-1-benzopyran;
86) (2S,3S,4R)-6-nitro-4-[N-(4-chlorophenyl)-N-(2-methyl-2H-tetrazol-5-ylmethyl)amino]-3-acetoxy-2-methyl-2-dimethoxymethyl-3,4-dihydro-2H-1-benzopyran;
87) (2S,3S,4R)-6-acetamino-4-[N-(4-chlorophenyl)-N-(2-methyl-2H-tetrazol-5-ylmethyl)amino]-3-acetoxy-2-methyl-2-dimethoxymethyl-3,4-dihydro-2H-1-benzopyran;
88) (2S,3S,4R)-6-acetamino-4-[N-(4-chlorophenyl)-N-(2-methyl-2H-tetrazol-5-ylmethyl)amino]-3-hydroxy-2-methyl-2-dimethoxymethyl-3,4-dihydro-2H-1-benzopyran;
89) (2S,3S,4R)-6-amino-4-[N-(4-chlorophenyl)-N-(2-methyl-2H-tetrazol-5-ylmethyl)amino]-3-acetoxy-2-methyl-2-dimethoxymethyl-3,4-dihydro-2H-1-benzopyran;
90) (2S,3R,4S)-6-bromo-4-[N-(4-chlorophenyl)-N-(2-methyl-2H-tetrazol-5-ylmethyl)amino]-3-hydroxy-2-methyl-2-dimethoxymethyl-3,4-dihydro-2H-1-benzopyran;
91) (2R,3R,4S)-6-bromo-4-[N-(4-chlorophenyl)-N-(2-methyl-2H-tetrazol-5-ylmethyl)amino]-3-hydroxy-2-methyl-2-dimethoxymethyl-3,4-dihydro-2H-1-benzopyran;
92) (2S,3R,4S)-6-bromo-4-[N-(4-fluorophenyl)-N-(2-methyl-2H-tetrazol-5-ylmethyl)amino]-3-hydroxy-2-methyl-2-dimethoxymethyl-3,4-dihydro-2H-1-benzopyran;
93) (2R,3R,4S)-6-bromo-4-[N-4-fluorophenyl)-N-(2-methyl-2H-tetrazol-5-ylmethyl)amino]-3-hydroxy-2-methyl-2-dimethoxymethyl-3,4-dihydro-2H-1-benzopyran;
94) (2R,3R,4S)-6-bromo-4-[N-(2-methyl-2H-tetrazol-5-ylmethyl)phenylamino]-3-hydroxy-2-methyl-2-dimethoxymethyl-3,4-dihydro-2H-1-benzopyran;
95) (2R,3S,4R)-6-methanesulfonyloxy-4-[N-(4-chlorophenyl)-N-(2-methyl-2H-tetrazol-5-ylmethyl)amino]-3-hydroxy-2-methyl-2-dimethoxymethyl-3,4-dihydro-2H-1-benzopyran;
96) (2S,3S,4R)-6-methanesulfonyloxy-4-[N-(4-chlorophenyl)-N-(2-methyl-2H-tetrazol-5-ylmethyl)amino]-3-hydroxy-2-methyl-2-dimethoxymethyl-3,4-dihydro-2H-1-benzopyran;
97) (2S,3S,4R)-6-hydroxy-4-[N-(4-chlorophenyl)-N-(2-methyl-2H-tetrazol-5-ylmethyl)amino]-3-hydroxy-2-methyl-2-dimethoxymethyl-3,4-dihydro-2H-1-benzopyran;
98) (2S,3S,4R)-6-nitro-5-methyl-4-[N-(4-chlorophenyl)-N-(2-methyl-2H-tetrazol-5-ylmethyl)amino]-3-hydroxy-2-methyl-2-dimethoxymethyl-3,4-dihydro-2H-1-benzopyran;
99) (2S,3S,4R)-6-nitro-4-[N-(4-fluorophenyl)-N-(2-methyl-2H-tetrazol-5-ylmethyl)amino]-3-hydroxy-2-methyl-2-methoxymethyl-3,4-dihydro-2H-1-benzopyran;
100) (2S,3S,4R)-6-hydroxy-4-[N-(4-chlorophenyl)-N-(2-methyl-2H-tetrazol-5-ylmethyl)amino]-3-hydroxy-2-methyl-2-dimethoxymethyl-3,4-dihydro-2H-1-benzopyran;
101) (2S,3S,4R)-8-nitro-4-[N-(4-chlorophenyl)-N-(2-methyl-2H-tetrazol-5-ylmethyl)amino]-3-hydroxy-2-methyl-2-dimethoxymethyl-3,4-dihydro-2H-1-benzopyran;
102) (2S,3S,4R)-8-amino-4-[N-(4-chlorophenyl)-N-(2-methyl-2H-tetrazol-5-ylmethyl)amino]-3-hydroxy-2-methyl-2-dimethoxymethyl-3,4-dihydro-2H-1-benzopyran;
103) (2R,3S,4R)-8-nitro-4-[N-(4-chlorophenyl)-N-(2-methyl-2H-tetrazol-5-ylmethyl)amino]-3-hydroxy-2-methyl-2-dimethoxymethyl-3,4-dihydro-2H-1-benzopyran;
104) (2R,3S,4R)-8-amino-4-[N-(4-chlorophenyl)-N-(2-methyl-2H-tetrazol-5-ylmethyl)amino]-3-hydroxy-2-methyl-2-dimethoxymethyl-3,4-dihydro-2H-1-benzopyran;
105) (2R,3R,4S)-6-nitro-4-[N-(4-chlorophenyl)-N-(2-methyl-2H-tetrazol-5-ylmethyl)amino]-3-hydroxy-2-methyl-2-dimethoxymethyl-3,4-dihydro-2H-1-benzopyran;
106) (2R,3R,4S)-6-amino-4-[N-(4-chlorophenyl)-N-(2-methyl-2H-tetrazol-5-ylmethyl)amino]-3-hydroxy-2-methyl-2-dimethoxymethyl-3,4-dihydro-2H-1-benzopyran;
107) (2R,3S,4R)-6-nitro-4-[N-(4-chlorophenyl)-N-(2-methyl-2H-tetrazol-5-ylmethyl)amino]-3-hydroxy-2-methyl-2-dimethoxymethyl-3,4-dihydro-2H-1-benzopyran;
108) (2R,3S,4R)-6-amino-4-[N-(4-chlorophenyl)-N-(2-methyl-2H-tetrazol-5-ylmethyl)amino]-3-hydroxy-2-methyl-2-dimethoxymethyl-3,4-dihydro-2H-1-benzopyran;
109) (2S,3R,4R)-6-nitro-4-[N-(4-chlorophenyl)-N-(2-methyl-2H-tetrazol-5-ylmethyl)amino]-3-hydroxy-2-methyl-2-dimethoxymethyl-3,4-dihydro-2H-1-benzopyran;
110) (2S,3R,4R)-6-amino-4-[N-(4-chlorophenyl)-N-(2-methyl-2H-tetrazol-5-ylmethyl)amino]-3-hydroxy-2-methyl-2-dimethoxymethyl-3,4-dihydro-2H-1-benzopyran;
111) (2S,3S,4S)-6-nitro-4-[N-(4-chlorophenyl)-N-(2-methyl-2H-tetrazol-5-ylmethyl)amino]-3-hydroxy-2-methyl-2-dimethoxymethyl-3,4-dihydro-2H-1-benzopyran;
112) (2S,3S,4S)-6-amino-4-[N-(4-chlorophenyl)-N-(2-methyl-2H-tetrazol-5-ylmethyl)amino]-3-hydroxy-2-methyl-2-dimethoxymethyl-3,4-dihydro-2H-1-benzopyran;
113) (2R,3R,4R)-6-nitro-4-[N-(4-chlorophenyl)-N-(2-methyl-2H-tetrazol-5-ylmethyl)amino]-3-hydroxy-2-methyl-2-dimethoxymethyl-3,4-dihydro-2H-1-benzopyran;
114) (2R,3R,4R)-6-amino-4-[N-(4-chlorophenyl)-N-(2-methyl-2H-tetrazol-5-ylmethyl)amino]-3-hydroxy-2-methyl-2-dimethoxymethyl-3,4-dihydro-2H-1-benzopyran;

115) (2R,3S,4S)-6-nitro-4-[N-(4-chlorophenyl)-N-(2-methyl-2H-tetrazol-5-ylmethyl)amino]-3-hydroxy-2-methyl-2-dimethoxymethyl-3,4-dihydro-2H-1-benzopyran; and 116) (2R,3S,4S)-6-amino-4-[N-(4-chlorophenyl)-N-(2-methyl-2H-tetrazol-5-ylmethyl)amino]-3-hydroxy-2-methyl-2-dimethoxymethyl-3,4-dihydro-2H-1-benzopyran.

3. A method for preparing the compound of claim 1, comprising the step of reacting the epoxide compound of formula 2 with secondary amines compound including heterocycle of formula 3 in the presence of metal salt selected from the group consisting of $Mg(ClO_4)_2$, $CoCl_2$, $LiClO_4$, $NaClO_4$, $CaCl_2$, $ZnCl_2$, $LiBF_4$ and $Zn(Tf)_2$ to obtain the compound of formula 1a:

CHEMICAL SCHEME 1

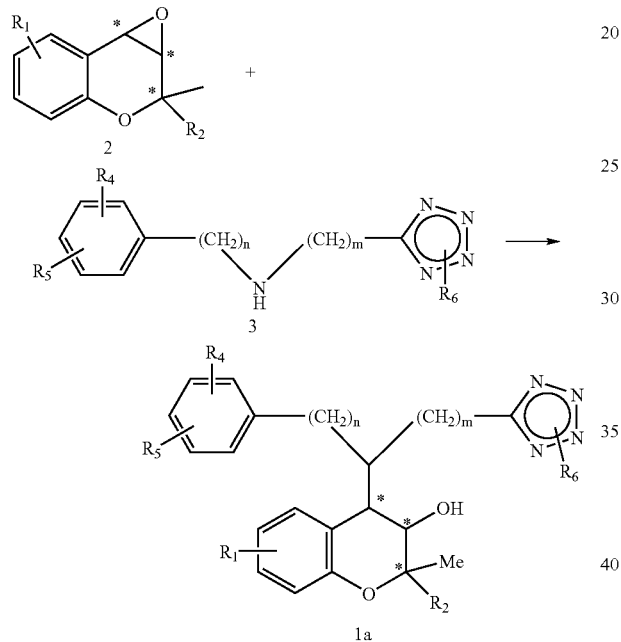

wherein, $R_1$, $R_2$, $R_4$, $R_5$, $R_6$, n, m, and * are same as defined in the claim 1.

4. The method according to claim 3, further comprising the step of reacting the compound of formula 1a by chemical scheme 2 to obtain the compound of formula 1:

CHEMICAL SCHEME 2

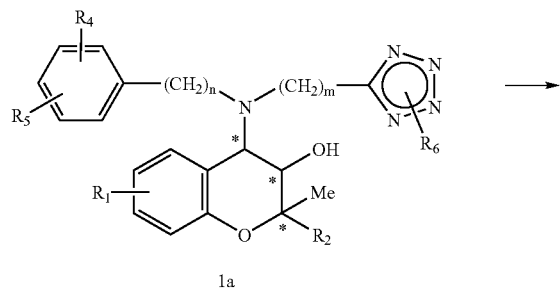

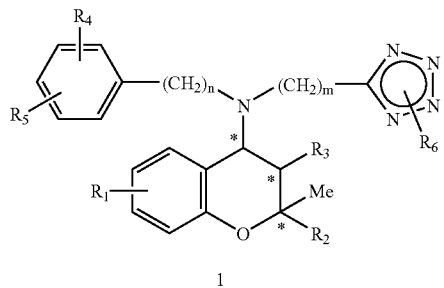

wherein, $R_1$, $R_2$, $R_3$, $R_4$, $R_5$, $R_6$, n, m, and * are same as defined in the claim 1.

5. A method for preparing the compound of claim 1, comprising the step of reducing the compound of formula 1c, wherein $R_1$ is $NO_2$ in the compound of formula 1a of claim 4, in the presence of reaction solvent selected from the group consisting of methanol, ethanol and ethyl acetate to obtain the compound of formula 1d:

CHEMICAL SCHEME 6

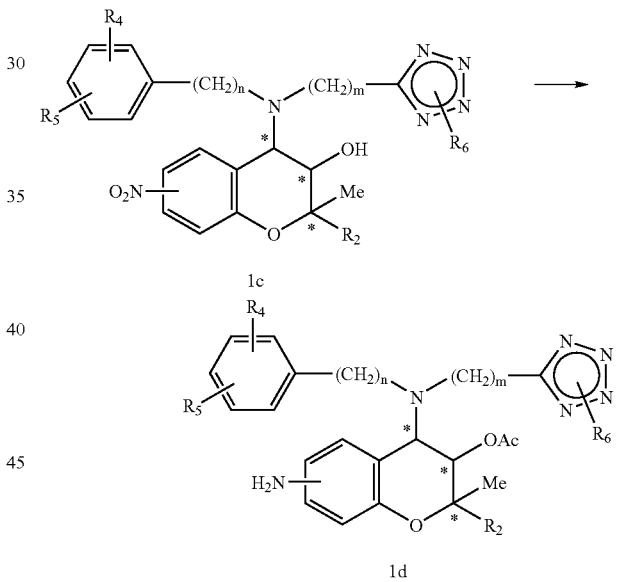

wherein, $R_2$, $R_4$, $R_5$, $R_6$, n and m are same as defined in the claim 1.

6. The method according to claim 5, wherein the reduction is carried by using a reducing agent such as $NaBH_4$ in the presence of metal catalyst selected from the group consisting of platinum, palladium on carbon (Pd/C) and Raney-nickel; $CuSO_4$; $Cu(OAc)_2$; $CoCl_2$; $SnCl_2$; or $NiCl_2$.

7. A cardioprotective composition comprising the compound of claim 1, stereoisomer thereof or pharmaceutically acceptable salt thereof as an effective ingredient.

* * * * *